(12) United States Patent
Busby et al.

(10) Patent No.: US 12,203,136 B2
(45) Date of Patent: Jan. 21, 2025

(54) METHODS AND SYSTEMS FOR SPATIAL MAPPING OF GENETIC VARIANTS

(71) Applicant: ReadCoor, LLC, Pleasanton, CA (US)

(72) Inventors: Michele A. Busby, Needham, MA (US); Evan Daugharthy, Cambridge, MA (US); Richard Terry, Carlisle, MA (US)

(73) Assignee: READCOOR, LLC, Pleasanton, CA (US)

( * ) Notice: Subject to any disclaimer, the term of this patent is extended or adjusted under 35 U.S.C. 154(b) by 0 days.

(21) Appl. No.: 18/345,629

(22) Filed: Jun. 30, 2023

(65) Prior Publication Data

US 2024/0150835 A1    May 9, 2024

Related U.S. Application Data

(63) Continuation of application No. 17/403,405, filed on Aug. 16, 2021, now abandoned.

(60) Provisional application No. 63/066,604, filed on Aug. 17, 2020.

(51) Int. Cl.
| | | |
|---|---|---|
| *C12Q 1/6881* | (2018.01) | |
| *C12Q 1/6837* | (2018.01) | |
| *C12Q 1/6841* | (2018.01) | |

(52) U.S. Cl.
CPC ......... *C12Q 1/6881* (2013.01); *C12Q 1/6837* (2013.01); *C12Q 1/6841* (2013.01); *C12Q 2600/106* (2013.01); *C12Q 2600/156* (2013.01); *C12Q 2600/16* (2013.01)

(58) Field of Classification Search
CPC .. C12Q 1/6881; C12Q 1/6837; C12Q 1/6841; C12Q 2600/106; C12Q 2600/156; C12Q 2600/16; C12Q 1/6825; C12Q 2537/143
See application file for complete search history.

(56) References Cited

U.S. PATENT DOCUMENTS

| | | |
|---|---|---|
| 3,501,459 A | 3/1970 | Schindler et al. |
| 3,551,710 A | 12/1970 | Gourdine |
| 3,871,445 A | 3/1975 | Wanka et al. |
| 3,993,233 A | 11/1976 | Bartell |
| 4,123,610 A | 10/1978 | Summerton et al. |
| 4,844,617 A | 7/1989 | Kelderman et al. |
| 4,886,741 A | 12/1989 | Schwartz |
| 4,981,985 A | 1/1991 | Kaplan et al. |
| 5,116,742 A | 5/1992 | Cech et al. |
| 5,151,189 A | 9/1992 | Hu et al. |
| 5,244,797 A | 9/1993 | Kotewicz et al. |
| 5,424,413 A | 6/1995 | Hogan et al. |
| 5,563,056 A | 10/1996 | Swan et al. |
| 5,594,235 A | 1/1997 | Lee |
| 5,635,352 A | 6/1997 | Urdea et al. |
| 5,684,149 A | 11/1997 | Morrow |
| 5,695,940 A | 12/1997 | Drmanac et al. |
| 5,795,236 A | 8/1998 | Alberts et al. |
| 5,830,708 A | 11/1998 | Naughton |
| 5,834,758 A | 11/1998 | Trulson et al. |
| 5,871,921 A | 2/1999 | Landegren et al. |
| 6,063,612 A | 5/2000 | Jayasena et al. |
| 6,068,979 A | 5/2000 | Akhavan-Tafti |
| 6,083,726 A | 7/2000 | Mills, Jr. et al. |
| 6,194,148 B1 | 2/2001 | Hori et al. |
| 6,221,603 B1 | 4/2001 | Mahtani |
| 6,232,067 B1 | 5/2001 | Hunkapiller et al. |
| 6,306,597 B1 | 10/2001 | Macevicz |
| 6,534,266 B1 | 3/2003 | Singer |
| 6,586,176 B1 | 7/2003 | Trnovsky et al. |
| 6,632,655 B1 | 10/2003 | Mehta et al. |
| 7,255,994 B2 | 8/2007 | Lao |
| 7,323,305 B2 | 1/2008 | Leamon et al. |
| 7,427,479 B2 | 9/2008 | Karger et al. |
| 7,473,767 B2 | 1/2009 | Dimitrov |
| 7,534,991 B2 | 5/2009 | Miller et al. |
| 7,555,155 B2 | 6/2009 | Levenson et al. |
| 7,655,898 B2 | 2/2010 | Miller |
| 7,745,129 B1 | 6/2010 | Schatz |
| 7,771,949 B2 | 8/2010 | Kramer |
| 7,906,285 B2 | 3/2011 | Drmanac |
| 7,910,304 B2 | 3/2011 | Drmanac |
| 7,941,279 B2 | 5/2011 | Hwang et al. |
| 7,989,166 B2 | 8/2011 | Koch et al. |
| 8,013,134 B2 | 9/2011 | Fredriksson |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,329,404 B2 | 12/2012 | McKernan et al. |
| 8,330,087 B2 | 12/2012 | Domenicali |
| 8,415,102 B2 | 4/2013 | Geiss et al. |

(Continued)

FOREIGN PATENT DOCUMENTS

| | | |
|---|---|---|
| BR | 112015013784 A2 | 7/2017 |
| BR | 112015013785 A2 | 7/2017 |

(Continued)

OTHER PUBLICATIONS

Hewitt, Immunology, vol. 110, pp. 163-169, published 2003.*
Soderberg et al., Nature Methods, vol. 3, pp. 995-1000, published online Oct. 29, 2006.*
Yao, Dong-Jing, et al. Expression of pax5 gene in wildtype zebrafish embryos. Academic Journal of Second Military Medical University; 32(1): 21-25, 2012 (Article in Chinese). English Abstract only provided.
AbouHaidar, et al., Non-enzymatic RNA Hydrolysis promoted by the combined catalytic activity of buffers and magnesium Ions. Verlag der Zeitschrift fur naturforschung. Tubingen. 1999; 54c: 542-548.

(Continued)

*Primary Examiner* — Narayan K Bhat
(74) *Attorney, Agent, or Firm* — Wilson Sonsini Goodrich & Rosati

(57) ABSTRACT

The present disclosure provides methods and systems for analyzing a biological sample from a subject, comprising using probes to identify and determine the location of different genetic sequences.

20 Claims, 5 Drawing Sheets

Specification includes a Sequence Listing.

(56) References Cited

U.S. PATENT DOCUMENTS

| | | |
|---|---|---|
| 8,431,691 B2 | 4/2013 | McKernan et al. |
| 8,460,865 B2 | 6/2013 | Chee et al. |
| 8,462,981 B2 | 6/2013 | Determan et al. |
| 8,501,459 B2 | 8/2013 | Chen et al. |
| 8,519,115 B2 | 8/2013 | Webster et al. |
| 8,551,710 B2 | 10/2013 | Bernitz et al. |
| 8,658,361 B2 | 2/2014 | Wu et al. |
| 8,697,359 B1 | 4/2014 | Zhang |
| 8,871,445 B2 | 10/2014 | Cong et al. |
| 8,906,616 B2 | 12/2014 | Zhang et al. |
| 8,932,814 B2 | 1/2015 | Cong et al. |
| 8,946,389 B2 | 2/2015 | Gao et al. |
| 8,986,926 B2 | 3/2015 | Ferree et al. |
| 8,993,233 B2 | 3/2015 | Zhang et al. |
| 8,999,641 B2 | 4/2015 | Zhang et al. |
| 9,017,992 B2 | 4/2015 | Winther et al. |
| 9,201,063 B2 | 12/2015 | Sood et al. |
| 9,217,151 B2 | 12/2015 | Yin et al. |
| 9,232,067 B2 | 1/2016 | Leigh et al. |
| 9,257,135 B2 | 2/2016 | Ong et al. |
| 9,267,135 B2 | 2/2016 | Church et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,541,504 B2 | 1/2017 | Hoyt |
| 9,551,032 B2 | 1/2017 | Landegren et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,896,720 B2 | 2/2018 | Raj et al. |
| 9,909,167 B2 | 3/2018 | Samusik et al. |
| 9,914,967 B2 | 3/2018 | Church et al. |
| 10,030,261 B2 | 7/2018 | Frisen et al. |
| 10,032,064 B2 | 7/2018 | Hoyt |
| 10,036,055 B2 | 7/2018 | Church et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,494,664 B2 | 12/2019 | Doudna et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,538,795 B2 | 1/2020 | Seitz et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisen et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,844,426 B2 | 11/2020 | Daugharthy et al. |
| 10,858,692 B2 | 12/2020 | Church et al. |
| 10,872,679 B2 | 12/2020 | Cai et al. |
| 10,964,001 B2 | 3/2021 | Miller |
| 11,021,737 B2 | 6/2021 | Church et al. |
| 11,021,741 B2 | 6/2021 | Wu et al. |
| 11,078,520 B2 | 8/2021 | Church et al. |
| 11,085,072 B2 | 8/2021 | Church et al. |
| 11,111,521 B2 | 9/2021 | Church et al. |
| 11,118,220 B2 | 9/2021 | Daugharthy et al. |
| 11,193,163 B2 | 12/2021 | Daugharthy et al. |
| 11,293,051 B2 | 4/2022 | Church et al. |
| 11,293,052 B2 | 4/2022 | Church et al. |
| 11,293,054 B2 | 4/2022 | Levner et al. |
| 11,299,767 B2 | 4/2022 | Church et al. |
| 11,312,992 B2 | 4/2022 | Church et al. |
| 11,447,807 B2 | 9/2022 | Church et al. |
| 11,466,310 B2 | 10/2022 | Daniel |
| 11,473,139 B2 | 10/2022 | Church et al. |
| 11,542,554 B2 | 1/2023 | Daugharthy et al. |
| 11,549,136 B2 | 1/2023 | Church et al. |
| 11,566,276 B2 | 1/2023 | Church et al. |
| 11,566,277 B2 | 1/2023 | Church et al. |
| 11,639,518 B2 | 5/2023 | Church et al. |
| 11,713,485 B2 | 8/2023 | Daugharthy et al. |
| 11,718,874 B2 | 8/2023 | Daugharthy et al. |
| 2001/0039018 A1 | 11/2001 | Matson et al. |
| 2002/0015952 A1 | 2/2002 | Anderson et al. |
| 2002/0029979 A1 | 3/2002 | Freund et al. |
| 2002/0049176 A1 | 4/2002 | Anderson et al. |
| 2002/0155989 A1 | 10/2002 | Efimov et al. |
| 2002/0168645 A1 | 11/2002 | Taylor |
| 2002/0172950 A1 | 11/2002 | Kenny et al. |
| 2003/0018984 A1 | 1/2003 | Coleman et al. |
| 2003/0148335 A1 | 8/2003 | Shen et al. |
| 2003/0165852 A1 | 9/2003 | Schueler et al. |
| 2004/0006035 A1 | 1/2004 | Macejak et al. |
| 2004/0077014 A1 | 4/2004 | Becker |
| 2004/0081962 A1 | 4/2004 | Chen et al. |
| 2004/0081979 A1 | 4/2004 | Knezevic et al. |
| 2004/0126770 A1 | 7/2004 | Kumar et al. |
| 2004/0152072 A1 | 8/2004 | Gerard |
| 2004/0191794 A1* | 9/2004 | Weindel ............... C12Q 1/6816 435/91.2 |
| 2004/0248144 A1 | 12/2004 | Mir |
| 2004/0259190 A1 | 12/2004 | Naughton |
| 2004/0259226 A1 | 12/2004 | Robey et al. |
| 2005/0032694 A1 | 2/2005 | Sonderegger |
| 2005/0064435 A1 | 3/2005 | Su et al. |
| 2005/0106629 A1 | 5/2005 | McGrath et al. |
| 2005/0147981 A1 | 7/2005 | Yamakawa et al. |
| 2005/0191687 A1 | 9/2005 | Wang et al. |
| 2005/0221304 A1 | 10/2005 | Xiang et al. |
| 2005/0233318 A1 | 10/2005 | Chee et al. |
| 2006/0024711 A1 | 2/2006 | Lapidus et al. |
| 2006/0046311 A1 | 3/2006 | Sun et al. |
| 2006/0077536 A1 | 4/2006 | Bromage et al. |
| 2006/0127916 A1 | 6/2006 | Seul et al. |
| 2006/0177833 A1 | 8/2006 | Brenner |
| 2006/0183107 A1 | 8/2006 | Melkonyan |
| 2006/0216339 A1 | 9/2006 | Ambron et al. |
| 2006/0228733 A1 | 10/2006 | Pierce et al. |
| 2006/0234261 A1 | 10/2006 | Pierce et al. |
| 2006/0248349 A1 | 11/2006 | Rathjen et al. |
| 2006/0292611 A1 | 12/2006 | Berka et al. |
| 2007/0003949 A1 | 1/2007 | Rava |
| 2007/0020650 A1 | 1/2007 | Kahvejian |
| 2007/0087362 A1 | 4/2007 | Church et al. |
| 2007/0117109 A1 | 5/2007 | Rothemund |
| 2007/0117177 A1 | 5/2007 | Luo et al. |
| 2007/0172873 A1 | 7/2007 | Brenner et al. |
| 2007/0190543 A1 | 8/2007 | Livak |
| 2007/0206275 A1 | 9/2007 | Hemmer et al. |
| 2007/0212700 A1 | 9/2007 | Ranganathan et al. |
| 2007/0231823 A1 | 10/2007 | McKernan et al. |
| 2007/0292877 A1 | 12/2007 | Dimitrov |
| 2008/0003586 A1 | 1/2008 | Hyde et al. |
| 2008/0003599 A1 | 1/2008 | Dary et al. |
| 2008/0050718 A1 | 2/2008 | Gesteland et al. |
| 2008/0176769 A1 | 7/2008 | Rank et al. |
| 2008/0180790 A1 | 7/2008 | Tafas et al. |
| 2008/0269068 A1 | 10/2008 | Church et al. |

(56) References Cited

U.S. PATENT DOCUMENTS

| | | |
|---|---|---|
| 2009/0088327 A1 | 4/2009 | Rigatti et al. |
| 2009/0105082 A1 | 4/2009 | Chetverin et al. |
| 2009/0208965 A1 | 8/2009 | Tafas et al. |
| 2009/0220968 A1 | 9/2009 | Issadore et al. |
| 2009/0246879 A1 | 10/2009 | Drmanac et al. |
| 2009/0269739 A1 | 10/2009 | Cech et al. |
| 2009/0280559 A1 | 11/2009 | McCarthy |
| 2009/0307179 A1* | 12/2009 | Colby .................. G16H 10/40 706/54 |
| 2009/0325172 A1 | 12/2009 | Milton et al. |
| 2010/0009868 A1 | 1/2010 | Yan et al. |
| 2010/0015607 A1 | 1/2010 | Geiss et al. |
| 2010/0028885 A1 | 2/2010 | Balasubramanian et al. |
| 2010/0049448 A1 | 2/2010 | Doyle et al. |
| 2010/0076057 A1 | 3/2010 | Sontheimer et al. |
| 2010/0087325 A1 | 4/2010 | Buermann |
| 2010/0151472 A1 | 6/2010 | Nolan et al. |
| 2010/0223276 A1 | 9/2010 | Al-Shameri et al. |
| 2010/0268478 A1 | 10/2010 | Andregg et al. |
| 2011/0020291 A1 | 1/2011 | Banerjee et al. |
| 2011/0033520 A1 | 2/2011 | Mather et al. |
| 2011/0090562 A1 | 4/2011 | Brooker |
| 2011/0092376 A1 | 4/2011 | Colston, Jr. et al. |
| 2011/0104693 A1 | 5/2011 | Seligmann |
| 2011/0189776 A1 | 8/2011 | Terns et al. |
| 2011/0208040 A1 | 8/2011 | Carmi et al. |
| 2011/0216953 A1 | 9/2011 | Callahan et al. |
| 2011/0223585 A1 | 9/2011 | Gullberg et al. |
| 2011/0223638 A1 | 9/2011 | Wiedenheft et al. |
| 2011/0257031 A1 | 10/2011 | Bodeau et al. |
| 2011/0294135 A1 | 12/2011 | Carlson |
| 2012/0040397 A1 | 2/2012 | Luo et al. |
| 2012/0122712 A1 | 5/2012 | Goldstein |
| 2012/0126142 A1 | 5/2012 | Matsui et al. |
| 2012/0252686 A1 | 10/2012 | Umbarger et al. |
| 2012/0270214 A1 | 10/2012 | Bernitz et al. |
| 2012/0330636 A1 | 12/2012 | Albou |
| 2013/0017229 A1 | 1/2013 | Mooney et al. |
| 2013/0130248 A1 | 5/2013 | Haurwitz et al. |
| 2013/0245096 A1 | 9/2013 | Abitbol |
| 2013/0253040 A1 | 9/2013 | Miller et al. |
| 2013/0323729 A1 | 12/2013 | Landegren et al. |
| 2014/0049632 A1 | 2/2014 | Hemmer |
| 2014/0068797 A1 | 3/2014 | Doudna et al. |
| 2014/0087378 A1 | 3/2014 | Chatre et al. |
| 2014/0087427 A1 | 3/2014 | Bujnicki et al. |
| 2014/0179006 A1 | 6/2014 | Zhang |
| 2014/0179770 A1 | 6/2014 | Zhang et al. |
| 2014/0200146 A1 | 7/2014 | Xie et al. |
| 2014/0220578 A1 | 8/2014 | Bohannon et al. |
| 2014/0220587 A1 | 8/2014 | Green, Jr. et al. |
| 2014/0270435 A1 | 9/2014 | Dunn |
| 2014/0273226 A1 | 9/2014 | Wu |
| 2014/0273233 A1 | 9/2014 | Chen et al. |
| 2014/0308695 A1 | 10/2014 | Bruce et al. |
| 2014/0310830 A1 | 10/2014 | Zhang et al. |
| 2014/0315985 A1 | 10/2014 | May et al. |
| 2014/0342457 A1 | 11/2014 | Mali et al. |
| 2015/0098126 A1 | 4/2015 | Keller et al. |
| 2015/0133319 A1 | 5/2015 | Fu et al. |
| 2015/0247150 A1 | 9/2015 | Zhang et al. |
| 2016/0002704 A1 | 1/2016 | Diehl et al. |
| 2016/0024524 A1 | 1/2016 | Joung et al. |
| 2016/0024555 A1* | 1/2016 | Church ................ C12Q 1/6844 435/6.12 |
| 2016/0106439 A1 | 4/2016 | Menashe |
| 2016/0108458 A1 | 4/2016 | Frei et al. |
| 2016/0153006 A1 | 6/2016 | Zhang et al. |
| 2016/0160210 A1 | 6/2016 | Mali et al. |
| 2016/0265046 A1 | 9/2016 | Zhang et al. |
| 2016/0289740 A1 | 10/2016 | Fu et al. |
| 2016/0305856 A1 | 10/2016 | Boyden et al. |
| 2016/0340662 A1 | 11/2016 | Zhang et al. |
| 2016/0355795 A1 | 12/2016 | Ran et al. |
| 2016/0358326 A1 | 12/2016 | Sarachan et al. |
| 2016/0369321 A1 | 12/2016 | Landegren et al. |
| 2016/0376642 A1 | 12/2016 | Landegren et al. |
| 2017/0009278 A1 | 1/2017 | Söderberg et al. |
| 2017/0010672 A1 | 1/2017 | Tanaka et al. |
| 2017/0081489 A1 | 3/2017 | Rodriques et al. |
| 2017/0176338 A1 | 6/2017 | Wu et al. |
| 2017/0191078 A1 | 7/2017 | Zhang et al. |
| 2017/0220733 A1 | 8/2017 | Zhuang et al. |
| 2017/0253918 A1 | 9/2017 | Kohman |
| 2017/0262984 A1 | 9/2017 | Barnes et al. |
| 2018/0010166 A1 | 1/2018 | Pierce et al. |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0282787 A1 | 10/2018 | Walter et al. |
| 2019/0017106 A1 | 1/2019 | Frisen et al. |
| 2019/0032128 A1 | 1/2019 | Chen et al. |
| 2019/0032151 A1* | 1/2019 | Wallin .................. A61K 45/06 |
| 2019/0085383 A1 | 3/2019 | Church et al. |
| 2019/0119735 A1 | 4/2019 | Deisseroth et al. |
| 2019/0130607 A1* | 5/2019 | Atchison .................. G06T 7/90 |
| 2019/0155835 A1 | 5/2019 | Daugharthy et al. |
| 2019/0194709 A1 | 6/2019 | Church et al. |
| 2019/0218608 A1 | 7/2019 | Daugharthy et al. |
| 2019/0241938 A1 | 8/2019 | Levner et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0330617 A1 | 10/2019 | Church et al. |
| 2020/0009786 A1 | 1/2020 | Hikmet et al. |
| 2020/0010891 A1 | 1/2020 | Beechem et al. |
| 2020/0034347 A1 | 1/2020 | Selly |
| 2020/0090786 A1 | 3/2020 | Quiroz Zarate et al. |
| 2020/0140920 A1 | 5/2020 | Pierce et al. |
| 2020/0239946 A1 | 7/2020 | Dewal |
| 2020/0354782 A1 | 11/2020 | Dewal |
| 2021/0017587 A1 | 1/2021 | Cai et al. |
| 2021/0087611 A1 | 3/2021 | Church et al. |
| 2021/0102244 A1 | 4/2021 | Church et al. |
| 2021/0115504 A1 | 4/2021 | Cai et al. |
| 2021/0292834 A1 | 9/2021 | Daugharthy et al. |
| 2021/0310052 A1 | 10/2021 | Daugharthy et al. |
| 2021/0324450 A1 | 10/2021 | Church et al. |
| 2021/0332414 A1 | 10/2021 | Church |
| 2021/0332415 A1 | 10/2021 | Church et al. |
| 2021/0340621 A1 | 11/2021 | Daugharthy et al. |
| 2021/0363579 A1 | 11/2021 | Daugharthy et al. |
| 2021/0381049 A1 | 12/2021 | Daugharthy et al. |
| 2022/0016624 A1 | 1/2022 | Daugharthy et al. |
| 2022/0025448 A1 | 1/2022 | Levner et al. |
| 2022/0049303 A1 | 2/2022 | Busby et al. |
| 2022/0145365 A1 | 5/2022 | Church et al. |
| 2022/0228196 A1 | 7/2022 | Church et al. |
| 2022/0251642 A1 | 8/2022 | Church et al. |
| 2022/0282301 A1 | 9/2022 | Levner et al. |
| 2022/0298559 A1 | 9/2022 | Daugharthy et al. |
| 2023/0212649 A1 | 7/2023 | Church et al. |
| 2024/0018569 A1 | 1/2024 | Levner et al. |
| 2024/0124932 A1 | 4/2024 | Daugharthy et al. |

FOREIGN PATENT DOCUMENTS

| | | |
|---|---|---|
| BR | 112015008708 A2 | 9/2017 |
| BR | 112015012375 A2 | 9/2017 |
| BR | 112015014425 A2 | 10/2017 |
| BR | 112015022061 A2 | 11/2017 |
| CA | 2116214 A1 | 3/1993 |
| CA | 2891347 A1 | 6/2014 |
| CN | 1432069 A | 7/2003 |
| CN | 1580283 A | 2/2005 |
| CN | 1959384 A | 5/2007 |
| CN | 101285095 A | 10/2008 |
| CN | 101400803 A | 4/2009 |
| CN | 101553306 A | 10/2009 |
| CN | 101608232 A | 12/2009 |
| CN | 103364380 A | 10/2013 |
| CN | 105264073 A | 1/2016 |
| CN | 105392898 A | 3/2016 |

(56) References Cited

FOREIGN PATENT DOCUMENTS

| | | |
|---|---|---|
| EP | 2288726 A2 | 3/2011 |
| EP | 2465943 A2 | 6/2012 |
| EP | 2798092 A2 | 11/2014 |
| EP | 2878671 A1 | 6/2015 |
| EP | 3425063 A1 | 1/2019 |
| EP | 2794928 B1 | 2/2019 |
| EP | 2971184 B1 | 4/2019 |
| EP | 2766498 B1 | 6/2019 |
| EP | 3578666 A1 | 12/2019 |
| EP | 3847274 A1 | 7/2021 |
| EP | 4108782 B1 | 6/2023 |
| JP | H04268359 A | 9/1992 |
| JP | 2007526772 A | 9/2007 |
| JP | 2009538123 A | 11/2009 |
| JP | 2012170337 A | 9/2012 |
| JP | 2014513523 A | 6/2014 |
| JP | 2015090458 A | 5/2015 |
| KR | 20080003402 A | 1/2008 |
| WO | WO-9746704 A1 | 12/1997 |
| WO | WO-9856955 A1 | 12/1998 |
| WO | WO-9961665 A2 | 12/1999 |
| WO | WO-0126708 A1 | 4/2001 |
| WO | WO-0137266 A1 | 5/2001 |
| WO | WO-03003810 A2 | 1/2003 |
| WO | WO-03044229 A1 | 5/2003 |
| WO | WO-03102233 A1 | 12/2003 |
| WO | WO-2004104645 A2 | 12/2004 |
| WO | WO-2006138257 A2 | 12/2006 |
| WO | WO-2007001986 A2 | 1/2007 |
| WO | WO-2007076128 A2 | 7/2007 |
| WO | WO-2007086900 A2 | 8/2007 |
| WO | WO-2007121489 A2 | 10/2007 |
| WO | WO-2007123744 A2 | 11/2007 |
| WO | WO-2007149696 A1 | 12/2007 |
| WO | WO-2008041002 A2 | 4/2008 |
| WO | WO-2008069973 A2 | 6/2008 |
| WO | WO-2008108989 A2 | 9/2008 |
| WO | WO-2008157696 A2 | 12/2008 |
| WO | WO-2009046149 A1 | 4/2009 |
| WO | WO-2009046348 A1 | 4/2009 |
| WO | WO-2010054108 A2 | 5/2010 |
| WO | WO-2010080134 A1 | 7/2010 |
| WO | WO-2010087325 A1 | 8/2010 |
| WO | WO-2010104533 A2 | 9/2010 |
| WO | WO-2011092596 A2 | 8/2011 |
| WO | WO-2011143124 A2 | 11/2011 |
| WO | WO-2011143583 A1 | 11/2011 |
| WO | WO-2012005595 A2 | 1/2012 |
| WO | WO-2012058638 A2 | 5/2012 |
| WO | WO-2012083189 A2 | 6/2012 |
| WO | WO-2012110899 A2 | 8/2012 |
| WO | WO-2012129242 A2 | 9/2012 |
| WO | WO-2012150035 A1 | 11/2012 |
| WO | WO-2012164565 A1 | 12/2012 |
| WO | WO-2013055995 A2 | 4/2013 |
| WO | WO-2013096851 A1 | 6/2013 |
| WO | WO-2013098244 A1 | 7/2013 |
| WO | WO-2013126794 A1 | 8/2013 |
| WO | WO-2013141680 A1 | 9/2013 |
| WO | WO-2013142578 A1 | 9/2013 |
| WO | WO-2013176772 A1 | 11/2013 |
| WO | WO-2013184754 A2 | 12/2013 |
| WO | WO-2014022702 A2 | 2/2014 |
| WO | WO-2014048083 A1 | 4/2014 |
| WO | WO-2014065596 A1 | 5/2014 |
| WO | WO-2014089290 A1 | 6/2014 |
| WO | WO-2014093595 A1 | 6/2014 |
| WO | WO-2014093622 A2 | 6/2014 |
| WO | WO-2014093661 A2 | 6/2014 |
| WO | WO-2014093694 A1 | 6/2014 |
| WO | WO-2014099744 A1 | 6/2014 |
| WO | WO-2014113493 A1 | 7/2014 |
| WO | WO-2014144288 A1 | 9/2014 |
| WO | WO-2014150624 A1 | 9/2014 |
| WO | WO-2014163886 A1 | 10/2014 |
| WO | WO-2014182528 A2 | 11/2014 |
| WO | WO-2014191518 A1 | 12/2014 |
| WO | WO-2014197568 A2 | 12/2014 |
| WO | WO-2015002813 A1 | 1/2015 |
| WO | WO-2015118029 A1 | 8/2015 |
| WO | WO-2015127183 A2 | 8/2015 |
| WO | WO-2015148606 A2 | 10/2015 |
| WO | WO-2016007839 A1 | 1/2016 |
| WO | WO-2016081740 A1 | 5/2016 |
| WO | WO-2017015018 A1 | 1/2017 |
| WO | WO-2017019456 A2 | 2/2017 |
| WO | WO-2017079382 A1 | 5/2017 |
| WO | WO-2017079406 A1 | 5/2017 |
| WO | WO-2017143155 A2 | 8/2017 |
| WO | WO-2017161251 A1 | 9/2017 |
| WO | WO-2017189525 A1 | 11/2017 |
| WO | WO-2018045181 A1 | 3/2018 |
| WO | WO-2018045186 A1 | 3/2018 |
| WO | WO-2018089445 A1 | 5/2018 |
| WO | WO-2018187791 A1 | 10/2018 |
| WO | WO-2019103996 A1 | 5/2019 |
| WO | WO-2019217758 A1 | 11/2019 |
| WO | WO-2020028194 A1 | 2/2020 |
| WO | WO-2020076976 | 4/2020 |
| WO | WO-2020076979 | 4/2020 |
| WO | WO-2020096687 A1 | 5/2020 |
| WO | WO-2020198071 A1 | 10/2020 |
| WO | WO-2021155063 | 8/2021 |
| WO | WO-2021168326 | 8/2021 |

OTHER PUBLICATIONS

Achim et al., High-throughput spatial mapping of single-cell RNA-seq data to tissue of origin. Nature Biotechnology, vol. 33, No. 5, May 2015, p. 503-511.

Agaouglu et al. Ultra-sensitive microfluidic wearable strain sensor for intraocular pressure monitoring. Lab on a Chip, Issue 22, 2018; pp. 3471-3483.

Al-Attar et al., Clustered Regularly Interspaced Short Palindromic Repeats (CRISPRs ): The Hallmark of an Ingenious Antiviral Defense Mechanism in Prokaryotes, Bio Chem. (2011) vol. 392, Issue 4, pp. 277-289.

Altshuler D, Daly MJ, Lander ES. 2008. "Genetic mapping in human disease" Science 322: 881-8.

Amasino et al., Acceleration of nucleic acid hybridization rate by polyethylene glycol, Analytical biochemistry, vol. 152, No. 2, Feb. 1, 1986.

Ansari et al., Riboactivators: Transcription activation by non-coding RNA, Grit Rev Biochem Mol Bioi. 2009 ; 44(1 ): 50-61.

Arezi et al., Novel mutations in Moloney Murine Leukemia Virus reverse transcriptase increase thermostability through tighter binding to template-primer. Nucleic Acids Research 37(2) : 473-481 (Year: 2009).

Ascano., Identification of RNA-protein interaction networks using PAR-CLIP. Wiley interdisciplinary reviews. RNA 3.2 (Mar. 2012): 159-177, DOI:10.1002/wma.1103.

Bálint, et al. Correlative live-cell and superresolution microscopy reveals cargo transport dynamics at microtubule intersections. Proceedings of the National Academy of Sciences. Feb. 2, 20136;110(9): pp. 3375-3380.

Bakal C, Aach J, Church G, Perrimon N. 2007. "Quantitative morphological signatures define local signaling networks regulating cell morphology" Science 316: 1753-6.

Ball et al., Targeted and genome-scale strategies reveal gene-body methylation signatures in human cells. Nat Biotechnol. 27(4):361-368 (2009).

Bang D, Church GM. 2008. "Gene synthesis by circular assembly amplification" Nat Methods 5: 37-9.

Bao, et al. A Novel DNA Detection Method Based on Gold Nanoparticle Probes and Gene Chips. Acta Chimica Sinica No. 18, 2144-2148. 2009. English Abstract provided.

Beliveau, Brian J. et al., Versatile design and synthesis platform for visualizing genomes with Oligopaint FISH probes, National Academy of Sciences, vol. 109, No. 52, Dec. 11, 2012, pp. 21301-21306.

(56) References Cited

OTHER PUBLICATIONS

Beliveau, Brian J. et al., Visualizing Genomes with Oligopaint Fish Probes: In: "Current Protocols in Molecular Biology", Jan. 6, 2014, Wiley, New York, NY.
Beliveau, et al. Single-molecule super-resolution imaging of chromosomes and in situ haplotype visualization using olligopaint FISH probes. Nat Commun. 2015; 6:7147; Abstract, p. 3 [according to the posted document], Fig 1 and its legend; p. 4, Fig 2 and its legend; p. 6, Fig 3 and its legend.
Bell J. 2004. "Predicting disease using genomics" Nature 429: 453-6.
Bibikova et al. "Quantitative Gene Expression Profiling in Formalin-Fixed, Paraffin-Embedded Tissues Using Universal Bead Arrays" American Journal of Pathology, vol. 165, No. 5, Nov. 2004.
Bock, RM. Alkaline Hydrolysis of RNA. Methods in Enzymology 12 : 224-228 (Year: 1967).
Bouche et al., The effect of spermidine on endonuclease inhibition by agarose contaminants. Analytical biochemistry, Academic press, vol. 115, No. 1, Jul. 15, 1918, pp. 42-45.
Brenner, et al., Gene Expression analysis by massively parallel signature sequencing (MPSS) on microbead arrays. Nature Biotechnology 18.6 (Jun. 2000): 630-634, doi:10.1038/76469.
Brenner, et al. "In vitro cloning of complex mixtures of DNA on microbeads: physical separation of differentially expressed cDNAs." Proc Natl Acad Sci U S A. Feb. 15, 2000;97(4):1665-70.
Brown et al., Review Article : In situ Hybridization with Riboprobes :An Overview for Veterinary Pathologists. Veterinary Pathology 35 : 159-167 (Year: 1998.
Cao, et al., In-situ Immuno-PCR to detect antigens. The Lancet 356 (Sep. 2000): 1002-1003.
Capodieci et al. "Gene expression profiling in single cells within tissue" Nature Methods, Sep. 14, 2005, 2(9) pp. 663-665.
Carroll, "A CRISPR Approach to Gene Targeting" 20(9) Molecular Therapy 1658-1660 (Sep. 2012).
Chen, et al., Expansion Microscopy. Science, Jan. 30, 2015; vol. 347, Issue 6221: 543-549.
Chen et al., Functional organization of the human 4D Nucleome, PNAS Jun. 30, 2015 112 (26) 8002-8007; first published Jun. 15, 2015.
Chen, et al., Nanoscale imaging of RNA with expansion microscopy. Nature Methods. Aug. 2016; vol. 13, No. 8: pp. 679-687.
Chen et al. "Spatially resolved, highly multiplexed RNA profiling in single cells". Science. Apr. 24, 2015;348(6233):aaa6090, pp. 1-14.
Cheng, et al. Multiplexed Activation of Endogenous Genes by CRISPR-on, An RNA-Guided Transcriptional Activator System. Cell Research. vol. 23. No. 10. Oct. 1, 2013. pp. 1163-1171.
Chiang DY, Getz G, Jaffe DB, O'Kelly MJ, Zhao X, Carter SL, Russ C, Nusbaum C, Meyerson M, Lander ES. 2009. High-resolution mapping of copy-number alterations with massively parallel sequencing Nat Methods 6: 99-103. PMC ID: PMC2630795.
Choi & Love et al., Immuno-Hybridization Chain Reaction for Enhancing Detection of Individual Cytokine-Secreting Human Peripheral Mononuclear Cells. Analytical Chemistry 83 : 6890-6895 (Year: 2011).
Choi et ai., Programmable in situ amplification for multiplexed imaging of mRNA expression. Nature Biotechnology 28(11): 1208 (Year: 2010).
Choi, et al., Next-Generation in Situ Hybridization Chain Reaction: Higher Gain, Lower Cost, Greater Durability. ACS NANO 8.5 (May 2014): 4284-4294, XP055409053, US.
Choy et al. 2008. "Genetic analysis of human traits in vitro: drug response and gene expression in lymphoblasloid cell lines" PLoS Genet 4: e1000287. PMC ID: PMC2583954.
Chozinski, et al., Expansion microscopy with conventional antibodies and fluorescent proteins. Nature Methods. Jun. 2016; vol. 13, No. 6: pp. 485-491.
Christian et al. 2001. "Detection of DNA point mutations and mRNA expression levels by rolling circle amplification in individual cells" Proc Nall Acad Sci U SA 98: 14238-43. PMC ID: PMC64666.

Church et al. 2008. "High-Speed Imaging for DNA Sequencing" Biopholonics ( http:// NWW.pholonics.com/Conlenl/ReadArticle.aspx? ArticleID=33989).
Church et al.; Center for Casual Consequences of Variation {CCV) "An NHGRI Center for Excellence in Genomic Science" http://ccv.med.harvard.edu; Wayback Machine {Jul. 3, 2011).
Church et al.; Center for Casual Consequences of Variation {CCV) "Our four Specific Aims" http://ccv.med.harvard. edu/specific_aims.htm; Wayback Machine {Aug. 13, 2011).
Church GM. 2006. "Genomes for all" Sci Am 294: 46-54.
Church; "Proposal for a Center for the determination of the Causal Transcriptional Consequences of Human Genetic Variation (CTCHGV)" http://ccv.med.harvard.edu/CEGS09_Complete_Proposal_minus_Admin_Sections.09May21. final.pdf; Wayback Machine (Aug. 13, 2011).
Clausson et al., Compaction of rolling circle amplification products increases signal integrity and signal-to-noise ratio. Scientific Reports, vol. 5. Jul. 23, 2015. p. 12317.
Cong et al.: Multiplex genome engineering using CRISPR/Cas systems. Science 339(6121):819-823 (2013).
Conze et al. "Single molecule analysis of combinatorial splicing" Nucleic Acids Research, Jun. 29, 2010, vol. 38, No. 16; e163.
Cookson W, Liang L, Abecasis G, Moffatt M, Lathrop M. 2009. "Mapping complex disease traits with global gene expression" Nat Rev Genet 10: 184-94.
Co-pending U.S. Appl. No. 17/240,463, inventors Evan; R. Daugharthy et al., filed Apr. 26, 2021.
Co-pending U.S. Appl. No. 17/884,808, inventors Church; George M et al., filed Aug. 10, 2022.
Co-pending U.S. Appl. No. 17/944,276, inventor Church; George M., filed Sep. 14, 2022.
Co-pending U.S. Appl. No. 17/956,892, inventors Daugharthy; Evan R et al., filed Sep. 30, 2022.
Co-pending U.S. Appl. No. 18/064,956, inventors Church; George M et al., filed Dec. 13, 2022.
Co-pending U.S. Appl. No. 18/146,483, inventors Levner; Daniel et al., filed Dec. 27, 2022.
Co-pending U.S. Appl. No. 18/157,108, inventors Church; George M et al., filed Jan. 20, 2023.
CRISPR in the Lab: A Practical Guide [online]. Addgene. Sep. 4, 2014. Retrieved on Dec. 4, 2014. Retrieved from the Internet: URL: https://www.addgene.org/CRISPR/guide/.
Dasari, et al., Platform for Spatial Molecular Data by Vivek Dasari 1-7 Signature redacted Thesis Supervisor. (Aug. 2015) XP055559164, URL: http://dspace.mit.edu/bitstream/handle/1721.1/107103/971494098-MIT.pdf?sequence=1.
Davies et al. Crystal Structure of the ribonuclease H domain of HIV-1 Reverse Transcriptase.Science 252 :88 (Year: 1991).
De Bakker PI, Yelensky R, Pe'er I, Gabriel SB, Daly MJ, Altshuler D. 2005. "Efficiency and power in genetic associalior studies" Nat Genet 37: 1217-23.
Deng et al., Targeted bisulfite sequencing reveals changes in DNA methylation associated with nuclear reprogramming. Nat Biotechnol. 27 (4):353-360 (2009).
Dicarlo, et al. Genome engineering in Saccharomyces cerevisiae using CRISPR-Cas systems. Nucleic Acids Res. Apr. 2013;41(7):4336-43. doi: 10.1093/nar/gkt135. Epub Mar. 4, 2013.
Dirks et al., Triggered amplification by hybridization chain reaction, PNAS 101(43) : 15275 (Year: 2004).
Dixon et al. 2007. "A genome-wide association study of global gene expression" Nat Genet 39:1202-7.
Doillon, et al., Actin Filaments in Normal Dermis and During Wound Healing. The American Journal of Pathology 126.1 (1987): 164-170.
Duose, et al. Multiplexed and Reiterative Fluorescence Labeling via DNA Circuitry. Bioconjug Chem. Dec. 1, 20105; 21(12): 2327-2331.
Eberwine et al. 2001. "mRna expression analysis of tissue sections and single cells" J Neurosci 21: 8310-4.
Eid et al. 2009. "Real-time DNA sequencing from single polymerase molecules" Science 323: 133-8.

(56) References Cited

OTHER PUBLICATIONS

Eliscovich, et al., mRNA on the move: The road to its biological destiny. Journal of Biological Chemistry 288.28 (Jul. 2013): 20361-20368.
Emilsson et al. 2008; "Genetics of gene expression and its effect on disease" Nature 452: 423-8.
Femino et al. "Visualization of Single RNA Transcripts in Situ" Science, Apr. 24, 1998, vol. 280, pp. 585-590.
Fu et al. Improving CRISPR-Cas nuclease specificity using truncated guide RNAs. Nat Biotechnol 32(3):279-284 (2013).
Gao, et al., An Efficient strategy for sequencing-by-synthesis. Journal of Nanoscience and nanotechnology. 2010; 10:2988-2993.
Gasiunas et al. Cas9-crRNA ribonucleoprotein complex mediates specific DNA cleavage for adaptive immunity in bacteria. PNAS USA 109:E2579-E2586 (2012).
Gavrilovic et al. "Automated Classification of Multicolored Rolling Circle Products in Dual-Channel Wide-Field Fluorescence Microscopy" Cytometry Part A, Jul. 2011, 79(7), pp. 518-527.
Geiss, et al. Direct multiplexed measurement of gene expression with color-coded probe pairs. Nat Biotechnol. Mar. 2008;26(3):317-25. doi: 10.1038/nbt1385. Epub Feb. 17, 2008.
Gilbert et al., CRISPR-Mediated modular RNA-guided regulation of transcription in Eukaryotes. Cell 154(2): 442-451 (2013).
Ginart, et al., RNA Sequencing In Situ. Nat Biotechnol 32.6 (Jun. 2014): 543-544, DOI:10.1038/nbt.2921.
Goranson et al.: A single molecule array for digital targeted molecular analyses. Nucleic Acids Res. 37(1): e7:1-9 doi: 10.1093/nar/gkn921 (2009).
Grompe, The rapid detection of unknown mutations in nucleic acids. Nature Genetics (Oct. 1993): 111-117, DOI: 10.1038/ng1093-111.
Gunderson et al.: Decoding randomly ordered DNA arrays. Genome Research 14(5):870-877 (2004).
Guo et al. "Target-driven DNA association to initiate cyclic assembly of hairpins for biosensing and logic gate operation" Chemical Science, 2015, 6, pp. 4318-4323.
Gusev, et al., Rolling circle amplification: a new approach to increase sensitivity for immunohistochemistry and flow cytometry. Am J Pathol . Jul. 2001; 159(1):63-9. doi: 10.1016/S0002-9440(10)61674-4.
Hale et al., Essential Features and Rational Design of CRISPR RNAs That Function With the Cas RAMP Module Complex to Cleave RNAs, Molecular Cell, (20 12) vol. 45, Issue 3, 292-302.
Han, et al., Quantum-dot-tagged microbeads for multiplexed optical coding of biomolecules. Nature Biotechnology 19.99 (Jul. 2001): 631-635.
Hansen et al., Sensitive ligand-based protein quantification using immuno-PCR: A critical review of single-probe and proximity ligation assays. Biotechniques 56:217-228 (Year: 2014).
Harris et al. 2008. "Single-molecule DNA sequencing of a viral genome" Science 320: 106-9.
Hatoum-Aslan, et al. 'Mature clustered, regularly interspaced, short palindromic repeats RNA 5,9, 14 (crRNA) length is measured by a ruler mechanism anchored at the precursor processing site.' Proceedings of the National Academy of Sciences. vol. 108, No. 52. pp. 21218-21222. Dec. 2011. entire document.
Ho et al. "Sequencing by ligation variation with endonuclease V digestion and deoxyinosine-containing query oligonucleotides" BMC Genomics, 2011, 12:598.
International HapMap C. 2005. "A haplotype map of the human genome" Nature 437: 1299-1320. PMCID: PMC1880871.
Itzkovitz et al. "Single molecule transcript counting of stem cell markers in the mouse intestine" Nat Cell Biol., Nov. 2011, 14(1), pp. 106-114.
Itzkovitz et al., Validating transcripts with probes and imaging technology. Nat Methods. 8(4 Suppl):S12-9 (2011).
J. H. Lee, M.D. Ph.D. presentation entitled "Population-wide Tissue-specific Functional Analysis of Human iPS Cells Using Single-Cell In Situ Sequencing" George Church Laboratory, Wyss Institute for Biology Inspired Engineering, Harvard Medical School, Boston, Jan. 10, 2010.
Jambhekar, et al., Cis-acting Determinants of Asymmetric, Cytoplasmic RNA Transport. RNA 13 (2007): 625-642.
Jarvius et al. Digital quantification using amplified single-molecule detection. Nat Methods 3:725-727 (2006).
Jiang et al. "Solar thermal polymerase chain reaction for smartphone-assisted molecular diagnostics" Scientific Reports, 4:4137, 2014.
Jinek , et al. 'RNA-programmed genome editing in human cells.' eLite 2013;2:e00471 . [retrieved 1-3, 6, 7, 10-12 on Jun. 3, 2014). Retrieved from the Internet. URL: http://elife.elifesciences.org/content/2/e00471 . entire document.
Jinek et al. A programmable dual-RNA-guided DNA endonuclease in adaptive bacterial immunity. Science 337(6096):816-821 (2012).
Ju et al.: Four-Color DNA Sequencing by Synthesis Using Cleavable Fluorescent Nucleotide Reversible Terminators. PNAS USA 103:19635-19640 (2006).
Kalivas, et al., FamRCA-RACE: a Rolling Circle Amplification Race for Isolating a Family of Homologous CDNAS in One Reaction and Its Application to Obtain Nac Genes Transcription Factors From Crocus (Crocus sativus) Flower. Preparative Biochemistry and Biotechnology 40.3 (Jul. 2010): 177-187.
Ke et al., In situ sequencing for RNA analysis in preserved tissue and cells. Nature Methods 10(9): 857 (Year: 2013).
Kim JB, Porreca GJ, Song L, Greenway SC, Gorham JM, Church GM, Seidman CE, Seidman JG. 2007. "Polony multiplex analysis of gene expression {PMAGE) in mouse hypertrophic cardiomyopathy" Science 316: 1481-4.
Klein RJ. 2007. "Power analysis for genome-wide association studies" BMC Genet 8: 58. PMC ID: PMC2042984.
Kolb HC, Finn MG, B. SK. 2001. "Click Chemistry: Diverse Chemical Function from a Few Good Reactions" Angew.Chem. Int. 40: 2004-21.
Koller, et al., Mechanisms of single-stranded phosphorothioate modified antisense oligonucleotide accumulation in hepatocytes. Nucleic Acids Research, 2011, vol. 39, No. 11, 4795-4807.
Kotewicz et al., Isolation of MMuLV RT lacking RNase H activity. Nucleic Acids Research 16(1) :265 (Year: 1988).
Kuimelis et al., Cleavage properties of an oligonucleotide containing a bridged internucleotide 5-phosphorothioate RNA linkage. Nucleic Acids Research 23 (23) : 4753-4760 (Year: 1995).
Kurimoto et al. 2007. "Global single-cell cDNA amplification to provide a template for representative high-density oligonucleotide microarray analysis" Nat Protoc 2: 739-52.
Kuznetsova et al: "What Macromolecular Crowding Can Do to a Protein". Int.J.Mol. Sci .. vol. 15. No. 12. Dec. 1, 2014 (Dec. 1, 2014). pp. 23090-23140.
Kwan et al. 2008. "Genome-wide analysis of transcript isoform variation in humans" Nat Genet 40: 225-31.
Kwiatkowski et al. 1999. "Inversion of in situ synthesized oligonucleolides: improved reagents for hybridization and primer extension in DNA microarrays" Nucleic Acids Res 27: 1710-4. PMC ID: PMC148770.
Lagunavicius et al. "Novel application of Phi29 DNA polymerase: RNA detection and analysis in vitro and in situ by target RNA-primed RCA" RNA, May 2009, 15(5), pp. 765-771.
Larsson, et al., In situ detection and genotyping of individual mRNA molecules. Nature Methods, vol. 7, No. 5, Apr. 11, 2010. pp. 395-397.
Lee, et al., "Fluorescent in situ sequencing (FISSEQ) of RNA for gene expression profiling in intact cells and tissues" Nature Protocols (Feb. 12, 2015) 10(3):442-458. XP055272042, GB ISSN:1754-2189, DOI: 10.1038/nprot.2014.191.
Lee, et al., Highly Multiplexed Subcellular RNA Sequencing in Situ. Science 343.6177 (Mar. 2014): 1360-1363, doi: 10.1126/science.1250212.
Leman, AR et al. The Replication Fork: Understanding the Eukaryotic Replication Machinery and the Challenges to Genome Duplication. Genes. Jan. 29, 2013. vol. 4; pp. 1-32; figure 1; DOI: 10.3390/genes4010001.
Leuchowius, Karl-Johan et al. Parallel Visualization of Multiple Protein Complexes in Individual Cells in Tumor Tissue. The Ameri-

(56) References Cited

OTHER PUBLICATIONS can Society for Biochemistry and Molecular Biology, Inc. Molecular & Cellular Proteomics vol. 12, No. 6, pp. 1563-1571. Jun. 2013.
Levsky et al. "Fluorescence in situ hybridization: past, present and future" Journal of Cell Science, Jul. 15, 2003, 116 (Pt 14), pp. 2833-2838.
Levsky et al. "Single-Cell Gene Expression Profiling" Science, Aug. 2, 2002, 297(5582), pp. 836-840.
Li and Beaker. Kinetics of RNA Degradation by Specific Base Catalysis of Transesterification Involving the 2'-Hydroxyl Group. JACS 121 :5364 (Year: 1999).
Li et al. 2009. "Genome-wide Identification of Human RNA Editing Sites by Parallel DNA Capturing and Sequencing" Science in press.
Li et al. 2009. "Multiplex padlock capture and sequencing reveal human hypermulable CpG variations" Genome Res in press.
Lin et al., "CRISPR/Cas9 systems have off-target activity with insertions or deletions between target DNA and guide RNA sequences," Nucleic Acids Research, vol. 42, No. 11, pp. 7473-7485 (May 16, 2014).
Liu et al., Cell-Penetrating Peptide-Mediated Delivery of TALEN Proteins via Bioconjugation for Genome Engineering, PLOS ONE, 2014, vol. 9(1), pp. 1-7.
Lizardi, Next-generation sequencing-by-hybridization. Nature Biotechnology, vol. 26, No. 6, Jun. 2008, pp. 649-650.
Lubeck, Eric et al. Single Cell Systems Biology By Super-resolution Imaging and Combinatorial Labeling. Nature methods. vol. 9. No. 7 (2012): 743-748.
Lubeck et al., Single-cell in situ RNA profiling by sequential hybridization. Mar. 2014, Nature Methods vol. 11, No. 4, pp. 360-361.
Maeder, Morgan L., et al.," Robust, synergistic regulation of human gene expression using TALE activators," HHS Public Access Author Manuscript, vol. 10, No. 3, Feb. 10, 2013 (Feb. 10, 2013), pp. 243-245.
Mag et al. Synthesis and selective cleavage of an oligodeoxynucleotide containing a bridged internucleotide 5'-phosphorothioate linkage. Nucleic Acids Res. 19, 7 (1991): 1437-1441.
Maierhofer et al. "Multicolor Deconvolution Microscopy of Thick Biological Specimens" American Journal of Pathology, vol. 162, No. 2, Feb. 2003, pp. 373-379.
Makarova, et al. Evolution and classification of the CRISPR-Cas systems. Nat Rev Microbiol. Jun. 2011;9(6):467-77. doi: 10.1038/nrmicro2577. Epub May 9, 2011.
Mali et al., RNA-Guided Human Genome Engineering via Cas9. Science, 339 (Feb. 15, 2013): 823-826.
Mali, P. et al. CAS9 Transcriptional Activators for Target Specificity Screening and Paired Nickases for Cooperative Genome Engineering. Nature Biotechnology. Aug. 1, 2013. vol. 31; pp. 833-838; entire document. DOI: 10.1038/nbt.2675.
Mali, P. et al. RNA-Guided Human Genome Engineering via Cas9. Science. Jan. 3, 2013, vol. 339; pp. 823-826; abstract; p. 823, second column, second to third paragraph; p. 823, third column, second paragraph to third paragraph; figure 1; Supplementary material, p. 4, first paragraph; p. 7, first paragraph; Supplementary figures S1, S3. DOI: 10.1126/science.1232033.
Manders, et al. Direct imaging of DNA in living cells reveals the dynamics of chromosome formation. The Journal of cell biology. Mar. 8, 1999;144(5):813-822.
Marblestone, et al., Rosetta Brains: A strategy for molecularly-annotated connectomics. arXiv, Apr. 2014; 1-18.
Markaki et al. "Fluorescence In Situ Hybridization Applications for Super-Resolution 3D Structured Illumination Microscopy" Methods in Molecular Biology, Jan. 2013, vol. 950, pp. 43-64.
Mathews, CK., Biochemistry of deoxyribonucleic acid-defective amber mutants of bacteriophage T4. Journal of Biological Chemistry 243(21) :5610-5615. (Year: 1968).
Matlin, et al., Spatial Expression of the Genome: the Signal Hypothesis at Forty. Nature Reviews. Molecular Cell Biology 12.5 (May 2011): 333-340.
Mccarroll SA. 2008. "Extending genome-wide association studies to copy-number variation" Hum Mol Genet 17: R135-42.
Meade et al. "Multiplexed DNA detection using spectrally encoded porous" Analytical Chemistry, Apr. 1, 2009, 81(7), pp. 2618-2625.
Meeks, et al., Characterization of Genes Encoding Poly(a) Polymerases in Plants: Evidence for Duplication and Functional Specialization. Plos One 4.11 (Nov. 2009): e8082.
Mei, et al., A comprehensive review and performance evaluation of bioinformatics tools for HLA class I peptide-binding prediction. Briefings in bioinformatics, 00(00), 2019, 1-17.
Meng Q, Kim DH, Bai X, Bi L, Turro NJ, Ju J_ 2006. "Design and synthesis of a photocleavable fluorescent nucleotide 3'-O-allyl-dGTP-PC-Bodipy-FL-510 as a reversible terminator for DNA sequencing by synthesis" J Org Chem 71: 3248-52.
Mignardi et al. "Fourth-generation sequencing in the cell and the clinic" Genome Medicine, 2014, 6:31.
Mitra et al. 2003. "Digital genotyping and haplotyping with polymerase colonies" Proc Nall Acad Sci US A 100: 5926-31. PMC ID: PMC156303.
Mitra et al. 2003. "Fluorescent in situ sequencing on Jolymerase colonies" Anal Biochem 320: 55-65.
Mitra et al.: In situ localized amplification and contact replication of many individual DNA molecules. Nucleic Acids Res. 27(24): e34 (1999).
Monika S Rutowska et al: "Integration of a 30 hydrogel matrix with a hollow core photonic crystal fibre for DNA probe immobilization", Measurement Science and Technology, IOP, Bristol, GB, vol. 21, No. 9, Jul. 28, 2010 (Jul. 28, 2010), p. 94016, XP020197365,ISSN: 0957-0233, DOI: 10.1088/0957-0233/21 /9/094016.
Morley M, Molony CM, Weber TM, Devlin JL, Ewens KG, Spielman RS, Cheung VG. 2004. "Genetic analysis of Genome-wide variation in human gene expression" Nature 430: 743-7.
Muller et al. Towards unlimited colors for fluorescence in-situ hybridization (FISH). Chromosome Research. 10:223-232, 2002.
Nadji et ai., "Photochemically and Photoenzymatically Cleavable Dna," J. Am. Chern. Soc. 1992, 114, 9266-9269.
Nair, S. et al., Natural Killer T cells in cancer immunotherapy. Front. Immunol. Sep. 2017; 8(1178): 1-18.
Ng L et al: "Surface-based mapping of gene expression and probabilistic expression maps in the mouse cortex", Methods, Academic Press, NL, vol. 50, No. 2, Feb. 1, 2010 (Feb. 1, 2010), pp. 55-62, XP026857255, ISSN: 1 046-2023.
Nguyen, Son C.: "Strategies for Studying Chromatin Regulation and Organization", May 1, 2018 (May 1, 2018). XP055684323. Retrieved from the Internet: URL: https://dash.harvard.edu/bitstream/handle/1/33493431/NGUYEN-DISSERTATION-2016.pdf?sequence=4&isAllowed=y [retrieved on Arp. 8, 2020].
Nikolakakis, K. et al., Use of Hybridization Chain Reaction-Fluorescent In Situ Hybridization to Track Gene Expression by Both Partners during Initiation of Symbiosis. Appl Environ Microbiol . Jul. 2015;81(14):4728-35. doi: 10.1128/AEM.00890-15. Epub May 8, 2015.
Nuovo. Co-labeling using in Situ PCR: A Review. Journal of Histochemistry & Cytochemistry. vol. 49, Issue. 11 (2001): pp. 1329-1339.
Ohata et al., "Confocal Imaging Analysis of Intracellular Ions in Mixed Cellular Systems or in Situ Using Two Types of Confocal Microscopic Systems," Methods in Enzymology, vol. 307, pp. 425-441 (1999), particularly p. 437.
Oupicky David et al: "Laterally stabilized complexes of DNA with linear reducible polycations: Strategy for triggered intracellular activation of DNA delivery vectors". Journal of the American Chemical Society. American Chemical Society. US. vol. 124. No. 1. Jan. 9, 2002 (Jan. 9, 2002). pp. 8-9.
Pan et al. 2008. "A procedure for highly specific, sensitive, and unbiased whole-genome amplification" Proc Nall Acad Sci US A 105: 15499-504. PMC ID:PMC2563063.
Parinov et al. "DNA sequencing by hybridization to microchip octa- and decanucleotides extended by stacked pentanucleotides" Nucleic Acids Research, 1996, vol. 24, No. 15, pp. 2998-3004.
Perez-Pinera, Pablo, et al., "Synergistic and tunable human gene activation by combinations of synthetic transcription factors," Nature Methods, vol. 10. No. 3, Feb. 3, 2013 (Feb. 3, 2013), pp. 239-242.

(56) References Cited

OTHER PUBLICATIONS

Philipp Spuhler et al: "Precise control of DNA orientation for improved functionality in protein binding microarrays", Optical MEMS and Nanophotonics (OMN), 2011 Internationalconference on, IEEE, Aug. 8, 2011 (Aug. 8, 2011), pp. 91-92,XP031968753,DOI: 10.1109/0MEMS.2011.6031084ISBN: 978-1-4577-0334-8.
PI: Piezo Nano Positioning, 2008 (online), retrieved on Aug. 12, 2020, pp. 1-6 https://www.pi-usa.us/fileadmin/user_upload/pi_us/files/product_datasheets/N725_Piezo_Focus_Positioner.pdf.
Pihlak, et al. Rapid genome sequencing with short universal tiling probes. Nature Biotechnology, 26: 676-684 (2008).
Pjanic et al. "Nuclear Factor I genomic binding associates with chromatin boundaries," BMC Genomics, Feb. 12, 2013 {Dec. 2, 2013}, vol. 14, No. 99, pp. 1-18. entire document.
Polidoros, et al., Rolling circle amplification—RACE: A method for simultaneous isolation of 5' and 3' cDNA ends from amplified cDNA templates. BioTechniques 41.1 (Jul. 2006):35-42. including p. 1/1 of Supplementary Material.
Porreca et al. 2006. "Polony DNA sequencing" Curr Protoc Mol Biol Chapter 7: Unit 7.8; Supplement 76: 22 Pages.
Porreca, et al., Multiplex amplification of large sets of human exons. Nature Methods. 2007. 4: 931-6.
Qi et al. Repurposing CRISPR as an RNA-guided platform for sequence-specific control of gene expression. Cell 152:1173-1183 (2013).
Raj et al. Imaging individual mRNA molecules using multiple singly labeled probes. Nature Methods 5(10):877-879 (2008).
Ramakrishna et al. Gene disruption by cell-penetrating peptide-mediated delivery of Cas9 protein and guide RNA. Genome Research 24:1020-1027 (2014).
Ran et al. Double Nicking by RNA-Guided CRISPR Cas9 for Enhanced Genome Editing Specificity. Cell 154(6):1380-1389 (2013).
Ravan, et al., Isothermal RNA Detection Through the Formation of DNA Concatemers Containing HRP-mimicking DNAzymes on the Surface of Gold Nanoparticles. Biosensors and Bioelectronics 80 (Jan. 2016): 67-73.XP029441324.
Rho, Mina et al. 'Diverse CRISPRs Evolving in Human Microbiomes.' PLoS Genetics. vol. 8, No. 6. 1-14 pp. 1-12. Jun. 2012. entire document.
Richardson et al., Experimental and Theoretical Studies of Light-to-Heat Conversion and Collective Heating Effects in Metal Nanoparticle Solutions. Nano Letters 9(3) : 1139-1146 (Year: 2009).
Risch N, Merikangas K. 1996. "The future of genetic studies of complex human diseases" Science 273: 1516-7.
Sachidanandam et al. 2001. "A map of human genome sequence variation containing 1.42 million single nucleotide polymorphisms" Nature 409: 928-33.
Saliba, et al., Single-cell RNA-Seq: Advances and Future Challenges. Nucleic Acids Research 42.14 (2014): 8845-8860, DOI: 10.1093/nar/gku555.
Sano, et al. Immuno-PCR: Very sensitive antigen detection by means of specific antibody-DNA conjugates. Science. 258 (1992): 120-122.
Sapranauskas et al. The Streptococcus thermophilus CRISPR/Cas system provides immunity in *Escherichia coli*. Nucleic Acid Res. 39:9275-9282 (2011).
Schadt et al. 2003. "Genetics of gene expression surveyed in maize, mouse and man" Nature 422: 297-302.
Schadt et al. 2008. Mapping the genetic architecture of gene expression in human liver PLoS Biol 6: e107. PMC ID: PMC2365981.
Schouten et al., "Relative quantification of 40 nucleic acid sequences by multiplex ligation-dependent probe amplification," Nucleic Acids Research, 30(12):e57, 2002.
Schweitzer et al. Immunoassays with rolling circle DNA amplification: a versatile platform for ultrasensitive antigen detection. Proceedings of the National Academy of Sciences. USA. 97(18) (Aug. 2000):10113-10119.
Seo, et al. Four-color DNA sequencing by synthesis on a chip using photocleavable fluorescent nucleotides. Proceeding of the National Academy of Sciences USA. 102.17 (Apr. 2005): 5926-5931.
Serre et al. 2008. "Differential allelic expression in the human genome: a robust approach to identify genetic and epigenetic cis-acting mechanisms regulating gene expression" PLoS Genet 4: e1000006. PMC ID: PMC2265535.
Shendure et al. 2004. "Advanced sequencing technologies: methods and goals" Nat Rev Genet 5: 335-44.
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE. 1117839.
Shendure JA, Porreca GJ, Church GM. 2008. "Overview of DNA sequencing strategies" Curr Protec Mol Biol Chapter 7: Unit 7.1; Supplement 81: 11 Pages.
Singer-Kruger, et al., Here, There, Everywhere. RNA Biology 11.8 (Aug. 2014): 1031-1039.
Soderberg, et al., Direct Observation of Individual Endogenous Protein Complexes in Situ by Proximity Ligation. Nature Methods 3.12 (Dec. 2006): 995-1000.
Song et al., Hybridization chain reaction-based aptameric system for the highly selective and sensitive detection of protein. Analyst 137: 1396 (Year: 2012).
Sontheimer et al., "Project 7: Establishing RNA-Directed DNA Targeting in Eukaryotic Cells; Project dates: Nov. 16, 2011 to Dec. 31, 2012" (Feb. 4, 2012).
Srinivas et al., On the biophysics and kinetics of toehold-mediated DNA strand displacement. Nucleic Acids Research 41 (22) : 10641-10658 (Year: 2013).
Starnes et al., Human immunodeficiency virus reverse transcriptase-associated RNase H Activity. J. of Biological Chemistry 264(12) : 7073-7077 (Year: 1989).
Stougaard et al. 2007. "In situ detection of non-polyadenylated RNA molecules using Turtle Probes and target primed rolling circle PRINS" BMC Biotechnol 7: 69. PMC ID: PMC2203993.
Sun et al. "Composite Organic-Inorganic Nanoparticles as Raman Labels for Tissue Analysis" Nano Letters, Feb. 2007, vol. 7, No. 2, pp. 351-356.
Supplemental Material for Schweitzer et al. (PNAS 2000; 97(18):10113-10119) (Year: 2000).
Szolek, A et al. OptiType: precision HLA typing from next-generation sequencing data, Bioinformatics. Dec. 1, 2014; 30(23): 3310-3316. Published online Aug. 20, 2014.
Tam et al. A Microfluidic Platform for Correlative Live-Cell and Super-Resolution Microscopy. PloS one. Dec. 29, 2014;9(12):e115512, pp. 1-20.
Tan, et al., MicroRNA9 regulates neural stem cell differentiation by controlling Hes1 expression dynamics in the developing brain. Genes to Cells. Dec. 2012; vol. 17, Issue 12: 952-961.
Tang et al. 2009. "mRNA-Seq whole-transcriptome analysis of a single cell" Nat Methods 6: 377-82.
Terry R, Porreca G, McCarthy K, Church GM. 2008. Polonator Instrument http://www.polonator.org ; Wayback Machine(Aug. 7, 2008) "Software".
Terry R, Porreca G, McCarthy K, Church GM. 2008. Polonator Instrument http://www.polonator.org; Wayback Machine (Sep. 5, 2008) "PET {Paired End-Tag} Genomic Shotgun Library Construction Protocol".
Terry R, Porreca G, McCarthy K, Church GM. 2008. Polonator Instrument http://www.polonator.org; Wayback Machine(Aug. 7, 2008) "Flow Cells".
Terry R, Porreca G, McCarthy K, Church GM. 2008. Polonator Instrument http://www.polonator.org; Wayback Machine(Aug. 7, 2008) "Instrument Overview".
Terry R, Porreca G, McCarthy K, Church GM. 2008. Polonator Instrument http://www.polonator.org; Wayback MachineAug. 7, 2008) "Open, Affordable, Sequencing".
Terry R, Porreca G, McCarthy K, Church GM. 2008. Polonator Instrument http://www.polonator.org; Wayback Machine(Aug. 7, 2008) "Protocols".
Terry R, Porreca G, McCarthy K, Church GM. 2008. Polonator Instrument http://www.polonator.org; Wayback Machine(Aug. 7, 2008) "Reagent Kits".

(56) References Cited

OTHER PUBLICATIONS

Terry R, Porreca G, McCarthy K, Church GM. 2008. Polonator Instrument http://www.polonator.org; Wayback Machine(Aug. 7, 2008) "The Polonator Ecosystem".
Terry R, Porreca G, McCarthy K, Church GM. 2008. Polonator Instrument http://www.polonator.org; Wayback Machine(Aug. 7, 2008) "The Vision".
Terry R, Porreca G, McCarthy K, Church GM. 2008. Polonator Instrument http://www.polonator.org; Wayback Machine(Jul. 5, 2008) "Polony Sequence Protocols".
Terry R, Porreca G, McCarthy K, Church GM. 2008. Polonator Instrument http://www.polonator.org; Wayback Machine(Sep. 5, 2008) "Bead Capping Protocol".
Terry R, Porreca G, McCarthy K, Church GM. 2008. Polonator Instrument http://www.polonator.org; Wayback Machine(Sep. 5, 2008) "Bead Enrichment Protocol".
Terry R, Porreca G, McCarthy K, Church GM. 2008. Polonator Instrument http://www.polonator.org; Wayback Machine(Sep. 5, 2008) "Coverslip Aminosilanation and Arraying Protocol".
Terry R, Porreca G, McCarthy K, Church GM. 2008. Polonator Instrument http://www.polonator.org; Wayback Machine(Sep. 5, 2008) "Emulsion Breaking Protocol".
Terry R, Porreca G, McCarthy K, Church GM. 2008. Polonator Instrument http://www.polonator.org; Wayback Machine(Sep. 5, 2008) "Emulsion PCR Protocol".
Terry R, Porreca G, McCarthy K, Church GM. 2008. Polonator Instrument http://www.polonator.org; Wayback Machine(Sep. 5, 2008) "Emulsion PCR/Bead Capping Kits".
Terry R, Porreca G, McCarthy K, Church GM. 2008. Polonator Instrument http://www.polonator.org; Wayback Machine(Sep. 5, 2008) "Enrichment Kits".
Terry R, Porreca G, McCarthy K, Church GM. 2008. Polonator Instrument http://www.polonator.org; Wayback Machine(Sep. 5, 2008) "Help Wanted".
Terry R, Porreca G, McCarthy K, Church GM. 2008. Polonator Instrument http://www.polonator.org; Wayback Machine(Sep. 5, 2008) "Paired-Leg Library Kits".
Terry R, Porreca G, McCarthy K, Church GM. 2008. Polonator Instrument http://www.polonator.org; Wayback Machine(Sep. 5, 2008) "Polony Sequence by Ligation Protocol".
Terry R, Porreca G, McCarthy K, Church GM. 2008. Polonator Instrument http://www.polonator.org; Wayback Machine(Sep. 5, 2008) "Run Kits".
The Delivery Problem, Nature Biotechnology, 2006, vol. 24(3), pp. 305-306.
Thisse et al., High-resolution in Situ Hybridization to Whole-mount Zebrafish Embryos. Nature Protocols 3.1 (2008): 59-69, Doi:10.1038/nprot.2007.514.
Tiley, LS et al. The VP16 Transcription Activation Domain Is Functional When Targeted to a Promoter-Proximal RNA Sequence. Genes and Development. 1992. vol. 6; pp. 2077-2087; abstract; p. 2077, first column first paragraph.
Tillberg, et al., Protein-retention expansion microscopy of cells and tissues labeled using standard fluorescent proteins and antibodies. Nat Biotechnol . Sep. 2016;34(9):987-92. doi: 10.1038/nbt.3625. Epub Jul. 4, 2016.
Trafton, A. Editing The Genome With High Precision [online]. MIT News office. Jan. 3, 2013 [retrieved on Dec. 4, 2014]. Retrieved from the Internet: URL: https://news.mit.edu/2013/editing-the-genome-with-high-precision-0103 ;pp. 1-3; p. 3, third paragraph.
Tsaflaris, et al., Isolation of Three Homologous AP1-like MADS-box Genes in Crocus (*Crocus sativus* L.) and Characterization of Their Expression. Plant Science 166.5 (May 2004): 1235-1243.
Vigneault F, Sismour AM, Church GM. 2008." Efficient microRNA capture and bar-coding via enzymatic oligonucleotide adenylation" Nat Methods 5: 777-9.
Wang, et al., Rapid and Sensitive detection of severe acute respiratory syndrome coronavirus by rolling circle amplification, 2005,43, 2339-2344.

Wang, et al. RNA-Seq: a revolutionary tool for transcriptomics. Nature Reviews Genetics, 10: 57-63 (2009).
Wang et al., "The method of axial drift compensation of laser differential confocal microscopy based on zero-tracking," Proc. of SPIE, vol. 9618, 96180X (2015).
Weibrecht, et al., Simultaneous Visualization of Both Signaling Cascade Activity and End-Point Gene Expression in Single Cells, PLOS ONE. vol. 6. No. 5, May 25, 2011. p. e20148.
Weis, et al., Protein Targeting to Subcellular Organelles via mRNA Localization. Biochimica et Biophysica Acta 1833 available online (Apr. 2012): 260-273.
Wählby, Carolina et al. Sequential Immunofluorescence Staining and Image Analysis for Detection of Large Numbers of Antigens in Individual Cell Nuclei. Communications in clinical cytometry. vol. 47. No. 1 (2002): 32-41.
Wiedenheft et al. RNA-guided genetic silencing systems in bacteria and archaea. Nature 482:331-338 (2012).
Wilson et al. "Encoded Microcarriers for High-Throughput Multiplexed Detection" Angewandte Chemie International Edition, Sep. 18, 2006, 45(37), pp. 6104-6117.
Wright et al., "Dynamic closed-loop system for focus tracking using a spatial light modulator and a deformable membrane mirror," Optics Express, vol. 14, No. 1, pp. 222-228 (Jan. 9, 2006).
Wu et al.., "3'-o-modified Nucleotides as Reversible Terminators for Pyrosequencing," PNA, 2007, vol. 104(42), pp. 16462-16467.
Xiao et al., "Single-step Electronic Detection of Femtomolar DNA by Target-induced Strand Displacement in an Electrode-bound Duplex," PNAS, 2006, vol. 103(45), pp. 16677-16680.
Yamaguchi et al. "eDNA display: a novel screening method for functional disulfide-rich peptides by solid-phase synthesis and stabilization of mRNA-protein fusions," Nucleic Acids Research, Jun. 15, 2009 {Jun. 15, 2009), vol. 37, No. 16, e108 {p. 1-13 for citations). entire document.
Zhang et al., "Digital RNA Allelotyping Reveals Tissue-specific and Allele-specific Gene Expression in Human," Nat Methods., Aug. 2009, vol. 6(8), pp. 613-618.
Zhang et al., Dynamic DNA nanotechnology using strand-displacement reactions. Nature Chemistry 3 : 103-113 (Year: 2011).
Zhang et al., "Sequencing Genomes From Single Cells by Polymerase Cloning," Nature Biotechnology, 2006, vol. 24(6), pp. 680-686.
Zhang et al., "Long-range Polony Haplotyping of Individual Human Chromosome Molecules," Nature Genetics, Mar. 2006; vol. 38(3), pp. 382-387, doi: 10.1038/ng1741.
Zhao et al. "Advances of multiplex and high throughput biomolecular detection technologies based on encoding microparticles" Science China Chemistry, Aug. 2011, vol. 54, No. 8, pp. 1185-1201.
Zhao et al., An electrochemical aptasensor based on hybridization chain reaction with enzyme-signal amplification for interferon-gamma detection. Biosensors and Bioelectronics 36: 129-134 (Year: 2012).
Zhou, et al., In Situ detection of Messenger RNA using digoxiogenin-labeled oligonucleotides and rolling circle amplification. Experimental and molecular Pathology, 2001; 70: 281-288.
Nakano et al. Effects of Molecular Crowding on the Structures, Interactions, and Functions of Nucleic Acids. Chem. Rev. 2014, 114, 5, 2733-2758.
Bottari et al. Application of FISH technology for microbiological analysis: current state and prospects. Appl Microbiol Biotechnol Dec. 2006; 73(3):485-94.
Donaldson, Julie G. Unit 4.3 Immunofluorescence Staining. Curr Protoc Cell Biol May 2001; 04; Unit 4.3. 9 pages.
Duose, et al. Configuring robust DNA strand displacement reactions for in situ molecular analyses. Nucleic Acids Res. Apr. 2012; 40(7): 3289-3298.
Duose et al. Supporting Information to: Configuring robust DNA strand displacement reactions for in situ molecular analyses. 2012. 5 pages.
Duose et al. Supporting Information to: Multiplexed and Reiterative Fluorescence Labeling via DNA Circuitry. Bioconjugate Chem 2010. 4 pages.

(56) References Cited

OTHER PUBLICATIONS

Feature Analysis of Claim 1 from Opposition to European Patent No. EP4108782B1 filed by NanoString Technologies Inc., dated Jul. 18, 2023. 1 page.

Goransson et al. Supplementary Data to: A Single Molecule Array for Digital Targeted Molecular Analyses. Nucleic Acids Research, vol. 37, Issue 1, 2009. 5 pages.

Gunderson, et al. Decoding Randomly Ordered DNA Arrays. Genome Res. 14:870-877, 2004.

Henegariu et al. Colour-changing karyotyping: an alternative to M-FISH/SKY. Nature Genetics 23, 263-264 (1999).

Huang et al., Super-resolution fluorescence microscopy, Annu Rev Biochem. 2009 ;78: 993-1016, First published: Apr. 2, 2009.

"Hybridisation". Extract from Oxford Dictionary of Biochemistry and Molecular Biology, Second Edition, 2006. 4 pages.

Olejnik et al. Photocleavable aminotag phosphoramidites for 5'-termini DNA/RNA labeling. Nucleic Acids Research, 1998, vol. 26, No. 15, 3572-3576.

Opposition to European Patent No. EP4108782B1 filed by NanoString Technologies Inc., dated Jul. 18, 2023. 83 pages.

"Probe". Extract from Oxford Dictionary of Biochemistry and Molecular Biology, Second Edition, 2006. 4 pages.

Schubert et al. Analyzing proteome topology and function by automated multidimensional fluorescence microscopy. Nature Biotechnology, 2006. 9 pages.

Söderberg, O. et al., "Characterizing proteins and their interactions in cells and tissues using the in situ proximity ligation assay," Methods, 2008;45(3):227-32.

Stryer et al. Biochemistry, Fifth Edition. pp. 124-125. 2002.

U.S. Appl. No. 61/579,265, inventors Levner; Daniel et al., filed Dec. 22, 2011.

Veccham et al. A Non-perturbative pairwise-additive analysis of charge transfer contributions to intermolecular interaction energies. Physical Chemistry Chemical Physics, 2020. 48 pages.

Zhen, et al. Poly-FISH: a technique of repeated hybridizations that improves cytogenetic analysis of fetal cells in maternal blood. Prenat Diagn. 1998; 18(11):1181-5.

Abramoff, et al. Image processing with ImageJ. Biophotonics international 11(7):36-42 (2003).

Bioptechs, FCS2 (Focht Live-Cell Chamber System) Instructions (2007): 1-6. Retrieved on URL: http://www.bioptechs.com/Instructions/FCS2_i/fcs2-3_i.htm.

Brileya, et al. Biofilm growth mode promotes maximum carrying capacity and community stability during product inhibition syntrophy. Front Microbiol. 5:693, 1-14 (2014).

Bui, et al. Analytical Devices Based on Light-emitting Diodes—a Review of the State-of-the-art. Analytica Chimica Acta 853:46-58 (2015).

Chirieleison, et al. Automated live cell imaging systems reveal dynamic cell behavior. Biotechnol Prog. 27(4):913-924 (2011).

Delaune, et al. Single-cell-resolution Imaging of the Impact of Notch Signaling and Mitosis on Segmentation Clock Dynamics. Developmental Cell 23(5):995-1005 (2012).

Ehrlicher, et al. Optical neuronal guidance. Methods Cell Biol. 83:495-520 (2007).

Fang-Yen, et al. Video-rate tomographic phase microscopy. J Biomed Opt. 16(1):011005-1-011005-5 (2011).

Femino, et al. Visualization of single molecules of mRNA in situ. Methods Enzymol. 361:245-304 (2003).

Fischer, et al. Microscopy in 3D: a Biologist's Toolbox. Trends in Cell Biology 21(12):682-691 (2011).

FluoSpheres™ Carboxylate-Modified Microspheres. Thermo Fischer Scientific. Retrieved from: https://www.thermofisher.com/order/catalog/product/F8809. (2024).

Gerhardt, et al. Detection of single molecules illuminated by a light-emitting diode. Sensors (Basel). 11(1):905-916 (2011).

Hamilton, HVXM 8-5 Valve Laboratory Products. Retrieved from URL on Mar. 7, 2024: https://www.hamiltoncompany.com/laboratoryproducts/valves/36766.

Harvard Apparatus, PHD 22/2000 Syringe Pump Series User's Manual:1-62 (1996).

Hattori, et al. Single-molecule Imaging With an Inexpensive UV-LED Light Source. Chemistry letters 38(3): 234-235 (2009).

Hodneland, et al. CellSegm—a MATLAB toolbox for high-throughput 3D cell segmentation. Source Code Biol Med. 8(1):16, 1-24 (2013).

James, Paul, Water Objectives A Personal Exploration . . . all is Not What It Seems. Microscopy UK 1-8 (2004). Retrieved from URL: http://www.microscopy-uk.org.uk/mag/indexmag.html? http://www.microscopy-uk.org.uk/mag/artoct04/pjwater.html.

Kuo, et al. High-power blue/UV light-emitting diodes as excitation sources for sensitive detection. Electrophoresis. 25(21-22):3796-37804 (2004).

Moffitt, et al. RNA Imaging with Multiplexed Error-Robust Fluorescence In Situ Hybridization (MERFISH). Methods in Enzymology 572:1-49 (2016).

Nikon MicroscopyU, Culture Chambers for Live-Cell Imaging, Retrieved from: https://web.archive.org/web/20150810165805/http://www.microscopyu.com:80/articles/livecellimaging/culturechambers.html. (2015).

Niman, et al. Controlled microfluidic switching in arbitrary time-sequences with low drag. Lab Chip. 13(12):2389-2396 (2013).

North, et al. Seeing is believing? A beginners' guide to practical pitfalls in image acquisition. J Cell Biol. 172(1):9-18 (2006).

O'Connor, Clare. Fluorescence In Situ Hybridization (FISH). Nature Education 1(1) (2008). Retrieved from URL: https://www.nature.com/scitable/topicpage/fluorescence-in-situ-hybridization-fish-327.

Olympus Lifescience, Instructions IX71/IX51 Inverted Research Microscope/Inverted Basic Microscope, (2005) at https://www.ucc.ie/en/media/academic/anatomy/imagingcentre/icdocuments/OLYMPUSIX71_manual.pdf.

Olympus Lifescience, Inverted Research System Microscopes IX71/IX81 IX2 Series Manual Olympus IX-71 (2009). Retrieved from: https://afns-labs.ualberta.ca/wp-content/uploads/sites/58/2018/05/Olympus-IX81-brochure.pdf.pdf.

Olympus Lifescience. Research Inverted System Microscope IX71/IX81 IX2 Series (2005), Retrieved from: https://www.olympus-lifescience.com/data/olympusmicro/brochures/pdfs/ix71.pdf?rev=EABE.

Perillo, et al. Enhanced 3D Localization of Individual RNA Transcripts via Astigmatic Imaging. Single Molecule Spectroscopy and Superresolution Imaging VII. SPIE 8950:895003-1-895003-11 (2014).

Querido, et al. Using fluorescent proteins to study mRNA trafficking in living cells. Methods Cell Biol. 85:273-292 (2008).

Richard, et al. Cellular mechanisms by which lipoic acid confers protection during the early stages of cerebral ischemia: a possible role for calcium. Neurosci Res. 69(4):299-307 (2011).

Sands, et al. Automated Imaging of Extended Tissue Volumes Using Confocal Microscopy. Microscopy Research and Technique 67(5):227-239 (2005).

Schneider, Caroline, et al. NIH Image to ImageJ: 25 Years of Image Analysis. Nature Methods. vol. 9, Issue No. 7 (2012): 671-675.

Shah, et al. Dynamics and Spatial Genomics of the Nascent Transcriptome by Intron seqFISH. Cell. 174(2):363-376 (2018).

Shen, et al. Digital Autofocus Methods for Automated Microscopy. Methods in Enzymology 414:620-632 (2006).

Sivaramakrishnan, et al. Shear stress induced reorganization of the keratin intermediate filament network requires phosphorylation by protein kinase C zeta. Mol Biol Cell. 20(11):2755-2765 (2009).

Skafte-Pedersen, et al. A Self-contained, Programmable Microfluidic Cell Culture System With Real-time Microscopy Access. Biomedical Microdevices 14(2):385-399 (2012).

Spector, et al. Observation of Live Cells in the Light Microscope. Cells a Laboratory Manual vol. 2: Light Microscopy and Cell Structure. Cold Spring Harbor Laboratory Press: 75.1-75.13 (1998).

Thermo Fischer Scientific, Fluorescence SpectraViewer, Retrieved on Feb. 29, 2024, from: https://www.thermofisher.com/order/fluorescence-spectraviewer/#!/.

Tirichine, Leïla, et al. 3D Fluorescent in Situ Hybridization Using *Arabidopsis* Leaf Cryosections and Isolated Nuclei. Plant Methods. vol. 5, Article 11 (2009): 1-7.

(56) References Cited

OTHER PUBLICATIONS

Toomre, et al. A new wave of cellular imaging. Annu Rev Cell Dev Biol. 26:285-314 (2010).
U.S. Pat. No. 11,542,554—*Nanostring Technologies, Inc.* (Petitioner) v. *President and Fellows of Harvard College.* Petition for Inter Partes Review dated Jan. 30, 2024.
U.S. Appl. No. 17/395,534 Notice of Allowance dated Jun. 21, 2022.
U.S. Appl. No. 17/395,534 Office Action dated Mar. 4, 2022.
Wessels, et al. Light-emitting diodes in modern microscopy—from David to Goliath? Cytometry A. 81(3):188-197 (2012).
Winer, et al. Application of a three-dimensional (3D) particle tracking method to microfluidic particle focusing. Lab Chip. 14(8):1443-1451 (2014).
Xiao, et al. Single-molecule Imaging in Live Cells. Handbook of Single-Molecule Biophysics. 43-93 (2009).
Zessin, et al. A Hydrophilic Gel Matrix for Single-molecule Super-resolution Microscopy. Optical Nanoscopy. 2(4):1-8 (2013).

\* cited by examiner

Called HLA-A: **A*01_01 + A*02_01**

```
A*01_01   GCGCCGTGGATAGAGCAGGAGGCCCGGAGTATTGGGACCAGGAGACACGGAATATG
A*02_01   GCGCCGTGGATAGAGCAGGAGGTCCGGAGTATTGGGACGGGAGACACGGAAAGTG
A*03_01   GCGCCGTGGATAGAGCAGGAGGCCCGGAGTATTGGGACCAGGAGACACGGAATGTG
A*24_02   GCGCCGTGGATAGAGCAGGAGGCCCGGAGTATTGGGACGGGAGACAGGAAAGTG
cons      *********************   **************   ******  ***  **
```

Position unique to A*02:01 among these alleles.

Position not unique to either allele but distinguishes A*01:01 from A*02:01

FIG. 2

| HLA Gene + Allele | Sequence Variation | | | | | | Frequency in U.S. Population |
|---|---|---|---|---|---|---|---|
| | 1 | 15 | 16-18 | 22-24 | 57 | 68 | |
| x HLA-A*02:01 | T | T | CCAC | TAC | A | C | 41% |
| + HLA-A*03:01 | T | T | CCAC | GAC | C | C | 20% |
| ▫ HLA-B*13:02 | C | C | TAAC | TTA | C | C | 4% |
| * HLA-B*35:03 | C | C | TGAC | TTC | C | C | 5% |
| HLA-C*04:01 | C | T | TAAC | TTC | C | T | 24% |
| HLA-C*06:02 | C | T | TGAC | TCC | C | C | 13% |

△ CD3E, CD4, CD8A, CD8B – T-Cell Markers

METHODS AND SYSTEMS FOR SPATIAL MAPPING OF GENETIC VARIANTS

CROSS-REFERENCE

This application is a Continuation of U.S. application Ser. No. 17/403,405, filed Aug. 16, 2021, which claims the benefit of U.S. Provisional Application No. 63/066,604, filed Aug. 17, 2020.

The instant application contains a Sequence Listing which has been submitted electronically in XML format and is hereby incorporated by reference in its entirety. Said XML copy, created on Aug. 2, 2023, is named 52160-731_301_SL.xml and is 4,452 bytes in size.

BACKGROUND

Cancer immunotherapies utilize immune cells to detect and eliminate cancerous cells from the body. Immune cells often identify cancerous cells due to the presentation of tumor antigens on the cancer cell surface by major histocompatibility complex (MHC) proteins. In some instances, the efficacy of a cancer immunotherapy can be dependent on the expression of particular antigens and/or MHC proteins by cancerous cells. Antigens and MHC proteins can be expressed heterogeneously within a tumor volume leading to the presence of a single tumor with several clonal populations of cancer cells. Cancer treatments targeting clonal populations expressed throughout the volume of a tumor may improve treatment efficacy.

SUMMARY

Recognized herein is a need to spatially map the expression of antigens/major histocompatibility complex (MHC) proteins. The methods and compositions provided herein can inform the selection of cancer immunotherapies that are more likely to be effective for a particular patient.

In an aspect, the present disclosure provides a method of analyzing a spatial distribution of a first human leukocyte antigen (HLA) variant sequence in a biological sample comprising: (a) obtaining a biological sample comprising a nucleic acid corresponding to the first HLA variant sequence from a subject; (b) hybridizing a first probe comprising an HLA targeting sequence to the nucleic acid corresponding to the first HLA variant sequence; (c) identifying at least a portion of the first probe; and (d) determining a location of the first HLA variant sequence within the biological sample by determining a location of the first probe.

In some embodiments, identifying at least a portion of the first probe comprises sequencing at least a portion of the first probe in situ. In some embodiments, determining a location of the first probe comprises sequencing at least a portion of the first probe in situ. In some embodiments, determining a location of the first HLA variant sequence further comprises identifying the first HLA variant sequence. In some embodiments, the first HLA variant sequence comprises an HLA allele. In some embodiments, identifying the first HLA variant sequence comprises identifying the first probe. In some embodiments, the method further comprises providing the biological sample within a three-dimensional (3D) matrix that preserves spatial information of the first HLA variant sequence prior to operations (c) and (d). In some embodiments, providing the biological sample within the 3D matrix comprises generating the 3D matrix. In some embodiments, the method further comprises immobilizing the first probe on the 3D matrix. In some embodiments, the method further comprises immobilizing the nucleic acid corresponding to the first HLA variant sequence on the 3D matrix. In some embodiments, the biological sample is provided within the 3D matrix by directing a precursor of the 3D matrix through the biological sample and subjecting the precursor of the 3D matrix to a reaction to generate cross-links and form the 3D matrix. In some embodiments, the cross-links comprise chemical crosslinks. In some embodiments, the cross-links comprise physical crosslinks. In some embodiments, the reaction comprises free-radical polymerization. In some embodiments, the reaction comprises a chemical conjugation reaction. In some embodiments, the reaction comprises a bioconjugation reaction. In some embodiments, the reaction comprises a photopolymerization reaction.

In some embodiments, the biological sample comprises a second nucleic acid corresponding to a second variant sequence and the method further comprises: (A) hybridizing a second probe comprising a second nucleic acid targeting sequence to the second nucleic acid corresponding to the second variant sequence; (B) identifying at least a portion of the second probe; and (C) determining a location of the second variant sequence within the biological sample by determining a location of the second probe. In some embodiments, the second variant sequence comprises a mutation. In some embodiments, the mutation is associated with an increased risk of cancer. In some embodiments, the mutation is associated with a tumor antigen. In some embodiments, the mutation is associated with a cancer/testis antigen. In some embodiments, the mutation is associated with an oncofetal protein. In some embodiments, the mutation is a tumor mutation. In some embodiments, the mutation is associated with a tumor suppressor protein. In some embodiments, the mutation is associated with a neoantigen. In some embodiments, the method further comprises generating a visual representation of the location of the first HLA variant sequence and the location of the second variant sequence for display on a graphical user interface (GUI). In some embodiments, the method further comprises detecting a clone within the biological sample by comparing the location of the first HLA variant sequence and the location of the second variant sequence. In some embodiments, the method further comprises generating a visual representation of a location of the clone within the biological sample for display on a graphical user interface (GUI). In some embodiments, the method further comprises identifying a cell or derivative thereof within the biological sample, wherein the cell derivative thereof comprises the first HLA variant sequence and the second variant sequence. In some embodiments, the method further comprises predicting the presentation of a peptide on a major histocompatibility complex (MHC) protein expressed in the biological sample, wherein the peptide is at least partially encoded by the second variant sequence and the MHC protein is at least partially encoded by the HLA variant sequence. In some embodiments, the peptide is a mutant peptide. In some embodiments, the peptide is associated with an increased risk of cancer. In some embodiments, the method further comprises selecting a treatment to be administered to the subject, wherein: the treatment comprises administration of a cell to the subject; and the cell comprises a cell receptor that recognizes the peptide on the MHC protein expressed in the biological sample. In some embodiments, the cell is a T-cell, a B cell, or a natural killer T (NKT) cell. In some embodiments, the cell is a recombinant T-cell. In some embodiments, the cell expresses a chimeric antigen receptor. In some embodiments, the cell expresses a recombinant T cell receptor. In some embodiments, the method further comprises selecting a treatment to be administered to the subject, wherein the treatment is more likely to be effective in a subject with one or more cancer cells presenting the peptide on the MHC protein expressed in the biological sample than it is in a subject without the one or more cancer cells that present the peptide on the MHC protein expressed in the biological sample. In some embodiments, the treatment is an immunotherapy. In some embodiments, the treatment comprises administration of a checkpoint inhibitor to the subject. In some embodiments, the method further comprises selecting a treatment to be administered to the subject, wherein: the treatment comprises administration of the peptide; and the treatment is more likely to be effective in a subject with one or more cancer cells expressing the MHC protein expressed in the biological sample than it is in a subject without one or more cancer cells that express the MHC protein. In some embodiments, the biological sample further comprises a third nucleic acid, and wherein the third nucleic acid corresponds to a second HLA variant sequence, the method further comprising: (1) hybridizing a third probe comprising a second HLA targeting sequence to the third nucleic acid; (2) identifying at least a portion of the third probe; and (3) determining a location of the second HLA variant sequence within the biological sample by determining a location of the third probe. In some embodiments, a plurality of additional probes (e.g., fourth, fifth, sixth, etc.) are used to detect various genes encoding antigens, inflammatory markers, or cell typing markers within a biological sample, such as a panel of genes for assaying expression of antigens, inflammatory markers, or cell typing markers.

In some embodiments, the method further comprises, prior to operation (b): (I) obtaining a genetic profile of the subject; (II) detecting a presence or absence of a first HLA allele in the subject by analyzing the genetic profile. In some embodiments, the first HLA variant sequence comprises the first HLA allele detected in the genetic profile. In some embodiments, the first HLA allele comprises a mutation. In some embodiments, the first HLA allele is a gene variant. In some embodiments, the method further comprises identifying a first group of HLA alleles, wherein the first group of HLA alleles are expressed in the biological sample, and wherein the first probe is designed to hybridize to a nucleic acid corresponding to one of the HLA alleles of the first group of alleles. In some embodiments, the first probe discriminates between two alleles of the first group of HLA alleles.

In some embodiments, the method further comprises, prior to operation (b): (I) obtaining a genetic profile of the subject; (II) detecting a plurality of HLA alleles in the subject by analyzing the genetic profile; wherein the first probe preferentially hybridizes to a nucleic acid corresponding to only one of the HLA alleles detected in the genetic profile. In some embodiments, the genetic profile is generated via ribonucleic acid (RNA) sequencing. In some embodiments, the genetic profile is generated via exome sequencing. In some embodiments, the first HLA variant sequence is a class I HLA allele. In some embodiments, the first HLA variant sequence is a class II HLA allele. In some embodiments, the first HLA variant sequence is HLA-A*01:01. In some embodiments, the first HLA variant sequence is HLA-A*02:01. In some embodiments, the first HLA variant sequence is HLA-B*44:02. In some embodiments, the first HLA variant sequence is HLA-C*07:01. In some embodiments, the first HLA variant sequence is HLA-C*08:02. In some embodiments, the first HLA variant sequence is HLA-DPA1. In some embodiments, the first HLA variant sequence is HLA-DPB1*01. In some embodiments, the first HLA variant sequence is HLA-DQA1. In some embodiments, the first HLA variant sequence is HLA-DQB1. In some embodiments, the first HLA variant sequence is HLA DRB1. In some embodiments, the first HLA variant sequence is HLA-DRA. In some embodiments, the nucleic acid corresponding to the first HLA variant sequence is a deoxyribonucleic acid (DNA) molecule. In some embodiments, the nucleic acid corresponding to the first HLA variant sequence is an RNA molecule. In some embodiments, the method further comprises, prior to operation (b), reverse transcribing RNA expressed in the biological sample to form complementary deoxyribonucleic acid (cDNA), wherein the cDNA comprises the nucleic acid corresponding to the first HLA variant sequence. In some embodiments, the biological sample is a tissue biopsy. In some embodiments, the biological sample is a tumor biopsy. In some embodiments, the biological sample is biological tissue. In some embodiments, the biological sample is a surgical resection. In some embodiments, the biological sample is a tumor. In some embodiments, the biological sample is a blood sample.

In some embodiments, the method further comprises, prior to operation (b), generating a section, wherein the section comprises a portion of the biological sample. In some embodiments, the method further comprises, prior to operation (c) subjecting the first probe to an amplification reaction to generate an amplified nucleic acid molecule that corresponds to the first HLA variant sequence. In some embodiments, identifying at least a portion of the first probe comprises identifying at least a portion of the amplified nucleic acid molecule. In some embodiments, determining the location of the first probe comprises determining a location of the amplified nucleic acid molecule. In some embodiments, the method further comprises, prior to operation (c) subjecting the first probe to an amplification reaction to generate an amplified nucleic acid molecule that corresponds to the first HLA variant sequence and immobilizing the amplified nucleic acid molecule on the 3D matrix. In some embodiments, the first probe is a circularizable probe. In some embodiments, the circularizable probe is a padlock probe. In some embodiments, the padlock probe comprises: a first end; a second end; a 5' terminal region; and a 3' terminal region; and wherein the 5' terminal region and the 3' terminal region hybridize to the nucleic acid corresponding to the first HLA variant sequence. In some embodiments, the method further comprises circularizing the padlock probe by ligating the first end and the second end of the padlock probe together, thereby generating a circularized padlock probe. In some embodiments, the first end and the second end are in contiguous. In some embodiments, the first end and the second end are separated by a gap region containing at least one nucleotide. In some embodiments, the gap region contains from 2 to 500 nucleotides. In some embodiments, the method further comprises filling the gap region by incorporating at least one nucleotide in an extension reaction. In some embodiments, the amplification reaction is a rolling circle amplification (RCA) reaction. In some embodiments: the nucleic acid corresponding to the first HLA variant sequence is a DNA molecule hybridized to an RNA molecule; the nucleic acid corresponding to the first HLA variant sequence comprises a first sequence; the RNA molecule comprises a second sequence; the first sequence is the reverse complement of the second sequence; the method further comprises, prior to (b); (i) degrading or digesting at least a portion of the RNA molecule; and the second sequence is identified based on the identification of at least a portion of the amplified nucleic acid sequence. In some embodiments, the DNA molecule is a cDNA molecule. In some embodiments, the biological sample is present in a 3D matrix; and the DNA molecule is immobilized to the 3D matrix. In some embodiments, the biological sample is present in a 3D matrix; and the first probe is immobilized to the 3D matrix. In some embodiments, the method further comprises administering a treatment to the subject, wherein the treatment is selected for administration to the subject based at least partially on the spatial distribution of the first HLA variant sequence in the biological sample. In some embodiments, the treatment comprises an immunotherapy. In some embodiments, the treatment comprises a checkpoint inhibitor. In some embodiments, the treatment comprises a cancer vaccine. In some embodiments, the treatment comprises a chimeric antigen receptor T-cell therapy. In some embodiments, the treatment comprises a recombinant T-cell therapy.

In another aspect, the present disclosure provides a method of identifying a location of a human leukocyte antigen (HLA) allele in a biological sample comprising targeting a nucleobase to a nucleic acid molecule encoding the HLA allele in the biological sample and identifying a sequence of the nucleic acid molecule or derivative thereof in situ to identify the location of the HLA allele within the biological sample.

In another aspect, the present disclosure provides a method of identifying a location of a human leukocyte antigen (HLA) allele in a biological sample comprising targeting a nucleic acid probe molecule to a nucleic acid molecule encoding the HLA allele in the biological sample and identifying a sequence of the nucleic acid molecule or derivative thereof in situ to identify the location of the HLA allele within the biological sample.

In another aspect, the present disclosure provides a method for analyzing a spatial distribution of a human leukocyte antigen (HLA) variant sequence in a biological sample from a subject, comprising (a) obtaining a genetic profile of the subject and detecting a presence or absence of the HLA variant sequence in the subject by analyzing the genetic profile; (b) hybridizing a first probe comprising an HLA targeting sequence to a first nucleic acid in the biological sample corresponding to the HLA variant sequence; (c) identifying at least a portion of the first probe; and (d) determining a location of the HLA variant sequence within the biological sample by determining a location of the first probe, wherein the first probe preferentially hybridizes to the first nucleic acid corresponding to the HLA variant sequence detected in the genetic profile. In some embodiments, the genetic profile is generated via RNA sequencing. In some embodiments, the genetic profile is generated via exome sequencing. In some embodiments, the biological sample comprises a second nucleic acid and the method further comprises hybridizing a second probe comprising another nucleic acid targeting sequence to the second nucleic acid, identifying at least a portion of the second probe; and determining a location of the second nucleic acid within the biological sample by determining a location of the second probe.

In another aspect, the present disclosure provides a method of analyzing a biological sample, comprising (a) obtaining the biological sample comprising a first nucleic acid and a second nucleic acid, wherein the first nucleic acid corresponds to an HLA variant sequence from a subject; (b) hybridizing a first probe comprising an HLA targeting sequence to the first nucleic acid corresponding to the HLA variant sequence and hybridizing a second probe comprising another nucleic acid targeting sequence to the second nucleic acid; (c) identifying at least a portion of the first probe and at least a portion of the second probe; and (d) determining a location of the HLA variant sequence and a location of the second nucleic acid within the biological sample.

In some embodiments, the second nucleic acid corresponds to an additional HLA variant sequence. In some embodiments, the second nucleic acid comprises a mutation. In some embodiments, the mutation is associated with an increased risk of cancer. In some embodiments, the mutation is associated with a cancer/testis antigen. In some embodiments, the mutation is associated with an oncofetal protein. In some embodiments, the mutation is a tumor mutation. In some embodiments, the mutation is associated with a tumor suppressor protein. In some embodiments, the mutation is associated with a neoantigen.

In some embodiments, the second nucleic acid is associated with a tumor antigen. In some embodiments, the second nucleic acid is associated with a marker of inflammation. In some embodiments, the second nucleic acid is associated with a marker for cell typing. In some embodiments, the second nucleic acid is associated with a marker for an immune cell or a cancer cell. In some embodiments, the method further comprises generating a visual representation of the location of the HLA variant sequence and the location of the second nucleic acid for display on a graphical user interface (GUI). In some embodiments, the method further comprises detecting a clone within the biological sample by comparing the location of the HLA variant sequence and a location of the additional HLA variant sequence. In some embodiments, the method further comprises generating a visual representation of a location of the clone within the biological sample for display on a graphical user interface (GUI). In some embodiments, the method further comprises identifying a cell or derivative thereof within the biological sample, wherein the cell derivative thereof comprises the HLA variant sequence and the second nucleic acid. In some embodiments, the method further comprises predicting the presentation of a peptide on a major histocompatibility complex (MHC) protein expressed in the biological sample, wherein the peptide is at least partially encoded by the second nucleic acid and the MHC protein is at least partially encoded by the HLA variant sequence.

In some embodiments, the peptide is a mutant peptide. In some embodiments, the peptide is associated with an increased risk of cancer. In some embodiments, identifying at least a portion of the first probe comprises sequencing at least a portion of the first probe in situ. In some embodiments, determining a location of the first probe comprises sequencing at least a portion of the first probe in situ. In some embodiments, determining a location of the HLA variant sequence further comprises identifying the HLA variant sequence. In some embodiments, the HLA variant sequence comprises an HLA allele. In some embodiments, the additional HLA variant sequence comprises an HLA allele. In some embodiments, identifying the HLA variant sequence comprises identifying the first probe.

In some embodiments, the method further comprises providing the biological sample within a three-dimensional (3D) matrix that preserves spatial information of the HLA variant sequence prior to operation (b). In some embodiments, providing the biological sample within the 3D matrix comprises generating the 3D matrix. In some embodiments, the method further comprises immobilizing the first probe on the 3D matrix. In some embodiments, the method further comprises immobilizing the first nucleic acid on the 3D matrix. In some embodiments, the biological sample is provided within the 3D matrix by directing a precursor of the 3D matrix through the biological sample and subjecting the precursor of the 3D matrix to a reaction to generate cross-links and form the 3D matrix. In some embodiments, the cross-links comprise chemical crosslinks. In some embodiments, the cross-links comprise physical crosslinks. In some embodiments, the reaction comprises free-radical polymerization. In some embodiments, the reaction comprises a chemical conjugation reaction. In some embodiments, the reaction comprises a bioconjugation reaction. In some embodiments, the reaction comprises a photopolymerization reaction.

In some embodiments, the HLA variant sequence is a class I HLA allele. In some embodiments, the HLA variant sequence is a class II HLA allele. In some embodiments, the HLA variant sequence is HLA-A*01:01. In some embodiments, the HLA variant sequence is HLA-A*02:01. In some embodiments, the HLA variant sequence is HLA-B*44:02. In some embodiments, the HLA variant sequence is HLA-C*07:01. In some embodiments, the HLA variant sequence is HLA-C*08:02. In some embodiments, the HLA variant sequence is HLA-DPA1. In some embodiments, the HLA variant sequence is HLA-DPB1*01. In some embodiments, the HLA variant sequence is HLA-DQA1. In some embodiments, the HLA variant sequence is HLA-DQB1. In some embodiments, the HLA variant sequence is HLA DRB1. In some embodiments, the HLA variant sequence is HLA-DRA. In some embodiments, the first nucleic acid corresponding to the HLA variant sequence is a DNA molecule. In some embodiments, the first nucleic acid corresponding to the HLA variant sequence is an RNA molecule. In some embodiments, the second nucleic acid is a DNA molecule. In some embodiments, the second nucleic acid is an RNA molecule.

In some embodiments, the biological sample is a tissue biopsy. In some embodiments, the biological sample is a tumor biopsy. In some embodiments, the biological sample is biological tissue. In some embodiments, the biological sample is a surgical resection. In some embodiments, the biological sample is a tumor. In some embodiments, the biological sample is a blood sample. In some embodiments, the method further comprises, prior to hybridizing the first probe, generating a section, wherein the section comprises a portion of the biological sample. In some embodiments, the method further comprises, prior to identifying the at least a portion of the first probe, subjecting the first probe to an amplification reaction to generate an amplified nucleic acid molecule that corresponds to the HLA variant sequence. In some embodiments, identifying the at least a portion of the first probe comprises identifying at least a portion of the amplified nucleic acid molecule. In some embodiments, determining the location of the first probe comprises determining a location of the amplified nucleic acid molecule. In some embodiments, the method further comprises, subjecting the first probe to an amplification reaction to generate an amplified nucleic acid molecule that corresponds to the HLA variant sequence. In some embodiments, the first probe is a circularizable probe. In some embodiments, the circularizable probe is a padlock probe. In some embodiments, the padlock probe comprises: a first end, a second end, a 5' terminal region, and a 3' terminal region. In some embodiments, the 5' terminal region and the 3' terminal region hybridize to the first nucleic acid corresponding to the HLA variant sequence.

In some embodiments, the method further comprises circularizing the padlock probe by ligating the first end and the second end of the padlock probe together, thereby generating a circularized padlock probe. In some embodiments, the first end and the second end are contiguous. In some embodiments, the first end and the second end are separated by a gap region containing at least one nucleotide. In some embodiments, the method further comprises filling the gap region by incorporating at least one nucleotide in an extension reaction. In some embodiments, the amplification reaction is a rolling circle amplification (RCA) reaction. In some embodiments, the method further comprises contacting the biological sample with a plurality of fluorescently label oligonucleotides directly or indirectly to identify at least a portion of the first probe. In some embodiments, the method further comprises contacting the biological sample with a plurality of fluorescently label oligonucleotides directly or indirectly to identify at least a portion of the second probe.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2 shows an example of designing a probe to focus on the discrimination of two different human leukocyte antigen (HLA) alleles known to be present in a sample. FIG. 2 discloses sequences A*01_01 (SEQ ID NO: 1), A*02_01 (SEQ ID NO: 2), A*03_01 (SEQ ID NO: 3), and A*24_02 (SEQ ID NO: 4).

Figure 3:
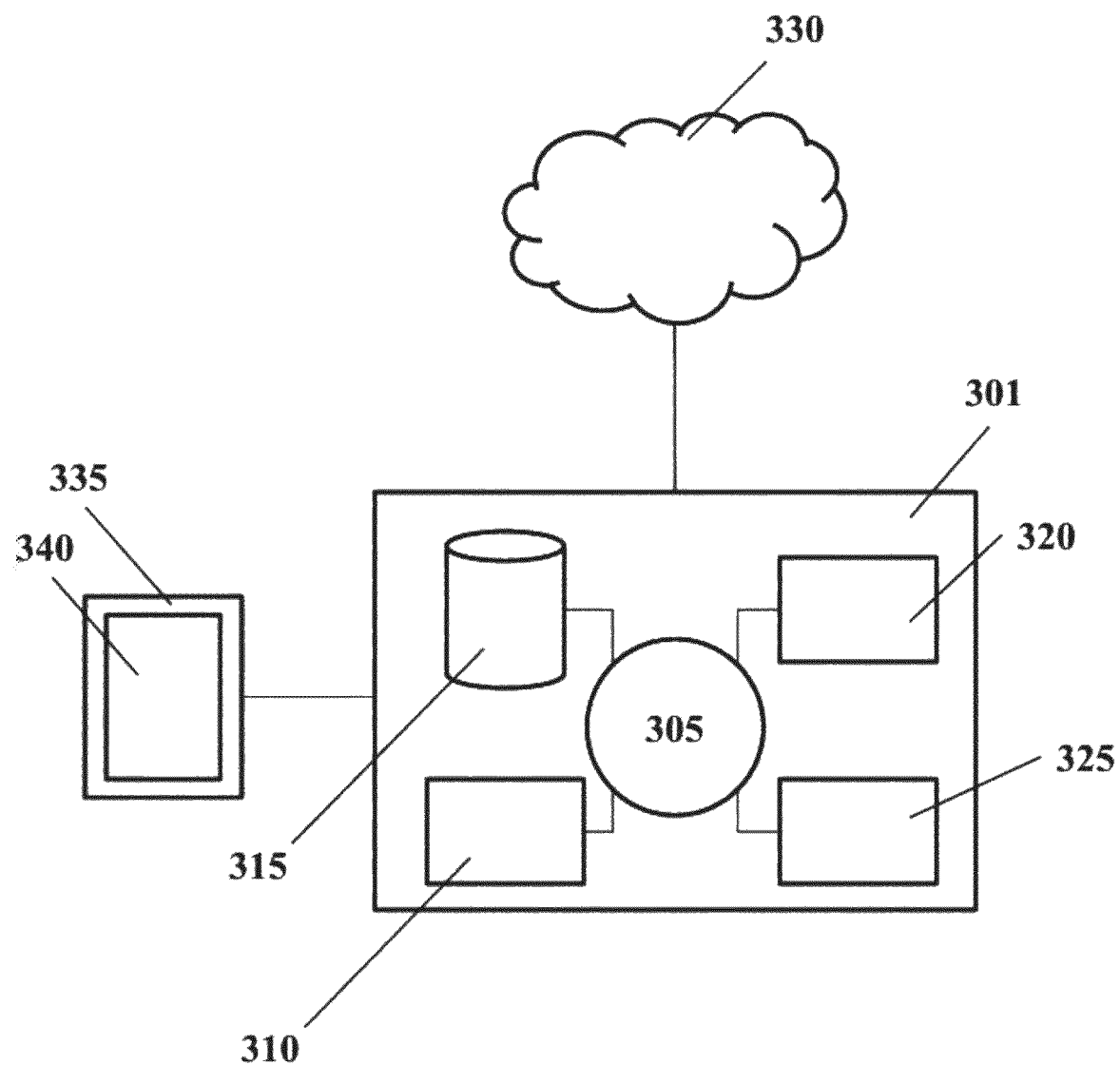

FIG. 3 shows a computer system that is programmed or otherwise configured to implement methods provided herein.

Figure 4:
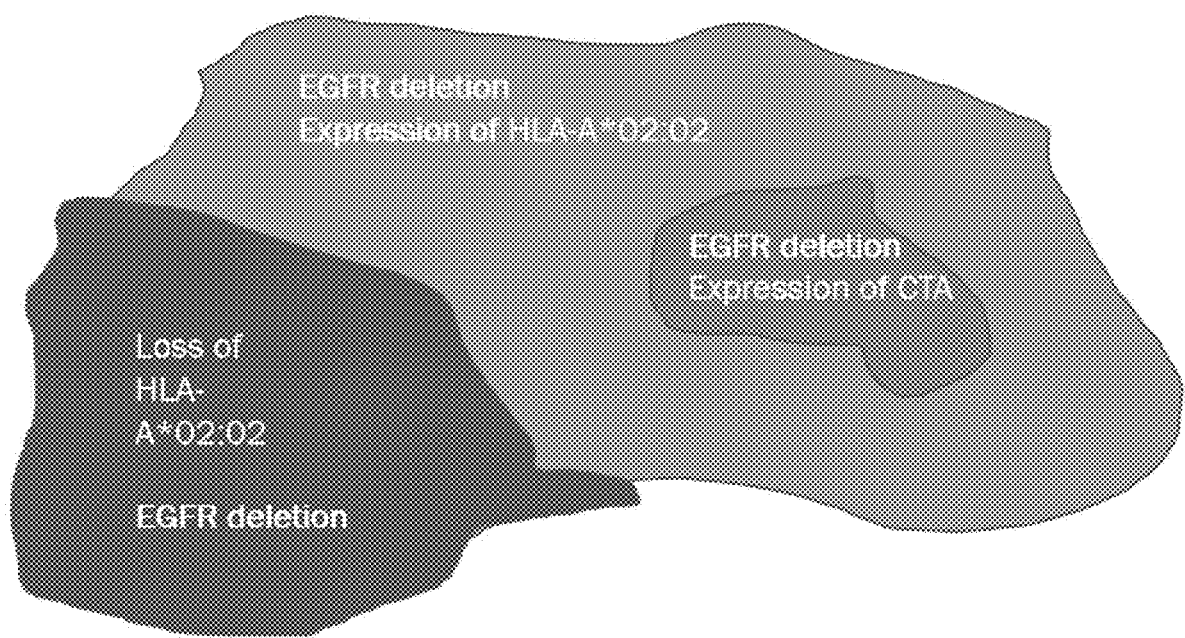

FIG. 4 shows a schematic of a spatial map of gene expression in a biological sample.

Figures 5A, 5B:
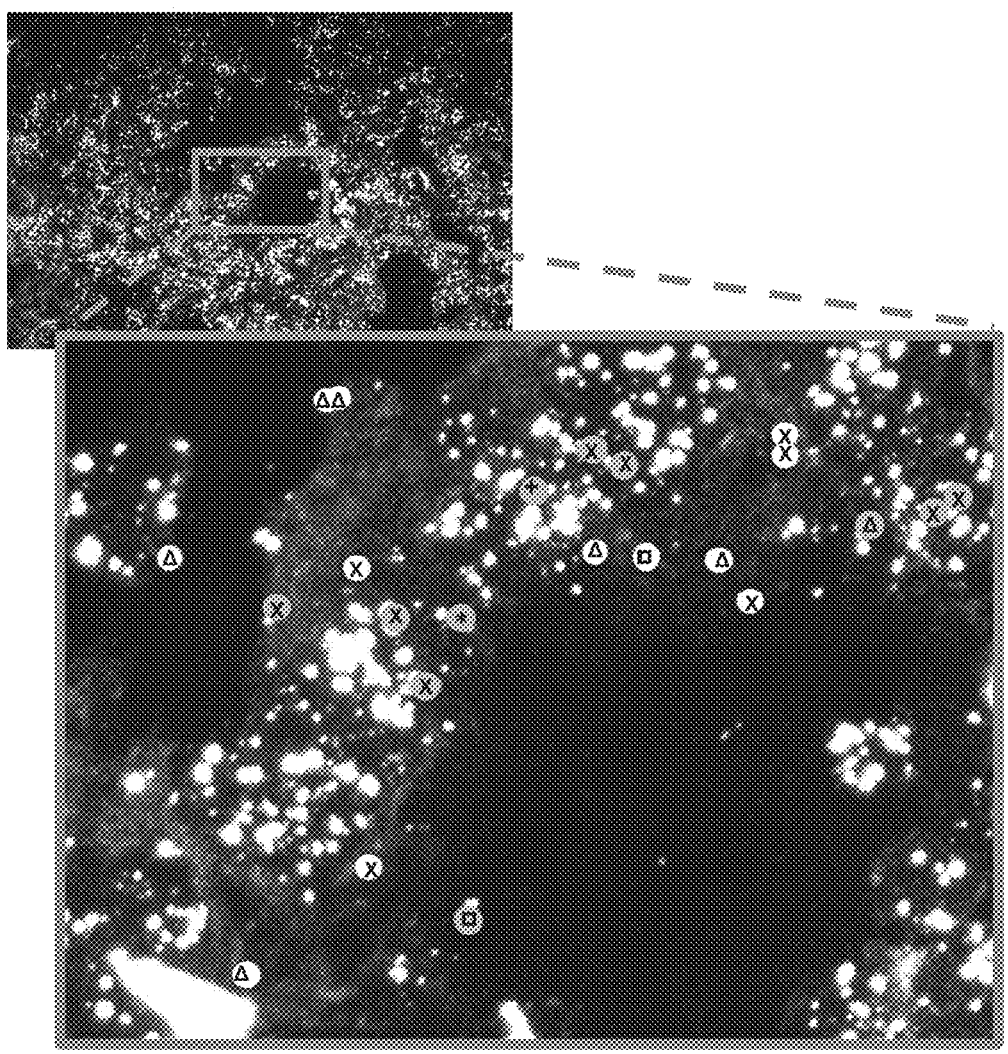

FIG. 5A-5B shows various HLA gene alleles and T cell markers detected in a biological sample.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Provided herein are methods and systems for spatially mapping genetic variants in a biological sample, such as a tumor or derivative thereof. Methods and systems of the disclosure can, for example, identify the presence or absence of clonal populations within a tumor by spatially mapping the expression of tumor antigens and major histocompatibility complex (MHC) proteins. MHC proteins are encoded by human leukocyte antigen (HLA) genes. HLA genes are highly polymorphic and many HLA variants exist, including alleles. Also disclosed are methods of selecting a treatment for cancer based on the spatial expression of HLA variants and/or tumor antigens and the use of such treatments as cancer therapies.

Treatment of cancer via immunotherapies offers many advantages over other chemotherapeutic-based approaches. However, the efficacy of a cancer immunotherapy can be dependent on the expression of particular tumor antigens and/or MHC proteins by cancerous cells. Antigens such as tumor antigens bind to MHC proteins to form MHC-antigen complexes which are presented on the cancer cell surface, where antigens can be recognized by immune cells. Within and between subjects, the antigen profiles of cells vary. The proper presentation of peptides on the surface of cells by MHC proteins allows the immune system to distinguish between cancerous cells and normal cells not to be harmed. In some instances, cancerous cells form in a subject that expresses tumor antigens. Non-limiting examples of tumor antigens include tumor specific antigens, (antigens only present on tumor cells), tumor-associated antigens (antigens present on tumor cells and some normal cells), and neoantigens (antigens not previously recognized by the immune system that can arise from altered tumor proteins formed as a result of tumor mutations or from viral proteins). In some instances, immune cells can detect the expression of tumor antigens and facilitate the destruction of cancerous cells displaying the tumor antigen.

For the effective detection of cancerous cells by immune cells, particular MHC proteins and antigens may be co-expressed by the cancerous cells. Over time, mutations in cancer cells can result in the loss or alteration of the expression of an antigen or its presenting MHC proteins, resulting in the formation of a tumor sub-clone. The loss of antigen expression in cancer cells, the mutation of antigens in cancer cells, the loss of MHC protein expression, or mutations to MHC proteins can allow cancerous cells to evade immune detection. Immunotherapies frequently rely on the detection of cancerous cells by immune cells, thus the loss or mutation of antigen expression in cancer cells or loss or mutations of MHC proteins can render an immunotherapy ineffective against a clonal population of cancer cells. In some instances, a clonal population of cancer cells can be expressed in a portion of a tumor, rather than throughout the volume of a tumor.

Some methods of selecting an immunotherapy based on antigen and/or MHC expression rely on analyzing gene expression data of tumors. However, these methods do not provide spatial information or identify the presence of clonal populations within tumors. Thus, the methods may improperly assume that a particular antigen and MHC molecule are both co-expressed in the same cell when they are not. Treatments selected based on such methods may be effective against clonal populations present in a small fraction of the tumor volume and may therefore have limited efficacy. A method that can spatially assess the expression of antigen and/or MHC proteins throughout a tumor can allow for the selection of a treatment or treatments aimed against clonal populations identified to be present in the tumor. Such clonal populations can be present in part of the tumor or throughout the volume of a tumor. In some cases, the clonal populations may be resistant to other therapies or may have evaded immune detection. Thus, the methods can allow for more targeted therapy selection. Treatments directed towards clonal populations identified in a tumor may have improved efficacy compared to those selected based on global tumor expression data directed towards unexpressed clonal populations or clonal populations expressed in only part of a tumor.

Methods and systems disclosed herein can overcome many of the shortcomings of some methods for immunotherapy selection. By utilizing probes that can identify and locate HLA gene variants and genes encoding antigen proteins within a biological sample, the methods and systems can spatially map clonal populations of cancer cells throughout a tumor. In some embodiments, probes can be used to identify and locate gene variants, genes encoding antigens, inflammatory markers, or cell typing markers within a biological sample. In some cases, the methods and systems can be used to detect presence or absence of, mutations of, or level of expression of gene variants and/or genes encoding antigens, inflammatory markers, or cell typing markers (e.g., immune cell marker, cancer marker) within a biological sample. In some cases, the biological samples comprise tumor tissue or a derivative thereof containing a three-dimensional matrix (3D) that preserves the spatial information of nucleic acid molecules corresponding to MHC proteins and/or tumor antigens. In some cases, loss of antigens and/or MHC protein expression may be detected. In some cases, biological samples are bodily fluids, such as blood, that preserve the cellular structure of nucleic acid molecules corresponding to MHC proteins and/or tumor antigens. In some embodiments, the methods provided herein are useful for the purpose of distilling data for diagnosis, prognosis, therapeutic guidance, or monitoring or evaluating the efficacy of treatment. Probes of the disclosure can hybridize to such nucleic acid molecules. In some cases, designing probes for the HLA genes can be difficult because of homology in sequences shared by various HLA genes. In some embodiments, detecting the clonal loss of HLA expression can be difficult because HLA genes can be both highly polymorphic and homologous to one another. In some aspects, provided herein is are methods and systems that comprise generating a genetic profile (e.g., by next-generation sequencing) to identify a plurality of variant sequences (e.g. HLA variant sequences, sequences encoding tumor antigen variants, or other tumor characteristics) present in the subject prior to designing probes for use with an individual or a tumor sample. Examples of probes include, but are not limited to, padlock probes, molecular inversion probes, or variants thereof. The probes can comprise a region that has complementarity with a target and may comprise an additional region that does not hybridize with the target. The probes can be circular probes. The probes can be circularizable probes.

The probes can comprise two or more components (e.g., multicomponent probes). For example, the probes can comprise two or more separate nucleic acid fragments, and the two or more separate nucleic acid fragments can be joined together to form a circular probe when the two or more separate nucleic acid fragments hybridize to a target nucleic acid molecule. In some cases, the probe can comprise a first nucleic acid molecule comprising (i) a first hybridizing region having a first sequence complementary to a first target sequence of a target nucleic acid molecule and (ii) a first nonhybridizing region at a first end of the first nucleic acid molecule. The probe can further comprise a second nucleic acid molecule comprising (i) a second hybridizing region having a second sequence complementary to a second target sequence of the target nucleic acid molecule and (ii) a second nonhybridizing region at a second end of the second nucleic acid molecule. The first nucleic acid molecule and the second molecule may be configured such that, upon hybridization of the first sequence to the first target sequence and the second sequence to the second target sequence: (1) the first nonhybridizing region and the second nonhybridizing region do not hybridize with the target nucleic acid molecule; and (2) the first end and the second end undergo coupling to one another. The first nucleic acid molecule and the second nucleic acid molecule may be configured such that, upon hybridization of the first sequence to the first target sequence and the second sequence to the second target sequence, the first end of the first nucleic acid molecule and the second end of the second nucleic acid molecule may be adjacent.

The probes such as padlock probes can undergo gap filing or circularization and amplification for detection. Once hybridized to targeted nucleic acid molecules, the identity and location of the probe molecules can be determined with the use of techniques such as sequencing by extension with reversible terminators, fluorescent in situ sequencing, pyrosequencing, and massively parallel signature sequencing (MPSS) in the context of the 3D matrix. Determination of the identity and location of probe molecules can allow for the generation of spatial maps showing the location of MHC protein and/or tumor antigen expression. Spatial maps can inform the selection of treatments for cancer. In some instances, administration of a treatment selected based in part on the spatial expression of MHC proteins and/or tumor antigens can have an increased probability of efficacy compared to a treatment that was selected without knowledge related to the spatial expression of MHC proteins and/or tumor antigens.

Methods of Analyzing the Spatial Distributions of Target Nucleic Acids

Methods and systems disclosed herein can utilize probe molecules to identify target sequences (e.g., variant sequences) in a biological sample such as, tissue, tumor tissue, populations of cells, individual cells, or a derivative of any of the foregoing. In some cases, the methods and systems can further determine the location of identified target sequences. In some cases, the determined identities and locations of target sequences can be used to generate visual representations (e.g., for display on a user interface, such as a graphical user interface) of biological samples. In some instances, a target sequence is a sequence of nucleotides within a biological sample.

In some cases, probes of the disclosure comprise a nucleic acid targeting sequence (or target hybridizing sequence or region). Additionally, probe molecules of the disclosure can further comprise identifier nucleic acid sequences (e.g., barcode sequences), sequencing primer binding sites, and padlock binding sites. Nucleic acid targeting sequences can be used to direct the binding of a probe to a specific nucleic acid within a cell. For example, a nucleic acid targeting sequence can comprise a specific sequence of nucleotides that causes the probe to target and hybridize to a specific nucleic acid within a cell. In some cases, the nucleic acid targeting sequence comprises a sequence of nucleotides that is complementary to a sequence of the targeted nucleic acid, causing hybridization of the targeting sequence and the target via Watson-Crick base pairing. In some cases, a nucleic acid targeting sequence is an HLA targeting sequence that is designed to bind to a nucleic acid corresponding to an HLA variant sequence. Nucleic acid targeting sequences of the disclosure can be, for example, from 21 to 200 nucleotides long. In some cases, the nucleic acid targeting sequences of the disclosure can be at least about 10, 15, 20, 25, 30, 35, 40, 45, 50, 55, 60, 65, 70, 75, 80, 85, 90, 95, 100, 150 or more nucleotides long. In some cases, the nucleic acid targeting sequences of the disclosure can be at most about 200, 150, 100, 95, 90, 85, 80, 75, 70, 65, 60, 55, 50, 45, 40, 35, 30 or less nucleotides long.

In some embodiments, each probe targets and hybridizes to a specific target nucleic acid molecule and the specific target nucleic acid molecule is not bound by multiple probes. For example, a sequence of at most about 20, 15, 10, 5 or less nucleotides long of a particular MHC or human leukocyte antigen (HLA) variant sequence is targeted by each probe. In some cases, a position unique to a particular MHC or HLA allele is at most about 5, 4, 3, 2, 1 or less nucleotides long. In some aspects, padlock probes may be useful for detecting short target nucleic acid sequences (e.g., distinguishing base(s) of a HLA variant).

In some cases, the target nucleic acid corresponds to and/or is specifically co-localized with a variant or transcript sequence of interest. In some instances, the target sequence is an HLA sequence or a variant or a transcript sequence corresponding to an antigen. In some instances, the target sequence comprises an HLA allele or a mutation. The target can be associated with, for example, an increased risk a cancer, a tumor or tumor associated antigen, a cancer/testis antigen, a cancer antigen, an oncofetal protein, a tumor mutation, a tumor suppressor protein, or a neoantigen. When a probe molecule hybridizes to a nucleic acid molecule that corresponds to and is co-localized with a target sequence of interest, detection of the identity and location of the probe molecule allows for or the detection of the identity and location of the targeted sequence. In some cases, the target sequence encodes a protein or a portion thereof and detection of the identity and location of the target sequence allows for the identity and location of the protein to be determined.

Probe molecules of the disclosure can be identified by, for example, identifying an identifier nucleotide sequence. An identifier nucleotide sequence can allow for the specific identification of a probe molecule. According to one aspect of the disclosure, an identifier nucleotide sequence is a unique nucleotide sequence. According to another aspect of the disclosure, an identifier nucleotide sequence is a substantially unique nucleotide sequence. According to yet another aspect of the disclosure, an identifier nucleotide sequence can convey enough information about a probe molecule to infer the identity of a probe molecule with at least a non-uniform probability. In some cases, the identifier nucleotide sequence can be held in common for some or all of the probes that bind to a particular nucleic acid sequence or target. In some cases, the probe can comprise a combination of identifier nucleotide sequences described herein.

In some cases, additional information can be used to support an inference on the identity of a probe molecule. Additional information can include the identity of the different probe molecules that have contacted the sample or information about the biological sample being contacted. In some cases, such as when multiple replicates of a probe molecule are used to target multiple replicates of the same nucleic acid molecule, each replicate probe molecule can comprise the same identifier nucleotide sequence.

In some embodiments, a probe molecule of the disclosure has a length ranging from 21 to 200 nucleotides long. In some cases, the probe molecule of the disclosure can be at least about 10, 15, 20, 25, 30, 35, 40, 45, 50, 55, 60, 65, 70, 75, 80, 85, 90, 95, 100, 150 or more nucleotides long. In some cases, the probe molecule of the disclosure can be at most about 200, 150, 100, 95, 90, 85, 80, 75, 70, 65, 60, 55, 50, 45, 40, 35, 30 or less nucleotides long.

The probe can be a multicomponent probe comprising a first nucleic acid molecule and a second nucleic acid molecule, and the variant sequence can be included within the target hybridizing region of one of the two components, for example, the first nucleic acid molecule. The first nucleic acid molecule can further include the identifier nucleotide sequence, such that the plurality of probes targeting a sequence variation can share a common component (e.g., the first nucleic acid molecule) with conserved sequence. In some cases, the probes can comprise degenerate bases (e.g., W). Such probes can be prepared during synthesis, comprising a mixture of probes with A and T at that position. The identifier nucleotide sequence can be detected by sequencing such as sequencing by hybridization.

The identity and/or location of a target sequence (e.g., variant sequence) can be determined via the identification of a portion of a probe molecule. In some cases, the identity and/or location of a target sequence is determined via the identification of about 10%, about 20%, about 30%, about 40%, about 50%, about 60%, about 70%, about 80%, about 90%, or about 100% of a probe molecule. In some cases, the identity and/or location of a target sequence is determined via the identification of 50%-100% of a probe molecule. In some cases, the identity and/or location of a target sequence is determined via the identification of at least 10%, at least 20%, at least 30%, at least 40%, at least 50%, at least 60%, at least 70%, at least 80%, of at least 90% of a probe molecule. In some cases, the identity and/or location of a target sequence is determined via the identification of at most 10%, at most 20%, at most 30%, at most 40%, at most 50%, at most 60%, at most 70%, at most 80%, or at most 90% of a probe molecule. In some cases, the identity and/or location of a target sequence is determined via the identification of the identifier nucleotide sequence (e.g., barcode sequence) of a probe. In some cases, the identity and/or location of a target sequence is determined via the identification of about 10%, about 20%, about 30%, about 40%, about 50%, about 60%, about 70%, about 80%, about 90%, or about 100% of a identifier nucleotide sequence. In some cases, the identity and/or location of a target sequence is determined via the identification of 50%-100% of a identifier nucleotide sequence. In some cases, the identity and/or location of a target sequence is determined via the identification of at least 10%, at least 20%, at least 30%, at least 40%, at least 50%, at least 60%, at least 70%, at least 80%, of at least 90% of a identifier nucleotide sequence. In some cases, the identity and/or location of a target sequence is determined via the identification of at most 10%, at most 20%, at most 30%, at most 40%, at most 50%, at most 60%, at most 70%, at most 80%, or at most 90% of a identifier nucleotide sequence. In other cases, the identity and/or location of a target sequence is determined via the identification of an entire probe molecule. In some cases, a single nucleotide in the identifier nucleotide sequence of the probe may be sufficient to determine a variant. For example, within the identifier nucleotide sequence, a nucleotide identity at a single position can distinguish between up to 4 variant target sequences.

Determining the Identity and Location of Variant Sequences via Probe Detection

Methods and systems of the disclosure can identify and locate target sequences within a biological sample. In some cases, the target sequences can be variant sequences, which encode for MHC proteins, antigens (e.g., tumor antigens), or portions thereof.

In some cases, the target sequences (e.g., a second nucleic acid for analysis) can encode antigens, inflammatory markers, or cell typing markers (e.g., immune cell marker, cancer marker). For example, a target sequence may be associated with immune cells such as B cells, T cells, NK (natural killer) cells, NK T cells, professional antigen-presenting cells (APCs), and non-professional antigen-presenting cells, and inflammatory cells (neutrophils, macrophages, monocytes, eosinophils, and basophils). In some examples, a target sequence may be associated with modulation of an existing immune response, a developing immune response, a potential immune response, or the capacity to induce, regulate, influence, or respond to an immune response. In some cases, a target sequence may be associated with altered production and/or secretion of certain classes of molecules such as cytokines, chemokines, growth factors, transcription factors, kinases, costimulatory molecules, or other cell surface receptors. In some cases, the target sequences can encode a receptor or ligand on the surface of the cancer cell (e.g., epidermal growth factor receptor (EGFR, ErbB-1, HER1)). In some cases, the target sequences can encode a T cell marker e.g., CD3, CD4, or CD8).

The location and identify of variant sequences can be determined by identifying and locating probe molecules (or portions thereof) targeting the variant sequences. In some instances, probe molecules can target a nucleic acid corresponding to a specific variant sequence. A nucleic acid corresponding to a specific variant sequence can be, for example, a genomic deoxyribonucleic acid (DNA) sequence, a complementary deoxyribonucleic acid (cDNA) molecule reverse transcribed from a variant sequence, a ribonucleic acid (RNA) molecule transcribed from a variant sequence, and amplification products of the foregoing. Additionally/alternatively, probe molecules can discriminate between two or more nucleic acids corresponding to different variant sequences known to be present in a biological sample. For example, a method of the disclosure can comprise generating a genetic profile of a subject from which a sample is obtained to identify a plurality of variant sequences (e.g. HLA variant sequences or sequences encoding tumor antigen variants) present in the subject. Genetic profiles can be generated via, for example, RNA sequencing, exome sequencing, or whole genome sequencing. Probe molecules can be designed to discriminate between two nucleic acid molecules corresponding to sequences of the plurality of variant sequences and/or to preferentially hybridize to a nucleic acid molecule corresponding to only one of the identified variant sequences. The identity and location of the identified variant sequences within the biological sample can then be identified by contacting the sample with the designed probe molecules.

In some examples, the location and identity of a probe molecule or portion thereof is determined by first amplifying the probe molecule to generate a corresponding amplification product and subsequently determining the location and identity of the amplification product or portion thereof. In other examples, the location and identity of a probe molecule or portion thereof can be determined directly.

Methods that can be used to determine the location and identity of probe molecules or portions thereof include methods of sequencing nucleic acids in situ within a 3D matrix. Sequencing methods, such as sequencing by extension with reversible terminators, fluorescent in situ sequencing (FISSEQ), OligoFISSEQ, pyrosequencing, massively parallel signature sequencing (MPSS) and the like, can be used to sequence nucleic acids, including the probes comprising nucleic acids described herein, within a 3D matrix. Sequencing methods of the disclosure can determine the location and identity of probe molecules or portions thereof either via the sequencing of probe molecules (or portions thereof) directly or via sequencing of corresponding amplification products (or portions thereof).

Pyrosequencing is one such method that can be used with the methods and systems described herein. Pyrosequencing is a method in which pyrophosphate (PPi) is released during each nucleotide incorporation event (i.e., when a nucleotide is added to a growing polynucleotide sequence). The PPi released in the DNA polymerase-catalyzed reaction can be detected by ATP sulfurylase and luciferase in a coupled reaction which can be visibly detected. The added nucleotides can be continuously degraded by a nucleotide-degrading enzyme. After the first added nucleotide has been degraded, the next nucleotide can be added. As this procedure is repeated, longer stretches of the template sequence can be deduced.

Massively Parallel Signature Sequencing (MPSS) is another such sequencing method which utilizes ligation-based DNA sequencing simultaneously on microbeads. A mixture of labelled adaptors comprising all possible overhangs is annealed to a target sequence of four nucleotides. The label can be detected upon successful ligation of an adaptor. A restriction enzyme is then used to cleave the DNA template to expose the next four bases.

Fluorescent in situ sequencing (FISSEQ) is another sequencing method that can be used with the methods and systems described herein. FISSEQ is a process during which a series of biochemical processing operations are interlaced with fluorescent imaging operations within a biological sample. Sequencing methods that can be employed by FISSEQ include sequencing by synthesis, sequencing by ligation, and sequencing by hybridization. A FISSEQ assay can involve: (1) the extension of DNA via the addition of a single type of fluorescently-labelled nucleotide triphosphate (dNTP) to a reaction, (2) washing away of unincorporated nucleotide, (3) the detection of nucleotide incorporation by fluorescence imaging, (4) the repetition of operations 1-3 with each of the four dNTPs in turn, and (5) the repetition of operations 1-4 in cycles. At the beginning of each subsequent cycle, the fluorescence from previous cycles can be bleached or digitally subtracted or the fluorophore can be cleaved from the nucleotide and washed away. Following the completion of each cycle, a nucleotide present in the sequence can be identified, thus allowing for the identification of a sequence via the completion of multiple cycles. In some embodiments, operation (1) of the FISSEQ cycle described above can involve the addition of a mixture of all four dNTPS each labelled with a different fluorophore. In such embodiments operations 1-3 may not be repeated individually for each of the four dNTPs, as the identity of the dNTP incorporated in each cycle can be determined based on detection of the fluorescent label corresponding to the dNTP. The probes described herein can also be detected by OligoFISSEQ, which leverages fluorescence in situ sequencing (FISSEQ) of barcoded Oligopaint probes to enable visualization of many targeted genomic regions. The probe can be an Oligopaint probe. The probe can comprise a barcode, which can be interrogated by various methods to identify the probe and corresponding target sequence. For example, the barcode can be identified by sequencing by synthesis, sequencing by ligation, sequencing by hybridization, hybridization chain reaction or cyclic hybridization chain reaction. For another example, the barcode can be identified by temporal detection, where two or more subsequences of the barcode can be sequentially detected by sequencing or hybridization.

Sequencing data can be processed to allow for the visualization of each sequenced nucleotide strand as a localized spot in a fluorescent image. In some cases, the data include a sequence of colors corresponding to the nucleotide sequence of the strand. By analyzing successive fluorescent images of FISSEQ cycles, the identity and location of a vast number of unique probes can be determined in a single biological sample. In some instances, the identity and location of expressed antigen encoding, or HLA, genes can be inferred from the identity and location of probe molecules. Computational methods can then be employed to construct visual representations of gene expression in biological samples. In some embodiments, a method disclosed herein can simultaneously present the location of at least about 50,100,200, 300, 400, 500 or more expressed genes within a genome, or all expressed genes within a genome (e.g., whole genome or transcriptome).

In cases where sequencing methods (e.g., FISSEQ) are used for the sequencing of probe molecules or portions thereof (e.g., identifier nucleotide sequences) directly, the probe sequences may be designed to optimize the sequencing protocol for properties such as compactness and error robustness. For example, probe or identifier nucleotide sequence of the minimum length for unique specification of each target species can be used. In some embodiments, the spatial sequencing of identifier molecules can be combined with non-spatial methods of high throughput sequencing to sequence and identify longer nucleic acid molecules such as those corresponding to DNA variants, transcripts, antigens, and HLA alleles. In some embodiments, the spatial sequencing of identifier molecules can be combined with the identification of proteins, such as antigens. This can happen through antibody staining or the spatial sequencing of nucleic acid tagged antibodies that identify proteins. Additionally, error correction features such as redundant or parity bits of information can be added to probe sequences.

Amplification Methods

In some embodiments, the target sequences such as variant sequences, nucleic acids corresponding to variant sequences, probes, derivatives of the foregoing, and/or portions of any of the foregoing (e.g., identifier nucleotide sequences) are subjected to amplification reactions prior to being identified. Amplification of a probe or portion thereof generates a corresponding amplification product comprising an amplified nucleic acid sequence. In some cases, target sequences, nucleic acids corresponding to target sequences or probe molecules (or portions thereof) are identified via the identification of a corresponding amplification nucleic acid sequence, such as an amplicon, or a portion thereof. In some cases, target sequences, nucleic acids corresponding to target sequences, probe molecules or portions thereof are identified via the identification of about 10%, about 20%, about 30%, about 40%, about 50%, about 60%, about 70%, about 80%, about 90%, or about 100% of an amplified nucleic acid sequence. In some cases, variant sequences, nucleic acids corresponding to variant sequences, probe molecules, or portions thereof are identified via the identification of 50%-100% of an amplified nucleic acid sequence. In some cases, the identity and/or location of a variant sequence is determined via the identification of at least 10%, at least 20%, at least 30%, at least 40%, at least 50%, at least 60%, at least 70%, at least 80%, of at least 90% of an amplified nucleic acid sequence. In some cases, the identity and/or location of a variant sequence is determined via the identification of at most 10%, at most 20%, at most 30%, at most 40%, at most 50%, at most 60%, at most 70%, at most 80%, or at most 90% of an amplified nucleic acid sequence.

Amplification products can be generated using various methods for nucleic acid amplification, including solid-state or semi-solid-state amplification methods. Nucleic acid molecules can be amplified by rolling circle amplification (RCA), as by using a circular template molecule and an enzyme capable of rolling circle amplification, such as Phi29, Bst, Vent, 9°N DNA polymerases and related enzymes. Nucleic acid molecules can be amplified by polymerase chain reaction (PCR), as by using a DNA polymerase enzyme. Nucleic acid molecules can be amplified by an RNA polymerase using the in vitro transcription reaction, such as by T7 RNA polymerase. In some cases, nucleic acid molecules can be subjected to multiple different amplification reactions.

Amplification products may comprise functional linkage groups for tethering to a 3D matrix, such as acrylamide or click-reactive groups, enabling the products of amplification to be spatially immobilized via covalent gel linkages. According to one aspect, the functional linkages can be incorporated during amplification using nucleotide analogs, including amino-allyl dUTP, 5-TCO-PEG4-dUTP, C8-Alkyne-dUTP, 5-Azidomethyl-dUTP, 5-Vinyl-dUTP, 5-Ethynyl dUTP, or a combination thereof. According to a separate aspect, for amplification methods using one or more primers, one or more of the primers may comprise a functional linkage group for tethering to a 3D matrix, i.e., solid-state.

Further, amplification products may be subsequently processed, chemically or biochemically, using mechanisms including, but not limited to, fragmentation, end-modification, second-stranding, annealing of accessory strands, such as priming, gap filling, circularization, blunt ending, phosphorylation, dephosphorylation, protection, and deprotection. End-modifications may entail the addition and/or removal of bases or sequences. For example, additional sequences may be used to subject the amplification products to next generation sequencing reactions. End modifications may also entail adding chemical moieties that may be useful for linkages or coupling the amplification products to another molecule. For example, the end may be phosphorylated or dephosphorylated by an enzyme, for example, a kinase or phosphatase. Protecting groups may also be added or removed to allow or prevent particular reactions from taking place. Blunt ending may also occur in which an overhang comprising a portion of single stranded nucleic acid is removed. Amplification products may be subjected to second stranding reactions which may result in additional nucleic acid molecules. Second stranding may be performed by adding in a primer which is complementary to the amplification product and a polymerizing enzyme to generate additional nucleic acid molecules. Amplification products may also be subjected to gap filling via a polymerizing enzyme, which may link two strands of DNA together via the synthesis of intervene bases. Amplification products may also be circularized via the activity of a gap filling reaction, extension reaction, ligation reaction, or a combination thereof, in which a circular nucleic acid is generated from a linear nucleic acid.

Amplification products or subunits thereof may be processed into a greater plurality of subunits, such as by fragmentation. Methods of fragmenting amplification products include mechanisms which are random, or substantially random, including by the DNA hydrolysis or DNA nicking activities of enzymes including, but not limited to, DNase, endonucleases, and DNA repair enzymes. According to one aspect of the random fragmentation mechanism, nucleotides or nucleotide analogs can be incorporated into an amplification product during synthesis, which subsequently become the site of amplification product fragmentation. Examples include incorporation of dUTP with fragmentation by Uracil-Specific Excision Reagents (USER), such as the combination of Uracil DNA Glycosylase (UDG) and an endonuclease such as Endonuclease VIII or Endonuclease IV; incorporation of inosine with fragmentation by Endonuclease V; and by incorporation of monomers bearing internal cleavage sites, such as oligonucleotides with internal disulfide or bridging phosphorothioate linkages during ligase-mediated amplification. Methods of fragmenting an amplification product can include mechanisms for site-directed fragmentation, such as by restriction endonucleases, for which single-stranded sites may be splinted with an accessory oligonucleotide to facilitate the restriction endonuclease reaction, and by other sequence-specific nucleic acid cutting mechanisms including by Cas9, C2c2, and other nucleic-acid-directed nucleic-acid restriction enzymes, and by Transcription Activator-Like Effector Nucleases (TALENs). According to some embodiments, a rolling circle amplification product can be fragmented into molecules corresponding to a probe or identifier nucleotide sequence. Fragmentation may also be performed by subjecting a rolling circle amplification product to a reverse primer in a process known as hyberbranched rolling circle amplification (RCA). For example, RCA may create a long nucleic strand comprising multiple repeats of the template nucleic. Subjecting the amplification product to a reverse primer may allow a polymerization may create separate double strand DNA molecules resulting in the RCA amplification product being fragmented.

Probes for Amplification

Methods and systems disclosed herein can utilize various probes. The probe can be a linear probe. The probe can be a circularizable probe. The probe can be a circular probe. The probe can be a padlock probe. The probe can be a molecular inversion probe. The probe can comprise a target hybridizing region and target nonhybridizing region. The probe (e.g., the target nonhybridizing region) can further comprise a primer binding sequence and/or an identifier nucleotide sequence.

The probe can be a multicomponent probe. The probe can comprise two or more separate nucleic acid fragments, and the two or more separate nucleic acid fragments can be joined together to form a circular probe when the two or more separate nucleic acid fragments hybridize to a target nucleic acid molecule. In some cases, the probe can comprise a first nucleic acid molecule comprising (i) a first hybridizing region having a first sequence complementary to a first target sequence of a target nucleic acid molecule and (ii) a first nonhybridizing region at a first end of the first nucleic acid molecule. The probe can further comprise a second nucleic acid molecule comprising (i) a second hybridizing region having a second sequence complementary to a second target sequence of the target nucleic acid molecule and (ii) a second nonhybridizing region at a second end of the second nucleic acid molecule. The first nucleic acid molecule and the second molecule may be configured such that, upon hybridization of the first sequence to the first target sequence and the second sequence to the second target sequence: (1) the first nonhybridizing region and the second nonhybridizing region do not hybridize with the target nucleic acid molecule; and (2) the first end and the second end undergo coupling to one another. The first nucleic acid molecule and the second nucleic acid molecule may be configured such that, upon hybridization of the first sequence to the first target sequence and the second sequence to the second target sequence, the first end of the first nucleic acid molecule and the second end of the second nucleic acid molecule may be adjacent. The first nucleic acid molecule and the second nucleic acid molecule may be configured such that, upon hybridization of the first sequence to the first target sequence and the second sequence to the second target sequence, the first end and the second end undergo coupling to one another via a nucleic acid extension reaction. The first nucleic acid molecule and the second nucleic acid molecule may be configured such that, upon hybridization of the first sequence to the first target sequence and the second sequence to the second target sequence, the first end and the second end undergo coupling to one another via a nucleic acid ligation reaction. The first nucleic acid molecule and the second nucleic acid molecule may be configured such that, upon hybridization of the first sequence to the first target sequence and the second sequence to the second target sequence, the first end and the second end undergo coupling to one another via a hybridization reaction. The first nucleic acid molecule and the second nucleic acid molecule may be configured such that, upon hybridization of the first sequence to the first target sequence and the second sequence to the second target sequence, the first end and the second end undergo coupling to one another via a nucleic acid extension and a nucleic acid ligation reaction.

Methods and systems disclosed herein can utilize padlock probes (herein known as "padlocks") in the detection of target sequences, nucleic acids corresponding to target sequences, probes, or portions of probes (e.g., identifier nucleotide sequences) within a biological sample. Padlocks can be designed to bind specifically to targets such as nucleic acids corresponding to target sequences, probes, or portions of probes disclosed herein and can comprise a first end, a second end, and 5' and 3' terminal regions. In some cases, padlocks bind to specific portions of probes disclosed herein such as padlock binding sites or identifier nucleotide sequence. By hybridization to a target, the ends of the padlock are brought into juxtaposition for ligation. The ligation may be direct or indirect. In other words, the ends of the padlock may be ligated directly to each other or they may be ligated to an intervening nucleic acid molecule or a sequence of nucleotides. Thus, the terminal regions of the padlock probe may be complementary to adjacent, or contiguous, regions in the target (e.g., probe) to which it is targeted, or they may be complementary to non-adjacent or non-contiguous regions in the target (e.g., probe) to which it is targeted. In the cases where the padlock probe is complementary to non-adjacent or non-contiguous regions of the target, for ligation to occur, the "gap" between the two ends of the hybridized padlock probe can be filled by an intervening oligonucleotide molecule or a sequence of nucleotides.

A "gap" region described herein may be of various lengths. For example, a gap region can comprise at least 1, at least 5, at least 10, at least 15, at least 20, at least 25, at least 30, at least 35, at least 40, at least 45, at least 50 or more nucleotide(s). For another example, a gap region can comprise from 2 to 10, from 10 to 20, from 20 to 50, from 50 to 100, from 100 to 150, from 150 to 200, from 200 to 300, from 300 to 400, from 400 to 500, or from 2 to 500 nucleotides. A gap region can be filled in by incorporating one or more nucleotides in an extension reaction, for example, by extending from the 3' end of the two ends. The extension reaction can be performed by a polymerase. The gap region can also be filled in by hybridizing an additional nucleotide or an additional oligonucleotide sequence to the gap region. The length of the additional oligonucleotide sequence can be determined based on the length of the gap region. For example, the additional oligonucleotide sequence can be of the same length as the gap region such that after hybridizing with the gap region, the 5' end of the additional oligonucleotide sequence is adjacent to the 3' end of the padlock and the 3' end of the additional oligonucleotide sequence is adjacent to the 5' end of the padlock. For example, the additional oligonucleotide sequence can comprise from 2 to 10, from 10 to 20, from 20 to 50, from 50 to 100, from 100 to 150, from 150 to 200, from 200 to 300, from 300 to 400, from 400 to 500, or from 2 to 500 nucleotides. The circularized padlock can then be generated by ligating the ends of the additional oligonucleotide sequence with the ends of the padlock.

Upon addition to a sample having a target molecule, the ends of the padlock may hybridize to complementary regions in a target molecule or derivative thereof (e.g., probe molecule). Following hybridization, the padlock may be circularized by direct or indirect ligation of the ends of the padlock by a ligase enzyme. The circularized padlock may be subjected to amplification to generate an amplification product. For example, the circulated padlock may be subjected to rolling circle amplification (RCA) to generate a DNA nanoball (i.e., rolony). The circularized padlock may be primed by the 3' end of the probe nucleic acid sequence (i.e., the RCA is target-primed). A DNA polymerase with 3'-5' exonuclease activity may be used. This can permit the digestion of the probe strand in a 3'-5' direction to a point adjacent to the bound padlock. Alternatively, the targeted probe may be of appropriate length and may act as the primer for the DNA polymerase-mediated amplification reaction without such digestion. As a further alternative, instead of priming the RCA with the targeted probe molecule, an additional primer that can hybridize to the padlock may be added in the sample and used for an amplification reaction. The amplification product (e.g., rolony) can be identified and its location determined. The location and identity of the amplification product can be used to subsequently locate and identify the targeted probe molecule, which in turn can locate and identify a sub-cellular structure that co-localizes with the nucleic acid target of the probe molecule. Using a plurality of padlock probes, a number of target nucleic acids can be detected in a multiplex manner. In some embodiments, a set of probes for detecting a plurality of target nucleic acids is designed and provided for a particular sample, e.g., a personalized probe set for an individual or a tumor sample from the individual.

A padlock disclosed herein may comprise functional moieties for immobilization to a 3D matrix, either directly or indirectly, as via a hybridized oligonucleotide. For example, a tethering oligo hybridized to the backbone of the padlock, e.g., outside the domains responsible for hybridizing to the target probe molecule, may serve as a rolling circle amplification primer, thereby serving to tether the padlock molecule (and targeted probe molecule) via DNA hybridization prior to rolling circle amplification, and subsequently serving to tether the rolling circle amplification product (i.e., rolony) after rolling circle amplification for the purpose of preserving the spatial information associated with the original targeted (by the probe) nucleic acid molecule, targeted (by the padlock) probe molecule, padlock, and rolony.

Predicting Presentation of Antigen Peptides in the Context of MHC Proteins

Methods disclosed herein may comprise predicting the presentation of specific MHC-antigen complexes on the surface of a cell. In some cases, the spatial distribution of an MHC-antigen complex presented on the surface of a cell within a biological sample is predicted. Predictions can be based in whole or in part on, for example, the presence, absence, or spatial distribution of target sequences in a biological sample. A variant sequence can be, for example, an HLA variant sequence or be associated with a tumor antigen (e.g., comprise a mutation associated with a tumor antigen) such as a tumor-specific antigen, a tumor-associated antigen, or a neoantigen. In some instances, a variant sequence is detected within a cell. Additionally or alternatively, the presence of multiple variant sequences (e.g., an HLA variant sequence and a variant sequence associated with a tumor antigen) can be detected within the same cell. In some cases, antigens presented as part of MHC-antigen complexes are informative of cancer. For example, an antigen can be a tumor antigen. In some cases, the antigen can be a protein that healthy subjects normally only express in specific cells (e.g., a cancer/testis antigen) or during specific developmental stages (e.g., an oncofetal protein).

In some cases, methods disclosed herein comprise using a computer algorithm to predict the presentation or absence and/or spatial distribution of MHC-antigen complexes within a biological sample. Computer algorithms may aid in the prediction of MHC-antigen complex presentation by predicting the ability of MHC binding motifs to bind antigens. Computer algorithms can be used alone or in combination with methods to determine the presence, absence, or spatial distribution of variant sequences. Non-limiting examples of computer algorithms that can be used with methods of the disclosure include scoring function based computer algorithms such as SYFPEITHI, RANKPEP, PickPocket 1.1, SMMPMBEC, PSSMHCpan 1.0, and MixMHCpred 2.0.1; machine learning based algorithms such as NetMHC 4.0, NetMHCstabpan, NetMHCPan 4.0, MHCnuggets 2.0, ConvMHC, and HLA-CNN; and consensus algorithms such as IEDB-AR-Consensus, and NetMHCcons.

Visualizing MHC-Antigen Co-Localization

Methods disclosed herein may comprise visualizing the co-localization of antigen and MHC protein expression in a biological sample. In some cases, a visual representation of MHC-antigen expression co-localization can be generated by a computer for display on a user interface, such as a graphical user interface. Visual representations of the disclosure can depict the presence or absence of nucleic acids, such as nucleic acids associated with and/or corresponding to MHC or antigen (e.g., tumor antigen) expression. Additionally or alternatively, visual representations can depict predictions of MHC-antigen complex presentation within a biological sample. Visual representations can depict the predicted presence, or absence, of MHC-antigen complexes within a biological sample.

In some instances, visual representations display information on a cellular level. For example, a visual representation can depict the presence of nucleic acids, the absence of nucleic acids, the predicted presence of MHC-antigen complexes, or the predicted absence of MHC-antigen complexes within or on the surface of individual cells. In some cases, methods disclosed herein can identify clones within a biological sample. Clones can be identified based on the co-expression, or predicted co-expression, of an antigen and MHC protein in a single cell. In some cases, clones are generated by analyzing a generated visual representation. In some cases, a visual representation is generated to depict the distribution of clones and/or clonal populations within a biological sample (i.e., the clonal structure of the sample). Visual representations of the clonal structure of a biological sample such as a tumor can be used to design, or select, a treatment for a subject from which the sample is derived. For example, a visual representation a tumor's clonal structure can be used to design or select a bispecific antibody or T-cell receptor (TCR) based therapy against specific MHC-antigen complexes or cancer vaccines against such complexes.

Identification of Cancer Cells

Information pertaining to MHC and/or antigen expression can be used to identify a cancerous cell. For example, the presence of a tumor antigen, may indicate that a cell is cancerous. Cancer cell clones, sub-clones, and clonal populations of cells can also be identified based on the presence or absence of HLA gene variants and/or genes encoding antigen proteins in a cell. The presence of an HLA gene variant and/or gene encoding an antigen protein can be detected by, for example, determining the identity and location of a probe molecule hybridized to a corresponding nucleic acid using in situ sequencing. In some instances, the presence and location of cancer cells, cancer cell clones, sub-clones, and/or clonal populations of cancer cells can be portrayed in a visual representation.

Selection and Administration of Therapies

Knowledge of MHC and/or antigen expression in a biological sample derived from a subject can identify the presence of a cancer cell and/or guide the selection of an effective immunotherapy for the subject. Immunotherapies often rely on immune cells targeting tumor antigens presented on the surface of cancer cells. Frequently, the ability of an immune cell to effectively target a tumor antigen depends on display of the tumor antigen as part of a particular MHC-antigen complex. A loss of expression of, or mutation in, an MHC protein from a cancer cell can lead to altered or improper presentation of a tumor antigen on the cell surface and render an immunotherapy ineffective. Similarly, a loss of expression of, or mutation in, a tumor antigen can render an immunotherapy ineffective. Conversely, the presence of MHC-antigen complexes on a cancer cell surface can indicate that a cancer cell will be susceptible to a particular immunotherapy. In some cases, antigens and/or MHC protein expression is lost in only a portion of cells in a tumor. In some cases, antigens and/or MHC proteins are mutated in only a portion of cells in a tumor.

Methods disclosed herein can comprise selecting a therapy (e.g., an immunotherapy) to be administered to a subject. In some cases, the methods further comprise administering a therapy such as an immunotherapy to a subject. A therapy can be selected based at least in part on the spatial distribution of antigens, MHC proteins, and/or mutants thereof. Additionally or alternatively, a therapy can be selected based at least in part on the presence or absence of antigens, MHC proteins, and/or mutants thereof in a biological sample. For example, a therapy that targets a MHC-antigen complex that is expressed or predicted to be expressed homogenously throughout a tumor volume can be selected and administered to a subject. In some cases, a therapy (e.g., an immunotherapy) that is likely to effectively target a clonal population can be selected and administered to a subject. In some cases, multiple clonal populations can be predicted to exist in a tumor and multiple therapies likely to effectively target each clonal population can be selected. In some cases, a method of the disclosure comprises administering one or more therapies likely to target a clonal population to a subject. In some cases, a method of the disclosure comprises identifying a clonal population that is likely to evade a particular immunotherapy and targeting the clonal population with a second therapy rather than with the immunotherapy that is not likely to be effective. Non-limiting examples of immunotherapies that can be selected and/or administered as part of methods disclosed herein include recombinant T-cell therapies (including T cells expressing recombinant or exogenous T cell receptors), chimeric antigen receptor (CAR) T-cell therapies, cancer vaccines, checkpoint inhibitors, and B-cell therapies.

T-cell receptors (TCRs) are generally found on the surface of T-cells and are responsible for recognizing antigens bound to MHC proteins. When TCRs engage with MHC-antigen complexes the corresponding T-cell is activated. T-cell activation can facilitate destruction of the recognized cell. In recombinant T-cell therapies, T-cells can be engineered to express TCRs targeted towards MHC-antigen complexes expressed by cancer cells so that when the TCR binds the MHC-antigen complex T-cell activation leads to destruction of the cancer cell. In some cases, TCRs are engineered to target a particular MHC-antigen complex predicted or known to be expressed on a cancer cell within a biological sample. For example, a target antigen or portion thereof can be used to produce or generate a TCR. In some cases, directed evolution methods are used to generate TCRs with altered properties, such as with higher affinity for a specific MHC-antigen complex. In some cases, directed evolution is achieved by display methods including, but not limited to, yeast display, phage display, or T cell display. In some cases, display approaches involve engineering, or modifying, a known, parent, or reference TCR. For example, in some cases, a wild-type TCR can be used as a template for producing mutagenized TCRs with a predetermined altered property, such as higher affinity for a predetermined target antigen or MHC-antigen complex. In some embodiments, a recombinant T-cell therapy is engineered or selected to target an antigen and/or MHC-antigen complex known or predicted to be expressed within a biological sample. In some cases, a recombinant T-cell therapy is engineered or selected based at least in part on the spatial distribution of antigen and/or MHC expression in a biological sample. In some cases, a method of the disclosure comprises administering an engineered or selected recombinant T-cell therapy to a subject.

CAR T-cell therapies utilize CAR T-cell receptors that have been engineered to combine both antigen binding and T-cell activating functions into a single receptor. In some embodiments of a method disclosed herein, a CAR T-cell therapy can be engineered or selected to target an antigen and/or MHC-antigen complex known or predicted to be expressed within a biological sample. In some cases, a CAR T-cell therapy is engineered or selected based at least in part on the spatial distribution of antigen and/or MHC expression in a biological sample. In some cases, a method of the disclosure comprises administering an engineered or selected CAR T-cell therapy to a subject.

A recombinant or CAR T-cell therapy of the disclosure can, in some instances, be a natural killer T (NKT) cell therapy. NKT cells are specialized T-cells. NKT cells can recognize lipid antigens presented on MHC proteins and can lead to activation of innate and adaptive immune cells in the tumor microenvironment. In some cases, a NKT cell therapy is engineered or selected based at least in part on the spatial distribution of antigen and/or MHC expression in a biological sample. In some cases, a method of the disclosure comprises administering an engineered or selected NKT cell therapy to a subject.

Cancer vaccines can treat cancer by activating a subject's immune system against cancer cells. Some cancer vaccines work by immunizing subjects against antigens expressed by cancer cells so that the immune system is stimulated to kill cancer cells expressing the antigen. In some cases, a subject can be immunized with an effective amount of an immunogen containing an effective amount of a particular antigen or MHC-antigen complex. In some cases, a subject can be immunized with precursors that will stimulate the subject's body produce an immune response to the antigen, such as through the use of synthetic peptides, self-replicating synthetic RNA, and viral vectors, which may be used alone or in combination.

In some cases, the antigen of the MHC-antigen complex is an epitope of antigen capable of binding to the MHC. In some embodiments, a cancer vaccine is engineered or selected to immunize a subject against a target antigen and/or MHC-antigen complex known or predicted to be expressed within a biological sample. In some cases, a cancer vaccine is engineered or selected based at least in part on the spatial distribution of antigen and/or MHC expression in a biological sample. In some cases, a method disclosed herein comprises administering an engineered or selected cancer vaccine to a subject.

Checkpoint inhibitors target immune checkpoints, immune system regulators that can dampen the immune response to a stimulus. Often, cancer cells evade destruction by immune cells by stimulating immune checkpoint targets, a process that can be reversed via the administration of checkpoint inhibitors. Non-limiting examples of molecules that can be targeted for inhibition by checkpoint inhibitors include CD25, PD-1 (CD279), PD-L1 (CD274, B7-H1), PD-L2 (CD273, B7-DC), CTLA-4, LAG3 (CD223), TIM3, 4-1BB (CD137), 4-1BBL (CD137L), GITR (TNFRSF18, AITR), CD40, CD40L, ICOS, ICOS-L, OX40 (CD134, TNFRSF4), OX40L, CXCR2, tumor associated antigens (TAA), B7-H3, B7-H4, BTLA, HVEM, GAL9, B7H3, B7H4, CD28, VISTA, CD27, CD30, STING, A2A adenosine receptor, KIR, and 2B4. In some instances, the effectiveness of a checkpoint inhibitor can be predicted based on the expression of antigens and/or MHC proteins by cancer cells. In some embodiments, a checkpoint inhibitor is selected based at least in part on the number of expected antigens within a biological sample. In some embodiments, a checkpoint inhibitor is selected based at least in part on an antigen, MHC protein, and/or MHC-antigen complex known or predicted to be expressed within a biological sample. In some cases, a checkpoint inhibitor is selected based at least in part on the spatial distribution of antigen and/or MHC expression in a biological sample. In some cases, a method disclosed herein comprises administering a selected checkpoint inhibitor to a subject.

Activated B-cells can induce specific T-cell responses directed towards cancer cell destruction. In some embodiments of a method disclosed herein, a B-cell therapy can be engineered or selected based at least in part on an antigen, MHC protein, and/or MHC-antigen complex known or predicted to be expressed within a biological sample. In some cases, a B-cell therapy is engineered or selected based at least in part on the spatial distribution of antigen and/or MHC expression in a biological sample. In some cases, a method of the disclosure comprises administering an engineered or selected B-cell therapy to a subject.

Variant Sequences and Alleles

Methods disclosed herein can analyze the spatial distribution of target sequences in a biological sample. In some cases, the identity and location of a target sequence can be determined using a probe molecule. For example, the method can comprise hybridizing a probe comprising a targeting sequence to a nucleic acid corresponding to a target sequence, identifying at least a portion of the probe, and determining a location of the target sequence within a biological sample by determining a location of the probe. In some cases, identifying and/or determining a location of the probe or at least a portion thereof comprises sequencing at least of portion of the probe in situ. In some cases, determining a location of a target sequence comprises identifying a target sequence. In some cases, a target sequence comprises a sequence of nucleotides. In some cases, a target sequence is part of a DNA molecule, cDNA molecule, RNA molecule, messenger ribonucleic acid (mRNA) molecule, transfer ribonucleic acid (tRNA) molecule, micro ribonucleic acid (miRNA) molecule, ribosomal ribonucleic acid (rRNA) molecule, small nucleolar ribonucleic acid (snoRNA) molecule, miRNA molecule, or a derivative of any of the foregoing. In some cases, a nucleic acid corresponding to a variant sequence is a DNA molecule, cDNA molecule, RNA molecule, mRNA molecule, miRNA molecule, rRNA molecule, snoRNA molecule, miRNA molecule, tRNA molecule, or a portion a portion or derivative of any of the foregoing.

In some cases, a target sequence is an HLA variant sequence. An HLA variant sequence can, in some instances, comprise an HLA allele. HLA genes can encode for MHC proteins and come in two forms class I and class II. In some instances, an HLA variant sequence is a class I or class II HLA allele. Class I HLA alleles encode class I MHC proteins and class II HLA alleles encode class II MHC proteins. MHC proteins are generally glycoproteins that contain a polymorphic antigen binding site or binding groove that can, in some cases, complex with peptide, including peptides processed by the cell machinery. A non-limiting example of a peptide that can complex with MHC proteins is an antigen such as a tumor antigen. In some cases, MHC molecules can be displayed or expressed on the cell surface, including as a complex with an antigen, i.e., MHC-antigen complex, for presentation of an antigen in a conformation recognizable by an antigen receptor on immune cells such as T-cells. Generally, MHC class I molecules are heterodimers having a membrane spanning a chain, in some cases with three alpha domains, and a non-covalently associated β2 microglobulin. Generally, MHC class II molecules are composed of two transmembrane glycoproteins, a and B, both of which can span the membrane. An MHC molecule can include an effective portion of an MHC that contains an antigen binding site or sites for binding a peptide and the sequences necessary for recognition by the appropriate antigen receptor. In some embodiments, MHC class I molecules deliver antigens originating in the cytosol to the cell surface, where a MHC-antigen complex is recognized by T cells, such as generally CD8+ T cells, but in some cases CD4+ T cells. In some embodiments, MHC class II molecules deliver antigens originating in the vesicular system to the cell surface, where they are generally recognized by CD4+ T-cells.

Expression of an HLA allele can affect MHC protein and antigen presentation on cells such as cancer cells. In some instances, an HLA variant sequence is an HLA allele. HLA alleles can be classified to a level of precision that ranges from a group of similar HLA molecules (e.g. HLA-A*02) to distinct proteins, coding sequences, nucleotide sequences, expression level (e.g. HLA-A*02:01:101:01:02N). Non-limiting examples of HLA alleles include HLA-A*01, HLA-A*02:01, HLA-A*02:01:01:03:04N, HLA-A*03:01, HLA-A*24:02, HLA-B*44:02, HLA-C*07:01, HLA-C*08:02, HLA-DPA1*01, HLA-DPB1*04:02, HLA-DQA1*01, HLA-DQB1*01, HLA DRB1*01, and HLA-DRA. In some embodiments, a method of the disclosure can assess the absence or spatial expression of one or more (e.g., 50, 100, 150, 200, 250, 300, 350, 400, 450, 500, 550, 1,000, 2,000, 3,000, 4,000, 5,000, 10,000, 100,000 or more) HLA alleles in a biological sample. For example, the method of the disclosure can assess the absence or spatial expression of a selection of clinically actionable target sequences (e.g., HLA variants). The absence or spatial expression of parental HLA alleles and/or modifications or mutants thereof can be assessed. The expression of corresponding MHC proteins can be predicted from HLA expression patterns. In some cases, a therapy (e.g., an immunotherapy) can be engineered or selected for treatment based on the spatial expression of one or more HLA alleles in a biological sample. Predictions on the spatial organization of MHC proteins or MHC-antigen complexes in a biological sample can be made based on predicted expression of HLA alleles. In some cases, a method of the disclosure comprises generating a visual representation (e.g., for display on a user interface, such as a graphical user interface) of HLA allele expression in a biological sample. In some cases, biological samples, such as blood and tissue needle aspirate, may not be analyzed in the context of an extracellular or tissue matrix structure, but have cellular structure, and the spatial expression comprises the observed or predicted cellular colocalization of MHC alleles and antigens.

A variant sequence of the disclosure can, in some cases, encode for, or be associated with, an antigen such as a tumor antigen. Tumor antigens are antigenic substances produced in tumor cells. Tumor antigens can trigger an immune response. Non-limiting examples of tumor antigens include tumor-specific antigens, tumor associated antigens, and neoantigens. Tumor-specific antigens are expressed on cancer cells, but not on healthy cells. Tumor-associated antigens can be expressed on both on cancerous and healthy cells. Neoantigens are antigens created due to tumor mutations. A method disclosed herein can comprise determining the location and identity of a target sequence that corresponds to or is associated with an antigen such as a tumor antigen. In some cases, a method disclosed herein comprises determining the identity and location of more than one target sequence, with each target sequence corresponding to or being associated with a tumor antigen, an HLA allele, or another sequence which can be used to infer the clonal structure of the tumor. For example, a method of the disclosure can determine the identity and location of a single neoantigen and its presenting HLA allele. In other cases, a method may determine the identity and location of hundreds or thousands of (e.g., at least about 10, 100, 1000, 10,000, 100,000 or more) target sequences. In these cases, targets may include identified antigens such as neoantigens, dozens or more nucleotide sequences that define each of the class I and II HLA alleles, sequences that can identify expressed cancer associated antigens, and hundreds or more expressed mutations that can be used together to help define and predict the clonal structure. In some instances, a method of the disclosure can determine the absence of hundreds or more target sequences. In some cases, the cancer samples may be highly mutated and hundreds of expressed somatic mutations may be identified, which can be used to inform clonal structure even if the specific antigen is not identified or is unknown. The absence or identity and location of one or more target sequences in a biological sample can be used to select or engineer a treatment such as an immunotherapy for a subject. In some cases, the selected or engineered treatment can be administered to the subject.

In some cases, a variant sequence comprises a mutation. Mutations can be associated with, for example, an increased risk of cancer or a neoantigen. Mutations can, in some instances, be tumor mutations.

Probe Design

Probe molecules can be designed to detect the presence or absence target sequences in a biological sample. In some cases, the presence, absence, and/or location of a target sequence can be determined via identification of a probe molecule or a portion thereof. Probe molecules can be designed to hybridize to nucleic acid molecules corresponding to variant sequence. A nucleic acid molecule can be, for example a DNA molecule, cDNA molecule, RNA molecule, mRNA molecule, RNA molecule, miRNA molecule, rRNA molecule, snoRNA molecule, miRNA molecule, or a derivative of any of the foregoing (e.g., an amplification product). In some embodiments, a method disclosed herein comprises reverse transcribing RNA to form cDNA, wherein the cDNA is a nucleic acid corresponding to a variant sequence. In some cases, a probe molecule hybridizes specifically to a variant sequence.

Figure 1:
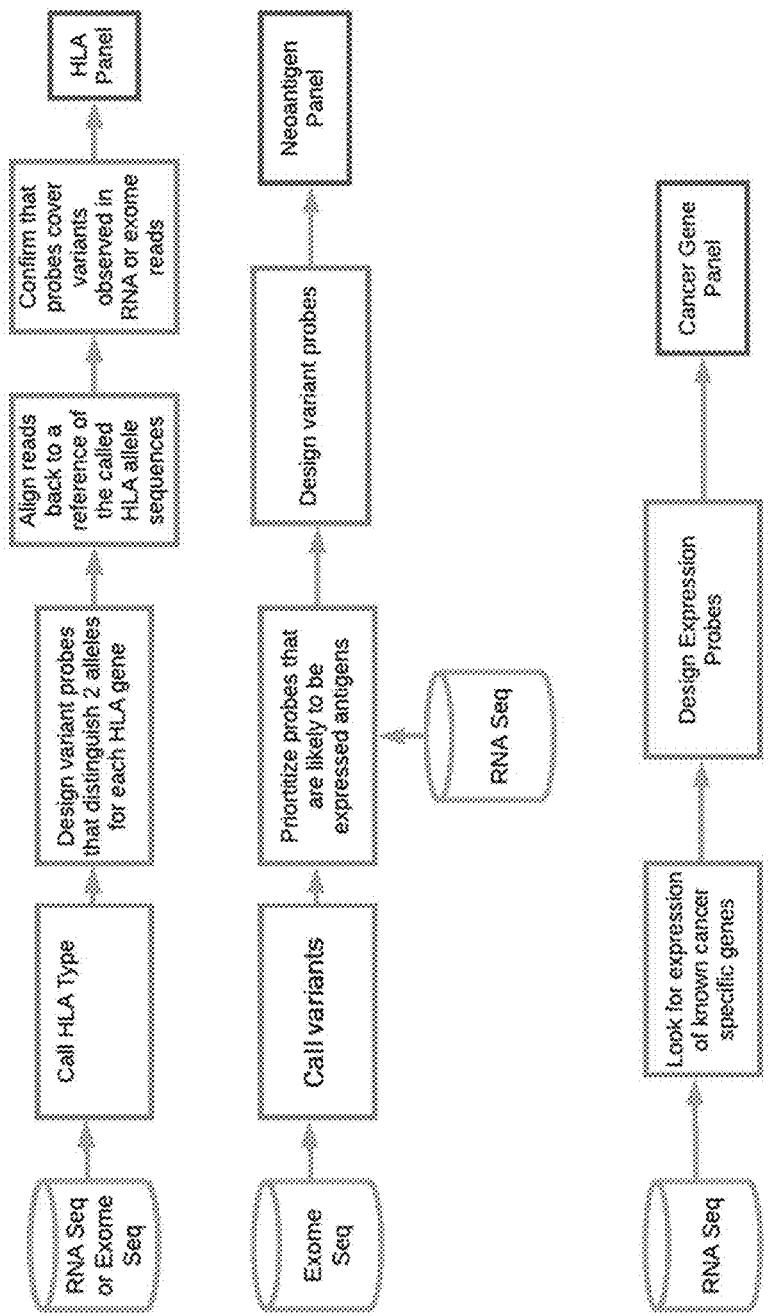
FIG. 1 shows a schematic of a workflow for generating genetic profiles.

Different HLA alleles and nucleotides associated with or encoding tumor antigens can have very similar nucleotide sequences. Similarities in nucleotide sequences can make designing probes that are specific for a single allele or gene difficult. Thus, in some cases probe molecules of the disclosure can discriminate between two or more nucleic acids corresponding to different variant sequences known to be present in a biological sample. In some cases, probes can be designed or selected based on characteristics known about the type of cancer to be treated. In some cases, probes can be designed or selected based on information learned about a subject. For example, a method of the disclosure can comprise generating a genetic profile of a subject from which a sample is obtained to identify a plurality of variant sequences (e.g. HLA variant sequences or sequences encoding antigen variants) present in the subject. In some cases, the genetic profile is obtained from a tumor or cancerous cells. In some cases, the genetic profile is generated from healthy tissue in a subject. For example, a genetic profile may be generated from healthy tissue in a subject with a tumor so that it can be compared to the genetic profile of the tumor. Genetic profiles can be generated via, for example, microarrays, next generation sequencing, single cell sequencing of tissues, RNA sequencing, exome sequencing, or whole genome sequencing. In some instances, genetic profiles can be used to identify a plurality of variant sequences present in a biological sample to spatially analyze. In some instances, genetic profiles can be used to identify any mutations present in a biological sample. In some cases, the mutation(s) identified can be used to predict any associated antigen(s). In some embodiments, an antigen prediction algorithm can be used to identify a mutation and an associated antigen. Probe molecules can be designed or selected to discriminate between two nucleic acid molecules corresponding to sequences of the plurality of variant sequences identified and/or to preferentially hybridize to a nucleic acid molecule corresponding to only one of the identified variant sequences. An example of such a process is depicted in FIG. 1. An example of designing a probe to focus on the discrimination of two different HLA alleles known to be present in a sample is shown in FIG. 2, with bolded alleles representing alleles identified in a biological sample, and non-bolded alleles representing similar alleles that were not detected in the sample. Probes may be designed based on population-level or clinical cohort sequencing datasets, such as from "cancer atlas" databases, to target variants present at more than 1 variant in the cohort, or based on a percent frequency, such as 0.1%, 1%, 2%, 5%, 10%, or more.

Samples

Any suitable biological sample that comprises nucleic acid may be obtained from a subject. Any suitable biological sample that comprises nucleic acid may be used in the methods and systems described herein. A biological sample may be solid matter (e.g., biological tissue) or may be a fluid (e.g., a biological fluid). In general, a biological fluid can include any fluid associated with living organisms. Non-limiting examples of a biological sample include blood (or components of blood—e.g., white blood cells, red blood cells, platelets) obtained from any anatomical location (e.g., tissue, circulatory system, bone marrow) of a subject, and cells or tissue obtained from any anatomical location of a subject such as skin, heart tissue, lung tissue, kidney tissue, breath, bone marrow, stool, semen, vaginal fluid, interstitial fluids derived from tumorous tissue, breast tissue, pancreatic tissue, cerebral spinal fluid, throat swab, biopsies, placental fluid, amniotic fluid, liver tissue, muscle, smooth muscle, bladder tissue, gall bladder tissue, colonic tissue, intestinal tissue, brain tissue, cavity fluids, sputum, pus, micropiota, meconium, breast milk, prostate tissue, esophageal tissue, thyroid tissue, serum, saliva, urine, gastric and digestive fluid, tears, ocular fluids, sweat, mucus, earwax, oil, glandular secretions, spinal fluid, hair, fingernails, plasma, nasal swab or nasopharyngeal wash, spinal fluid, cord blood, emphatic fluids, and/or other excretions or body tissues. A biological sample may be a cell-free sample. Such cell-free sample may include DNA and/or RNA.

Additionally, biological samples of the disclosure include, without limitation, cells, populations of cells, needle or fine needle aspirates, tissue biopsies, tissue sections, tumor biopsies, biological tissues, surgical resections, tumors, and cancer cells. In some embodiments, methods disclosed herein analyze the spatial distribution of variant sequences in cancer/tumor samples, aid in the selection of treatment of cancer, and/or administer therapies for cancer treatment. Non-limiting examples of cancers disclosed herein include a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synoviorna, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma. In some instances, a biological sample is derived from healthy tissue. For example, a biological tissue can be derived from a healthy control tissue from a subject with cancer.

Construction of the 3D Matrix

Methods disclosed herein may comprise providing a biological sample such as tumor tissue a or derivative thereof within a 3D matrix prior to contacting the sample with a probe molecule. An in situ 3D matrix can be formed from an original biological specimen using a number of approaches described herein. Formation of the 3D matrix can cause the termination of in vivo biochemical processes, substantially preserving spatial information within the biological sample such as the spatial information of the nucleic acid molecules and other sub-cellular components. Common methods for forming the 3D matrix from a biological specimen can include fixation, or the formation of chemical (via covalent bonds) or physical (via weak interactions) crosslinks among the 3D matrix of biomolecules, such as by temperature, electromagnetic radiation (e.g., microwave), or chemicals, such as formaldehyde, glutaraldehyde, or other material for biological sample fixation, within the cell and tissue. Any convenient fixation agent, or "fixative," may be used to fix the biological sample in the absence or in the presence of hydrogel subunits, for example, formaldehyde, paraformaldehyde, glutaraldehyde, acetone, ethanol, methanol, formalin, osmium tetroxide, etc. In some cases, the fixative may be diluted in a buffer, e.g., saline, phosphate buffer (PB), phosphate buffered saline (PBS), citric acid buffer, potassium phosphate buffer, etc., usually at a concentration of 1-10%, e.g., about 1%, 2%, 3%, 4%, 5%, 6%, 7%, 8%, or 10%, for example, 4% paraformaldehyde/0.1M phosphate buffer; 2% paraformaldehyde/0.2% picric acid/0.1M phosphate buffer; 4% paraformaldehyde/0.2% periodate/1.2% lysine in 0.1 M phosphate buffer; 4% paraformaldehyde/0.05% glutaraldehyde in phosphate buffer; etc. The type of fixative used and the duration of exposure to the fixative will depend on the sensitivity of the molecules of interest in the specimen to denaturation by the fixative and may be readily determined using histochemical or immunohistochemical techniques.

Alternatively, or in addition to the process of fixation, a tissue-chemical hydrogel may be formed by generation of chemical or physical crosslinks between biomolecules and other natural or synthetic components added to the sample to supplement or replace native cellular components for the purpose of immobilizing biomolecules. The chemical 3D matrix can comprise a polymeric compound. A 3D matrix may be formed in situ throughout the cell and tissue sample, such as through the formation of a hydrogel matrix. A hydrogel matrix may be formed upon cross-linking, gelling, or polymerizing subunits, such as, for example, cross-linking, gelling or polymerizing a polyacrylamide or polyethylene glycol (PEG). The 3D matrix may be generated by directing precursors of the 3D matrix into the biological specimen and subjecting the precursors to crosslinking or polymerization reactions. For example, acrylamide may be directed into the biological specimen and polymerized to form polyacrylamide. Further according to this embodiment, the chemical matrix can be composed substantially of polyacrylamide. According to another embodiment, the 3D matrix can be an expanding FISSEQ matrix, such as one comprised substantially of poly(acrylate-co-acrylic acid) (PAA) or Poly(N-isopropylacrylamide) (NIPAM). The matrix comprising NIPAM may be expandable or configured to expand by a change in temperature. According to another embodiment, the 3D matrix can be composed substantially of cross-linked poly-ethylene-glycol (PEG). The PEG can be of various molecular weights.

The 3D matrix may be formed by various processes such as via free-radical polymerization, chemical conjugation and bioconjugation reactions. For example, the reaction between a primary amine and N-hydroxysuccinimide esters or between thiols and maleimides or other chemical mechanisms may be used to form the 3D matrix. Aggregation and non-covalent mechanism may also be used to generate the 3D matrix.

The 3D matrix may be formed using a photopolymerization. Photopolymerization may use photons to initiate a polymerization reaction. The photopolymerization reaction may be initiated by a single-photon or a multiphoton excitation system as described elsewhere herein. Light may be manipulated such to form specific two dimensional (2D) or 3D patterns and be used to initiate the photopolymerization reaction. This may be used to construct a particular shape or pattern for the 3D matrix such that the matrix is generated in one part of the cell or cell derivative but not generated in another part of the cell or cell derivative. Light and patterns of light may be generated by spatial light modulators, such as a digital spatial light modulator. The spatial light modulators may employ a transmissive liquid crystal, reflective liquid crystal on silicon (LCOS), digital light processing, a digital micromirror device (DMD), or a combination thereof.

The fixative/hydrogel composition may comprise any hydrogel subunits, such as, but not limited to, poly(ethylene glycol) and derivatives thereof (e.g., PEG-diacrylate (PEG-DA), PEG-RGD), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly (hydroxyethyl methacrylate), collagen, hyaluronic acid, chitosan, dextran, agarose, gelatin, alginate, protein polymers, methylcellulose and the like. Agents such as hydrophilic nanoparticles, e.g., poly-lactic acid (PLA), poly-glycolic acid (PLG), poly(lactic-co-glycolic acid) (PLGA), polystyrene, poly(dimethylsiloxane) (PDMS), etc. may be used to improve the permeability of the hydrogel while maintaining patternability. Materials such as block copolymers of PEG, degradable PEO, poly(lactic acid) (PLA), and other similar materials can be used to add specific properties to the hydrogel. Crosslinkers (e.g., bis-acrylamide, diazirine, etc.) and initiators (e.g., azobisisobutyronitrile (AIBN), riboflavin, L-arginine, etc.) may be included to promote covalent bonding between interacting macromolecules in later polymerization operations.

Nucleic acids (e.g., RNA molecules, DNA molecules, cDNA molecules, primers, probes, padlock probes) disclosed herein can comprise functional moieties which can be used to link the nucleic acid molecules to a 3D matrix. The functional moiety can be reacted with a reactive group on the 3D matrix through conjugation chemistry. In some cases, the functional moiety can be attached to a target of interest through conjugation chemistry. In some cases, the functional moiety can be directly attached to a reactive group on the native nucleic acid molecule. In some cases, the functional moiety can be indirectly linked to a target through an intermediate chemical or group. The conjugation approaches described herein are not limited to nucleic acid targets and can be used for protein or small molecule targets as well. A nucleotide analog comprising a functional moiety may be incorporated into a growing chain of the nucleic acid (e.g., cDNA molecule, probe, or primer) during nucleic acid synthesis or an extension reaction.

As used herein, the term "reactive group" or "functional moiety" generally refers to any moiety on a first reactant that is capable of reacting chemically with another functional moiety or reactive group on a second reactant to form a covalent or ionic linkage. "Reactive group" and "functional moiety" may be used interchangeably. For example, a reactive group of the monomer or polymer of the matrix-forming material can react chemically with a functional moiety (or another reactive group) on the substrate of interest or the target to form a covalent or ionic linkage. The substrate of interest or the target may then be immobilized to the matrix via the linkage formed by the reactive group and the functional moiety. Examples of suitable reactive groups or functional moieties include electrophiles or nucleophiles that can form a covalent linkage by reaction with a corresponding nucleophile or electrophile, respectively, on the substrate of interest. Non-limiting examples of suitable electrophilic reactive groups may include, for example, esters including activated esters (such as, for example, succinimidyl esters), amides, acrylamides, acridines, acyl azides, acyl halides, acyl nitriles, aldehydes, ketones, alkyl halides, alkyl sulfonates, anhydrides, aryl halides, aziridines, boronates, carbodiimides, diazoalkanes, epoxides, haloacetamides, haloplatinates, halotriazines, imido esters, isocyanates, isothiocyanates, maleimides, phosphoramidites, silyl halides, sulfonate esters, sulfonyl halides, and the like. Non-limiting examples of suitable nucleophilic reactive groups may include, for example, amines, anilines, thiols, alcohols, phenols, hyrazines, hydroxylamines, carboxylic acids, glycols, heterocycles, and the like.

Further according to these aspects of the present disclosure, endogenous or exogenous biomolecules, especially nucleic acids, may be covalently or noncovalently linked to the 3D matrix, preserving the spatial origin of the molecules during sample processing. The nucleic acid molecules or derivatives thereof can be coupled to the 3D matrix by coupling agents. To facilitate coupling or other downstream processes, endogenous nucleic acids may be modified using chemical reactions, such as alkylation, oxymercuration, periodate oxidation of RNA 3' vicinal diols, carbodiimide activation of RNA and DNA 5' phosphate, or by other nucleic-acid reactive chemistries such as psoralen and phenyl azide, for functional attachment of acryloyl or click-reactive moieties, which may be subsequently reacted with the 3D matrix. Alternatively, endogenous nucleic acids may be modified using biochemical reactions, such as ligation, polymerase extension, and hybridization, for functional attachment of acryloyl or click-reactive moieties, which may be subsequently reacted with the 3D matrix. For example, a DNA molecule may be ligated using a DNA ligase to attach the 3D matrix to the DNA molecule. The coupling reaction may couple probes or sequences comprising a identifier nucleotide sequence to the 3D matrix or may couple sequences to the 3D matrix that are associated with probes or a identifier nucleotide sequence.

Reference to the 3D matrix may be understood to be inclusive of a number of matrix compositions, including those comprised of biomolecules, synthetic polymers, hydrogels, or combinations thereof. An intermediate or final 3D matrix composition may comprise multiple independently formed matrixes, such as re-embedded hydrogels, or other forms of spatially coincident, or in situ, 3D matrix(es).

Further according to these aspects of the present disclosure, the synthetic 3D matrix may be partially or substantially cleared of certain species or classes of biomolecules, such as lipids and proteins, as by use of detergent and/or protease reagents. According to some aspects of the present disclosure, the sample can be cleared using a detergent solution, such as Triton™ X-100 (2-[4-(2,4,4-trimethylpentan-2-yl) phenoxy]ethanol) or sodium dodecyl sulfate (SDS). The detergent may interact with the molecules allowing the molecules to be washed out or removed. Other non-limiting examples of detergents include Triton™ X-100 (2-[4-(2,4,4-trimethylpentan-2-yl) phenoxy]ethanol), Triton™ X-114 (2-[4-(2,4,4-trimethylpentan-2-yl) phenoxy]ethanol), Tween® 20 (Polyoxyethylene (20) sorbitan monolaurate), Tween® 80 (Polyoxyethylene (20) sorbitan monooleate), saponin, 3-[(3-cholamidopropyl)dimethylammonio]-1-propanesulfonate (CHAPS), and NP-40. According to some aspects of the present disclosure, the sample can be cleared using a protease reaction, such as Proteinase K. The protease may cleave or digest proteins such that the fragments or amino acids can be removed. According to some aspects of the present disclosure, the extracellular matrix can be substantially cleared using one or more specific or non-specific proteases. Other non-limiting examples of protease include trypsin, chemotrypsin, papain, thrombin, and pepsin.

The synthetic 3D matrix may be immobilized onto a solid substrate, such as glass or plastic, facilitating handling and reagent exchange. According to one aspect, the 3D matrix can be affixed to a glass slide via oxysilane-functionalization with acrylamide- or free-radical-polymerizing groups, such as methacryloxypropyltrimethoxysilane. The 3D matrix may be free-floating or otherwise not attached to a solid substrate.

A matrix may be used in conjunction with a solid support. For example, the matrix can be polymerized in such a way that one surface of the matrix is attached to a solid support (e.g., a glass surface, a flow cell, a glass slide, a well), while the other surface of the matrix is exposed or sandwiched between two solid supports. According to some aspects of the present disclosure, the matrix can be contained within a container. In some cases, the biological sample may be fixed or immobilized on a solid support.

Solid supports of the present disclosure may be fashioned into a variety of shapes. In certain embodiments, the solid support is substantially planar. Examples of solid supports include plates such as slides, microtitre plates, flow cells, coverslips, microchips, and the like, containers such as microfuge tubes, test tubes and the like, tubing, sheets, pads, films and the like. Additionally, the solid supports may be, for example, biological, nonbiological, organic, inorganic, or a combination thereof.

The term "solid surface" or "solid support," as used herein, refers to the surface of a solid support or substrate and includes any material that can serve as a solid or semi-solid foundation for attachment of a biological sample such as polynucleotides, amplicons (i.e., amplification products), DNA balls, other nucleic acids and/or other polymers, including biopolymers. Examples of materials comprising solid surfaces include glass, modified glass, functionalized glass, inorganic glasses, microspheres, including inert and/or magnetic particles, plastics, polysaccharides, nylon, nitrocellulose, ceramics, resins, silica, silica-based materials, carbon, metals, an optical fiber or optical fiber bundles, a variety of polymers other than those exemplified above and multi-well micro tier plates. Examples of plastics include acrylics, polystyrene, copolymers of styrene and other materials, polypropylene, polyethylene, polybutylene, polyurethanes and Teflon™. Examples of silica-based materials include silicon and various forms of modified silicon.

Solid surfaces can also be varied in their shape depending on the application in a method described herein. For example, a solid surface useful in the present disclosure can be planar or contain regions that are concave or convex.

Computer Systems

The present disclosure provides computer systems that are programmed to implement methods of the disclosure. FIG. 3 shows a computer system 301 that is programmed or otherwise configured to aid in designing probes, engineering immunotherapies, selecting immunotherapies for administration to a subject, predicting MHC-antigen complex presentation, processing sequencing reads, sequencing nucleic acids, or constructing visual representations of HLA expression, antigen expression, MHC expression, or MHC-antigen presentation within a biological sample. The computer system 301 can regulate various aspects of the present disclosure, such as, for example, store data relating to 3D spatial positions of nucleic acids (e.g., probes, amplification products, rolonies, etc.), align sequencing reads, map nucleic acid locations, and generate outputs regarding spatial positions. In some aspects, the computer system may be programmed to control release of reagents, activation of reactions (e.g., amplification reactions), and/or may initiate a sequencing reaction to take place. The computer system 301 can be an electronic device of a user or a computer system that is remotely located with respect to the electronic device. The electronic device can be a mobile electronic device.

The computer system 301 includes a central processing unit (CPU, also "processor" and "computer processor" herein) 305, which can be a single core or multi core processor, or a plurality of processors for parallel processing. The computer system 301 also includes memory or memory location 310 (e.g., random-access memory, read-only memory, flash memory), electronic storage unit 315 (e.g., hard disk), communication interface 320 (e.g., network adapter) for communicating with one or more other systems, and peripheral devices 325, such as cache, other memory, data storage and/or electronic display adapters. The memory 310, storage unit 315, interface 320 and peripheral devices 325 are in communication with the CPU 305 through a communication bus (solid lines), such as a motherboard. The storage unit 315 can be a data storage unit (or data repository) for storing data. The computer system 301 can be operatively coupled to a computer network ("network") 330 with the aid of the communication interface 320. The network 330 can be the Internet, an internet and/or extranet, or an intranet and/or extranet that is in communication with the Internet. The network 330 in some cases is a telecommunication and/or data network. The network 330 can include one or more computer servers, which can enable distributed computing, such as cloud computing. The network 330, in some cases with the aid of the computer system 301, can implement a peer-to-peer network, which may enable devices coupled to the computer system 301 to behave as a client or a server.

The CPU 305 can execute a sequence of machine-readable instructions, which can be embodied in a program or software. The instructions may be stored in a memory location, such as the memory 310. The instructions can be directed to the CPU 305, which can subsequently program or otherwise configure the CPU 305 to implement methods of the present disclosure. Examples of operations performed by the CPU 305 can include fetch, decode, execute, and writeback.

The CPU 305 can be part of a circuit, such as an integrated circuit. One or more other components of the system 301 can be included in the circuit. In some cases, the circuit is an application specific integrated circuit (ASIC).

The storage unit 315 can store files, such as drivers, libraries and saved programs. The storage unit 315 can store user data, e.g., user preferences and user programs. The computer system 301 in some cases can include one or more additional data storage units that are external to the computer system 301, such as located on a remote server that is in communication with the computer system 301 through an intranet or the Internet.

The computer system 301 can communicate with one or more remote computer systems through the network 330. For instance, the computer system 301 can communicate with a remote computer system of a user (e.g., a user generating the indices of the current disclosure or a user utilizing such indices). Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), personal digital assistants, or cloud systems (e.g. Amazon AWS). The user can access the computer system 301 via the network 330.

Methods as described herein can be implemented by way of machine (e.g., computer processor) executable code stored on an electronic storage location of the computer system 301, such as, for example, on the memory 310 or electronic storage unit 315. The machine executable or machine-readable code can be provided in the form of software. During use, the code can be executed by the processor 305. In some cases, the code can be retrieved from the storage unit 315 and stored on the memory 310 for ready access by the processor 305. In some situations, the electronic storage unit 315 can be precluded, and machine-executable instructions are stored on memory 310.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 301, can be embodied in programming. Various aspects of the technology may be thought of as "products" or "articles of manufacture" in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 301 can include or be in communication with an electronic display 335 that comprises a user interface (UI) 340. In some instances, the US can provide the spatial origin of nucleic acid molecules, show the detection and/or sequencing of biomolecules of interest, or generate or display an electronic report associating the 3D spatial position with a sequence of a nucleic acid molecule. Examples of UI's include, without limitation, a graphical user interface (GUI) and web-based user interface.

In some embodiments, data including the spatial origin/position of nucleic acid molecules detected may be generated and compiled (e.g., in a clinical "report"). In some embodiments, the data may be processed by computer algorithm or with human assistance, e.g., by an oncologist, clinical genomicist, or pathologist, into a concise representation of the presence and/or absence of variants and clonality thereof within the tumor and with respect to histological tissue features, when present, such as by reference to databases, for the purpose of distilling clinically actionable or potentially actionable aspects of the high-dimensional data for the purpose of diagnosis, prognosis, or therapeutic guidance. The report may be presented in analog or digital form, in the latter embodiment, may include interactive graphical user interface features for the purpose of visualization and performing statistical analysis with respect to the patient sample and/or external datasets.

Methods and systems of the present disclosure can be implemented by way of one or more algorithms. An algorithm can be implemented by way of software upon execution by the central processing unit 305. The algorithm can, for example, be executed to generate the indices of the current disclosure, or map and align sequencing reads to identify a spatial origin of a given sequence.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It may be understood that the description in range format is merely for convenience and brevity and may not be construed as an inflexible limitation on the scope of the disclosure. Accordingly, the description of a range can be considered to have specifically disclosed all the possible subranges as well as individual numerical values within that range. For example, description of a range such as from 1 to 6 can be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular form "a", "an" or "the" includes plural references unless the context clearly dictates otherwise. For example, the term "a cell" includes a plurality of cells, including mixtures thereof.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the term "about" a number refers to that number plus or minus 10% of that number. The term "about" a range refers to that range minus 10% of its lowest value and plus 10% of its greatest value.

As used herein, the terms "amplifying" and "amplification" generally refer to generating an extension product or one or more copies (or "amplified product" or "amplification product") of a nucleic acid. The one or more copies may be generated by nucleic acid extension. Such extension may be a single round of extension or multiple rounds of extension. The amplified product may be generated by polymerase chain reaction (PCR).

The term "rolony," as used herein, generally refers to a rolling circle colony, such as, for example, a colony of nucleic acid molecules generated by rolling circle amplification (RCA).

The term "nucleic acid," as used herein, generally refers to a polymeric form of nucleotides of any length. A nucleic acid may comprise either deoxyribonucleotides (dNTPs) or ribonucleotides (rNTPs), or analogs thereof. A nucleic acid may be an oligonucleotide or a polynucleotide. Nucleic acids may have any three-dimensional structure and may perform any function. Non-limiting examples of nucleic acids include DNA, RNA, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation, with a functional moiety for immobilization.

As used herein, the term "subject," generally refers to an entity or a medium that has testable or detectable genetic information. A subject can be a person or an individual. A subject can be a vertebrate, such as, for example, a mammal. Non-limiting examples of mammals include murines, simians, and humans. A subject may be an animal, such as a farm animal. A subject may be a pet, such as dog, cat, mouse, rat, or bird. Other examples of subjects include food, plant, soil, and water. A subject may be displaying a disease. As an alternative, the subject may be asymptomatic.

The section headings used herein are for organizational purposes only and are not to be construed as limiting the subject matter described.

Embodiments

The following non-limiting embodiments provide illustrative examples of the disclosure, but do not limit the scope of the disclosure.

Embodiment 1. A method of analyzing a spatial distribution of a first human leukocyte antigen (HLA) variant sequence in a biological sample comprising:
(a) obtaining a biological sample comprising a nucleic acid corresponding to the first HLA variant sequence from a subject;
(b) hybridizing a first probe comprising an HLA targeting sequence to the nucleic acid corresponding to the first HLA variant sequence;
(c) identifying at least a portion of the first probe; and
(d) determining a location of the first HLA variant sequence within the biological sample by determining a location of the first probe.

Embodiment 2. The method of embodiment 1, wherein identifying at least a portion of the first probe comprises sequencing at least a portion of the first probe in situ.

Embodiment 3. The method of embodiment 1 or 2, wherein determining a location of the first probe comprises sequencing at least a portion of the first probe in situ.

Embodiment 4. The method of any one of embodiments 1-3, wherein determining a location of the first HLA variant sequence further comprises identifying the first HLA variant sequence.

Embodiment 5. The method of embodiment 4, wherein the first HLA variant sequence comprises an HLA allele.

Embodiment 6. The method of embodiment 4 or 5, wherein identifying the first HLA variant sequence comprises identifying the first probe.

Embodiment 7. The method of any one of embodiments 1-6, further comprising providing the biological sample within a three-dimensional (3D) matrix that preserves spatial information of the first HLA variant sequence prior to operations (c) and (d).

Embodiment 8. The method of embodiment 7, wherein providing the biological sample within the 3D matrix comprises generating the 3D matrix.

Embodiment 9. The method of embodiment 7 or 8, further comprising immobilizing the first probe on the 3D matrix.

Embodiment 10. The method of any one of embodiments 7-9, further comprising immobilizing the nucleic acid corresponding to the first HLA variant sequence on the 3D matrix.

Embodiment 11. The method of any one of embodiments 7-10, wherein the biological sample is provided within the 3D matrix by directing a precursor of the 3D matrix through the biological sample and subjecting the precursor of the 3D matrix to a reaction to generate cross-links and form the 3D matrix.

Embodiment 12. The method of embodiment 11, wherein the cross-links comprise chemical crosslinks.

Embodiment 13. The method of embodiment 11, wherein the cross-links comprise physical crosslinks.

Embodiment 14. The method of embodiment 11, wherein the reaction comprises free-radical polymerization.

Embodiment 15. The method of embodiment 11, wherein the reaction comprises a chemical conjugation reaction.

Embodiment 16. The method of embodiment 11, wherein the reaction comprises a bioconjugation reaction.

Embodiment 17. The method of embodiment 11, wherein the reaction comprises a photopolymerization reaction.

Embodiment 18. The method of any one of embodiments 1-17, wherein the biological sample comprises a second nucleic acid corresponding to a second variant sequence and the method further comprises:
(A) hybridizing a second probe comprising a second nucleic acid targeting sequence to the second nucleic acid corresponding to the second variant sequence;
(B) identifying at least a portion of the second probe; and
(C) determining a location of the second variant sequence within the biological sample by determining a location of the second probe.

Embodiment 19. The method of embodiment 18, wherein the second variant sequence comprises a mutation.

Embodiment 20. The method of embodiment 19, wherein the mutation is associated with an increased risk of cancer.

Embodiment 21. The method of embodiment 19, wherein the mutation is associated with a tumor antigen.

Embodiment 22. The method of embodiment 19, wherein the mutation is associated with a cancer/testis antigen.

Embodiment 23. The method of embodiment 19, wherein the mutation is associated with an oncofetal protein.

Embodiment 24. The method of embodiment 19, wherein the mutation is a tumor mutation.

Embodiment 25. The method of embodiment 19, wherein the mutation is associated with a tumor suppressor protein.

Embodiment 26. The method of embodiment 19, wherein the mutation is associated with a neoantigen.

Embodiment 27. The method of any one of embodiments 18-26, further comprising generating a visual representation of the location of the first HLA variant sequence and the location of the second variant sequence for display on a graphical user interface (GUI).

Embodiment 28. The method of any one of embodiments 18-26, further comprising detecting a clone within the biological sample by comparing the location of the first HLA variant sequence and the location of the second variant sequence.

Embodiment 29. The method of embodiment 28, further comprising generating a visual representation of the location of the clone within the biological sample for display on a graphical user interface (GUI).

Embodiment 30. The method of any one of embodiments 18-29, further comprising identifying a cell or derivative thereof within the biological sample, wherein the cell derivative thereof comprises the first HLA variant sequence and the second variant sequence.

Embodiment 31. The method of any one of embodiments 18-30, further comprising predicting the presentation of a peptide on a major histocompatibility complex (MHC) protein expressed in the biological sample, wherein the peptide is at least partially encoded by the second variant sequence and the MHC protein is at least partially encoded by the HLA variant sequence.

Embodiment 32. The method of embodiment 31, wherein the peptide is a mutant peptide.

Embodiment 33. The method of embodiment 31 or 32, wherein the peptide is associated with an increased risk of cancer.

Embodiment 34. The method of any one of embodiments 31-33, further comprising selecting a treatment to be administered to the subject, wherein:
the treatment comprises administration of a cell to the subject; and
the cell comprises a cell receptor that recognizes the peptide on the MHC protein expressed in the biological sample.

Embodiment 35. The method of embodiment 34, wherein the cell is a T-cell, a B cell, or an natural killer T (NKT) cell.

Embodiment 36. The method of embodiment 34, wherein the cell is a recombinant T-cell.

Embodiment 37. The method of any one of embodiments 34-36, wherein the cell expresses a chimeric antigen receptor.

Embodiment 38. The method of any one of embodiments 33-35, wherein the cell expresses a recombinant T cell receptor.

Embodiment 39. The method of any one of embodiments 31-38, further comprising selecting a treatment to be administered to the subject, wherein the treatment is more likely to be effective in a subject with one or more cancer cells presenting the peptide on the MHC protein expressed in the biological sample than it is in a subject without the one or more cancer cells that present the peptide on the MHC protein expressed in the biological sample.

Embodiment 40. The method of embodiment 39, wherein the treatment is an immunotherapy.

Embodiment 41. The method of embodiment 39 or embodiment 40, wherein the treatment comprises administration of a checkpoint inhibitor to the subject.

Embodiment 42. The method of any one of embodiments 31-41, further comprising selecting a treatment to be administered to the subject, wherein:
the treatment comprises administration of the peptide; and
the treatment is more likely to be effective in a subject with one or more cancer cells expressing the MHC protein expressed in the biological sample than it is in a subject without one or more cancer cells that express the MHC protein.

Embodiment 43. The method of any one of embodiments 1-42, wherein the biological sample further comprises a third nucleic acid, and wherein the third nucleic acid corresponds to a second HLA variant sequence, the method further comprising:
(1) hybridizing a third probe comprising a second HLA targeting sequence to the third nucleic acid;
(2) identifying at least a portion of the third probe; and
(3) determining a location of the second HLA variant sequence within the biological sample by determining a location of the third probe.

Embodiment 44. The method of any one of embodiments 1-43, further comprising, prior to operation (b):
(I) obtaining a genetic profile of the subject;
(II) detecting a presence or absence of a first HLA allele in the subject by analyzing the genetic profile.

Embodiment 45. The method of embodiment 44, wherein the first HLA variant sequence comprises the first HLA allele detected in the genetic profile.

Embodiment 46. The method of embodiment 44, wherein the first HLA allele comprises a mutation.

Embodiment 47. The method of embodiment 44, wherein the first HLA allele is a gene variant.

Embodiment 48. The method of any one of embodiments 1-43, further comprising identifying a first group of HLA alleles, wherein the first group of HLA alleles are expressed in the biological sample, and wherein the first probe is designed to hybridize to a nucleic acid corresponding to one of the HLA alleles of the first group of alleles.

Embodiment 49. The method of embodiment 48, wherein the first probe discriminates between two alleles of the first group of HLA alleles.

Embodiment 50. The method of any one of embodiments 1-43, further comprising, prior to operation (b):
(I) obtaining a genetic profile of the subject;
(II) detecting a plurality of HLA alleles in the subject by analyzing the genetic profile; wherein the first probe preferentially hybridizes to a nucleic acid corresponding to only one of the HLA alleles detected in the genetic profile.

Embodiment 51. The method of any one of embodiments 44-50, wherein the genetic profile is generated via RNA sequencing.

Embodiment 52. The method of any one of embodiments 44-50, wherein the genetic profile is generated via exome sequencing.

Embodiment 53. The method of any one of embodiments 1-52, wherein the first HLA variant sequence is a class I HLA allele.

Embodiment 54. The method of any one of embodiments 1-52, wherein the first HLA variant sequence is a class II HLA allele.

Embodiment 55. The method of any one of embodiments 1-52, wherein the first HLA variant sequence is HLA-A*01:01.

Embodiment 56. The method of any one of embodiments 1-52, wherein the first HLA variant sequence is HLA-A*02:01.

Embodiment 57. The method of any one of embodiments 1-52, wherein the first HLA variant sequence is HLA-B*44:02.

Embodiment 58. The method of any one of embodiments 1-52, wherein the first HLA variant sequence is HLA-C*07:01.

Embodiment 59. The method of any one of embodiments 1-52, wherein the first HLA variant sequence is HLA-C*08:02.

Embodiment 60. The method of any one of embodiments 1-52, wherein the first HLA variant sequence is HLA-DPA1.

Embodiment 61. The method of any one of embodiments 1-52, wherein the first HLA variant sequence is HLA-DPB1*01.

Embodiment 62. The method of any one of embodiments 1-52, wherein the first HLA variant sequence is HLA-DQA1.

Embodiment 63. The method of any one of embodiments 1-52, wherein the first HLA variant sequence is HLA-DQB1.

Embodiment 64. The method of any one of embodiments 1-52, wherein the first HLA variant sequence is HLA DRB1.

Embodiment 65. The method of any one of embodiments 1-52, wherein the first HLA variant sequence is HLA-DRA.

Embodiment 66. The method of any one of embodiments 1-65, wherein the nucleic acid corresponding to the first HLA variant sequence is a DNA molecule.

Embodiment 67. The method of any one of embodiments 1-65, wherein the nucleic acid corresponding to the first HLA variant sequence is an RNA molecule.

Embodiment 68. The method of any one of embodiments 1-66, further comprising, prior to operation (b), reverse transcribing RNA expressed in the biological sample to form cDNA, wherein the cDNA comprises the nucleic acid corresponding to the first HLA variant sequence.

Embodiment 69. The method of any one of embodiments 1-68, wherein the biological sample is a tissue biopsy.

Embodiment 70. The method of any one of embodiments 1-68, wherein the biological sample is a tumor biopsy.

Embodiment 71. The method of any one of embodiments 1-68, wherein the biological sample is biological tissue.

Embodiment 72. The method of any one of embodiments 1-68, wherein the biological sample is a surgical resection.

Embodiment 73. The method of any one of embodiments 1-68, wherein the biological sample is a tumor.

Embodiment 74. The method of any one of embodiments 1-68, wherein the biological sample is a blood sample.

Embodiment 75. The method of any one of embodiments 1-73, further comprising, prior to operation (b), generating a section, wherein the section comprises a portion of the biological sample.

Embodiment 76. The method of any one of embodiments 1-74, further comprising, prior to operation (c) subjecting the first probe to an amplification reaction to generate an amplified nucleic acid molecule that corresponds to the first HLA variant sequence.

Embodiment 77. The method of embodiment 75, wherein identifying at least a portion of the first probe comprises identifying at least a portion of the amplified nucleic acid molecule.

Embodiment 78. The method of embodiment 75 or 76, wherein determining the location of the first probe comprises determining a location of the amplified nucleic acid molecule.

Embodiment 79. The method of any one of embodiments 7-77, further comprising, prior to operation (c) subjecting the first probe to an amplification reaction to generate an amplified nucleic acid molecule that corresponds to the first HLA variant sequence and immobilizing the amplified nucleic acid molecule on the 3D matrix.

Embodiment 80. The method of any one of embodiments 1-78, wherein the first probe is a circularizable probe.

Embodiment 81. The method of embodiment 80, wherein the circularizable probe is a padlock probe.

Embodiment 82. The method of embodiment 81, wherein the padlock probe comprises:
 a first end;
 a second end;
 a 5' terminal region; and
 a 3' terminal region; and
wherein the 5' terminal region and the 3' terminal region hybridize to the nucleic acid corresponding to the first HLA variant sequence.

Embodiment 83. The method of embodiment 82, further comprising circularizing the padlock probe by ligating the first end and the second end of the padlock probe together, thereby generating a circularized padlock probe.

Embodiment 84. The method of embodiment 82, wherein the first end and the second end are contiguous.

Embodiment 85. The method of embodiment 82, wherein the first end and the second end are separated by a gap region containing at least one nucleotide.

Embodiment 86. The method of embodiment 85, wherein the gap region contains from 2 to 500 nucleotides.

Embodiment 87. The method of embodiment 86, further comprising filling the gap region by incorporating at least one nucleotide in an extension reaction.

Embodiment 88. The method of any one of embodiments 76-87, wherein the amplification reaction is a rolling circle amplification (RCA) reaction.

Embodiment 89. The method of any one of embodiments 76-88, wherein:
 the nucleic acid corresponding to the first HLA variant sequence is a DNA molecule hybridized to an RNA molecule;
 the nucleic acid corresponding to the first HLA variant sequence comprises a first sequence;
 the RNA molecule comprises a second sequence;
 the first sequence is the reverse complement of the second sequence;
 the method further comprises, prior to (b);
  (i) degrading or digesting at least a portion of the RNA molecule; and
 the second sequence is identified based on the identification of at least a portion of the amplified nucleic acid sequence.

Embodiment 90. The method of embodiment 89, wherein the DNA molecule is a cDNA molecule.

Embodiment 91. The method of embodiment 89 or 90, wherein:
 the biological sample is present in a 3D matrix; and
 the DNA molecule is immobilized to the 3D matrix.

Embodiment 92. The method of any one of embodiments 89-90, wherein:
the biological sample is present in a 3D matrix; and
the first probe is immobilized to the 3D matrix.

Embodiment 93. The method of any one of embodiments 1-92, further comprising administering a treatment to the subject, wherein the treatment is selected for administration to the subject based at least partially on the spatial distribution of the HLA variant sequence in the biological sample.

Embodiment 94. The method of embodiment 93, wherein the treatment comprises an immunotherapy.

Embodiment 95. The method of embodiment 93, wherein the treatment comprises a checkpoint inhibitor.

Embodiment 96. The method of embodiment 93, wherein the treatment comprises a cancer vaccine.

Embodiment 97. The method of embodiment 93, wherein the treatment comprises a chimeric antigen receptor T-cell therapy.

Embodiment 98. The method of embodiment 93, wherein the treatment comprises a recombinant T-cell therapy.

Embodiment 99. A method of identifying a location of a human leukocyte antigen (HLA) allele in a biological sample comprising targeting a nucleobase to a nucleic acid molecule encoding the HLA allele in the biological sample and identifying a sequence of the nucleic acid molecule or derivative thereof in situ to identify the location of the HLA allele within the biological sample.

Embodiment 100. A method of identifying a location of a human leukocyte antigen (HLA) allele in a biological sample comprising targeting a nucleic acid probe molecule to a nucleic acid molecule encoding the HLA allele in the biological sample and identifying a sequence of the nucleic acid molecule or derivative thereof in situ to identify the location of the HLA allele within the biological sample.

Examples

The following examples are included for illustrative purposes only and are not intended to limit the scope of the disclosure.

Example 1-RNA-Seq Guided Selection and Administration of Cancer Treatment

Cancer treatment is selected and administered based on RNA sequencing of a tumor.

A tumor biopsy is taken from a subject and placed in a microcentrifuge tube. The biopsy sample is homogenized in 1 mL of TRIzol™ reagent (TRI Reagent®) (a monophasic solution of phenol and guanidinium isothiocyanate) per 10 cm² of tissue area. The homogenized tissue is then transferred to a centrifuge tube. The homogenized tissue is then spun in a centrifuge at 12,000×g for 10 minutes at 4° C. The supernatant is then transferred to a fresh tube which is incubated at room temperature for 5 minutes. Chloroform is then added at a ratio of 1:5 chloroform to TRI Reagent® (a monophasic solution of phenol and guanidinium isothiocyanate) and the tube is shaken and incubated at room temperature for 2 minutes. Following the incubation period, the centrifuge tube is spun at 12,000×g for fifteen minutes at 4° C. After centrifugation, the aqueous (top) phase is collected via a pipette and 70% EtOH is added to the aqueous phase in a 1:1 ratio of ethyl alcohol (EtOH) to the aqueous phase. 700 μL of the EtOH/aqueous mixture is then added to a RNeasy® column (RNA purification column). The RNeasy® column (RNA purification column) is spun at 12,000×g for 30 seconds and the flow through is discarded. 700 μL of RW1 buffer (from an RNeasy® kit) is added to the column which is again spun at 12,000×g for 30 seconds. 500 μL of RPE buffer (wash buffer from an RNeasy® kit) is added to the column which is spun at 12,000×g before the flow through is discarded. 500 μL of RPE buffer (wash buffer) is then again added to the column which is spun at 12,000×g before the flow through is discarded. The column is then spun via a centrifuge at 12,000×g for 2 minutes to dry the column of EtOH. 50 μL of Ribonuclease (RNase)/deoxyribonuclease (DNase)-free H$_2$O is added to the column. 1 minute later the column is spun at 12,000×g for 5 minutes. Following this centrifugation, the column eluate (which contains isolated RNA) is transferred to a new tube. The absorbance of the RNA solution is measured at 260 nm and 280 nm to determine the RNA concentration of the solution.

RNA transcripts are enriched via a RiboMinus™ Eukaryote Kit for RNA-Seq. Library construction is performed using a SOLID® (Sequencing by Oligonucleotide Ligation and Detection) Total RNA-Seq Kit. SOLID® (Sequencing by Oligonucleotide Ligation and Detection) next-generation sequencing is performed to assess the expression of genes including epidermal growth factor receptor (EGFR), HLA and cancer/testis antigen (CTA) genes. Results show that the tumor is an EGFR negative tumor that expresses HLA-A*02:02 and a CTA. The tumor is treated via the administration of recombinant T-cells containing T-cell receptors targeted towards MHC-antigen complexes displaying the CTA. Treatment is unable to eliminate the tumor. A physician realizes that the recombinant T-cell therapy lacks efficacy. The physician recommends a chemotherapeutic agent as a second line therapy. The delay in administration of the second line therapy decreases the likelihood of a positive outcome for the patient.

Example 2-Selection and Administration of Cancer Treatment Using a Method of the Disclosure HLA and CTA genes are labelled with probe molecules of the disclosure. A visual representation of HLA and CTA expression is generated by a computer algorithm via the analysis of FISSEQ data. The generated visual representation is used to guide the selection of cancer treatment.

A tumor biopsy is taken from a subject and fixed using 4% formaldehyde for overnight, followed by 3 washes (including on overnight wash) with 70% EtOH. The sample is washed using PBS and cross-linked using 100 μM BS(PEG)9 (Thermo Fisher Scientific®) in PBS for 1 hour, followed by 1M Tris treatment for fifteen minutes. The biopsy sample is then incubated with probe molecules designed to target EGFR, CTA, and various HLA genes including HLA-A*02:02. Padlocks are then added to the sample to allow hybridization of the circularizing probe molecules, such as padlock probes. The circularization mixture containing 2000U T4 DNA ligase in 10× T4 ligase buffer (NEB®) is then added, and the sample is incubated at 60° C. for two hours. Alternatively, the circularization mixture can contain 25U CircLigase™ (Epicentre®), 1 mM MnCl and 1 M Betain. The RCA primer is then hybridized to the sample at 60° C. for fifteen minutes and washed. For rolling circle amplification, 100 U phi29 DNA polymerase (Enzymatics®), 250 μM dNTP and 40 μM aminoallyl dNTP are added to the sample and incubated at 30° C. overnight. The sample is then washed using PBS and cross-linked using 100 μM BS(PEG)9 in PBS for 1 hour, followed by 1M Tris treatment for fifteen minutes. For the amplification product detection via FISSEQ analysis, 1 μM fluorescently label oligonucleotides will be diluted in 2×SSC and hybridized to the matrix containing the DNA amplicons at 60° C. and washed. Imaging is performed using Leica® SP5 scanning confocal microscope using 10×, 20× or 63× objectives in four color channels (FITC, Cy3, Texas Red® (Sulforhodamine 101 acid chloride), and Cy5).

Detection of amplification products allows for the identification of each type of probe molecule within the biological sample. Each type of probe molecule is bound to nucleotide corresponding to a variant sequence encoding EGFR, a HLA or CTA gene. Thus, the location of each probe molecule is indicative of EGFR, HLA, or CTA gene expression. A computer program then assigns a color to each probe molecule detected and generates a spatial map of HLA and CTA gene expression.

The spatial map of gene expression shows that, although the tumor expresses CTA, this expression is limited to only a small portion of the tumor, as shown in FIG. 4. A physician thus administers recombinant T-cells containing T-cell receptors targeted towards MHC-antigen complexes displaying CTA in combination with chemotherapeutic agents as a second-line therapy. A lack of delay in administration of the second-line therapy increases the odds of a positive patient outcomes.

Example 3-Targeting Multiple Clonal Populations Identified with a Method of the Disclosure HLA, somatic mutations, and tumor associated antigens are labelled with probe molecules of the disclosure. A visual representation of HLA, somatic mutations, and tumor associated antigen expression is generated by a computer algorithm via the analysis of FISSEQ data. The generated visual representation is used to guide the selection of multiple immunotherapies administered in combination for cancer treatment.

A tumor biopsy is taken from a subject and fixed using 4% formaldehyde for overnight, followed by 3 washes (including on overnight wash) with 70% EtOH. The sample is washed using PBS and cross-linked using 100 μM BS(PEG)9 (Thermo Fisher Scientific®) in PBS for 1 hour, followed by 1M Tris treatment for fifteen minutes. The biopsy sample is then incubated with probe molecules designed to target EGFR, CTA, and various HLA genes including HLA-A*02:02. Padlocks are then added to the sample to allow hybridization of the padlocks to the probe molecules. The circularization mixture containing 2000U T4 DNA ligase in 10× T4 ligase buffer (NEB®) is then added, and the sample is incubated at 60° C. for two hours. Alternatively, the circularization mixture can contain 25U CircLigase™ (Epicentre®), 1 mM MnCl and 1 M Betain. The RCA primer is then hybridized to the sample at 60° C. for fifteen minutes and washed. For rolling circle amplification, 100 U phi29 DNA polymerase (Enzymatics®), 250 μM dNTP and 40 μM aminoallyl dNTP are added to the sample and incubated at 30° C. overnight. The sample is then washed using PBS and cross-linked using 100 μM BS(PEG)9 in PBS for 1 hour, followed by 1M Tris treatment for fifteen minutes. For the amplification product detection via FISSEQ analysis, 1 μM fluorescently label oligonucleotides will be diluted in 2×SSC and hybridized to the matrix containing the DNA amplicons at 60° C. and washed. Imaging is performed using Leica® SP5 scanning confocal microscope using 10×, 20× or 63× objectives in four color channels (FITC, Cy3, Texas Red® (Sulforhodamine 101 acid chloride) and Cy5).

Detection of amplification products allows for the identification of each type of probe molecule within the biological sample. Each type of probe molecule is bound to nucleotide corresponding to a variant sequence encoding EGFR, a HLA or CTA gene. Thus, the location of each probe molecule is indicative of EGFR, HLA, or CTA gene expression. A computer program then assigns a color to each probe molecule detected and generates a spatial map of HLA and CTA gene expression.

The spatial map of gene expression shows two clonal populations of cancer cells-clones expressing EGFR and HLA-A*02:02 that do not express CTA, and clones expressing CTA and HLA-A*02:02 that do not express EGFR. A physician thus administers two therapies simultaneously. One therapy contains recombinant T-cells engineered to target the CTA-HLA-A*02:02 complexes, while the other therapy is the EGFR inhibitor erlotinib. Treatment with both therapies increases the odds of a positive patient outcome versus treatment with either single therapy alone, as clones expressing the CTA-HLA-A*02:02 complexes but not EGFR are resistant to erlotinib, and clones expressing EGFR but not the CTA can evade the recombinant T-cell therapy.

Example 4-Prioritizing Somatic Variants in Cancer Vaccines

HLA and somatic mutations are labelled with probe molecules of the disclosure. A visual representation of HLA, somatic mutations, and tumor associated antigen expression is generated by a computer algorithm via the analysis of FISSEQ data. The generated visual representation is used to guide the selection of multiple immunotherapies administered in combination for cancer treatment.

A tumor biopsy is taken from a subject. Part of this tumor biopsy is used for next generation sequencing to identify somatic variants and the germline class I HLA alleles. The remainder is fixed using 4% formaldehyde for overnight, followed by 3 washes (including on overnight wash) with 70% EtOH. The sample is washed using PBS and cross-linked using 100 μM BS(PEG)9 (Thermo-Fisher Scientific®) in PBS for 1 hour, followed by 1M Tris treatment for fifteen minutes. The biopsy sample is then incubated with probe molecules designed to somatic mutations and various HLA alleles. Padlocks are then added to the sample to allow hybridization of the padlocks to the probe molecules. The circularization mixture containing 2000U T4 DNA ligase in 10× T4 ligase buffer (NEB®) is then added, and the sample is incubated at 60° C. for two hours. Alternatively, the circularization mixture can contain 25U CircLigase™ (Epicentre®), 1 mM MnCl and 1 M Betain. The RCA primer is then hybridized to the sample at 60° C. for fifteen minutes and washed. For rolling circle amplification, 100 U phi29 DNA polymerase (Enzymatics®), 250 μM dNTP and 40 μM aminoallyl dNTP are added to the sample and incubated at 30° C. overnight. The sample is then washed using PBS and cross-linked using 100 μM BS(PEG)9 in PBS for 1 hour, followed by 1M Tris treatment for fifteen minutes. For the amplification product detection via FISSEQ analysis, 1 μM fluorescently label oligonucleotides will be diluted in 2×SSC and hybridized to the matrix containing the DNA amplicons at 60° C. and washed. Imaging is performed using Leica SP5 scanning confocal microscope using 10×, 20× or 63× objectives in four color channels (FITC, Cy3, Texas Red® (Sulforhodamine 101 acid chloride) and Cy5).

Detection of amplification products allows for the identification of each type of probe molecule within the biological sample. Each type of probe molecule is bound to nucleotide corresponding to a variant sequence encoding a somatic variant or a class I HLA allele. A computer program then assigns a color to each probe molecule detected and generates a spatial map of HLA and somatic variant expression. This map is used to predict the level of expression of each somatic variant, as well as colocalization of somatic variants and HLA expression.

The spatial map of gene expression shows three clonal populations of cancer cells. Two clones are observed to express all class I HLA alleles, while no expression from the germline HLA-A*02:02 allele is observed in the third clone. The therapeutic vaccine construct can target at most twenty neoantigens, so the twenty most effective neoantigens may be prioritized for inclusion. However, there is no one presented neoantigen that is present on all of the three clones. To ensure the complete tumor is targeted, neoantigens a selected based to the spatial map to ensure coverage of each of the three clones and to avoid neoantigens presented by the HLA-A*02:02 allele on the third clone.

Example 5-Assessment of HLA Variants and Immune Marker Expression

This example illustrates the use of a tumor's HLA type and specific probes and to create a clonal map of the allele-specific expression of class I HLA genes. In the same sample, the expression of immune cell markers was also mapped. Padlock probes were designed against target sequences for the class I HLA genes and immune genes including CD3 and CD4. HLA typing was performed to the tumor prior to probe design. The tumor's HLA type was assigned from the RNA sequencing data using the software Optitype (see e.g., Szolekk et al., Bioinformatics (2014) 30(23): 3310-6).

A tumor biopsy was obtained and fixed using 4% formaldehyde. The sample was washed cross-linked and treated with Tris. The sample was then incubated with the probe molecules to allow hybridization to nucleic acids in the sample. A circularization mixture containing a ligase in a buffer was added to the sample and incubated. Following ligation of the padlock probes, a primer was added to the sample for rolling circle amplification (RCA). The sample was incubated with a mixture of phi29 DNA polymerase and dNTPs and then washed using PBS.

For detection via FISSEQ analysis, fluorescently label oligonucleotides were added to the sample for hybridization. Imaging was performed to detect the RCA products and identify target nucleic acid molecules within the biological sample. A computer program then assigned a color to each target allele or gene detected via the analysis of the FISSEQ data and generated a spatial map of HLA and somatic variant expression. As shown in FIG. 5A-5B, the image shows a visual representation of detected expression of the indicated somatic variant, as well as presence of T cell markers. In the sample, HLA-A and HLA-B variant expression was observed in proximity to markers of T cells. HLA Class I variants were detected by spatial sequencing in lung adenocarcinoma despite sequence homology.

Using this approach and methods described herein, clonal antigen presentation can be detected including a combination of HLA expression and the expression of various cancer antigens, immune markers, and/or inflammation markers. In some examples, this can provide a spatial map of the tumor microenvironment and provide a method for evaluating and/or monitoring the effectiveness of therapies such as HLA-restricted immunotherapies, such as cancer vaccines. In some aspects, HLA clonal information can be used to prioritize neoantigens presented throughout the tumor. In some cases, the methods described herein may provide insight into why immunotherapies fail for some individuals. In some cases, tumors with sufficient HLA antigen presentation throughout the tumor can be identified as potential candidates for immunotherapy such as checkpoint inhibitors. In some aspects, HLA clonal information can be used to select most effective therapies and/or exclude patients from high-risk treatments where immune evasion is likely.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of analyzing a biological sample from a subject, comprising:
   (a) providing a biological sample comprising multiple different populations of cells, wherein a population of cells of the multiple different populations of cells comprises a first nucleic acid sequence and a second nucleic acid sequence, wherein the first nucleic acid sequence corresponds to a major histocompatibility complex (MHC) variant sequence;
   (b) coupling a first probe to the first nucleic acid sequence and coupling a second probe to the second nucleic acid sequence; and
   (c) detecting the first probe and the second probe, thereby determining that the first nucleic acid sequence and the second nucleic acid sequence are co-localized within the population of cells in the biological sample.

2. The method of claim 1, wherein the second nucleic acid sequence comprises a mutation.

3. The method of claim 1, wherein the second nucleic acid sequence corresponds to a marker of inflammation.

4. The method of claim 1, wherein the second nucleic acid sequence corresponds to a marker for cell typing.

5. The method of claim 1, wherein the second nucleic acid sequence corresponds to a marker for an immune cell.

6. The method of claim 1, wherein the second nucleic acid sequence corresponds to an additional MHC variant sequence.

7. The method of claim 6, further comprising identifying a clone within the biological sample based on a first location of the first nucleic acid sequence and a second location of the second nucleic acid sequence.

8. The method of claim 7, further comprising generating a visual representation of a third location of the clone within the biological sample for display on a graphical user interface (GUI).

9. The method of claim 6, wherein the second nucleic acid sequence comprises an MHC allele.

10. The method of claim 1, further comprising generating a visual representation of a first location of the first nucleic acid sequence and a second location of the second nucleic acid sequence for display on a graphical user interface (GUI).

11. The method of claim 1, further comprising identifying a cell or derivative thereof within the biological sample, wherein the cell or derivative thereof comprises the first nucleic acid sequence and the second nucleic acid sequence.

12. The method of claim 1, further comprising predicting a presentation of a peptide on an MHC protein expressed in the biological sample, wherein the peptide is at least partially encoded by the second nucleic acid sequence and the MHC protein is at least partially encoded by the first nucleic acid sequence.

13. The method of claim 12, wherein the peptide is a mutant peptide.

14. The method of claim 1, wherein the determining that the first nucleic acid sequence and the second nucleic acid sequence are co-localized within the population of cells in the biological sample further comprises identifying the first nucleic acid sequence.

15. The method of claim 14, wherein the first nucleic acid sequence comprises an MHC allele.

16. The method of claim 1, wherein (a) further comprises providing the biological sample within a three-dimensional (3D) matrix that preserves spatial information of the first nucleic acid sequence prior to (b).

17. The method of claim 16, wherein the biological sample is provided within the 3D matrix by directing a precursor of the 3D matrix through the biological sample and subjecting the precursor of the 3D matrix to a reaction to generate cross-links and form the 3D matrix.

18. The method of claim 1, further comprising, subjecting the first probe to an amplification reaction to generate an amplified nucleic acid molecule that corresponds to the MHC variant sequence.

19. The method of claim 1, wherein the first probe is a circularizable probe.

20. The method of claim 1, further comprising contacting the biological sample with a plurality of fluorescently labeled oligonucleotides to identify at least a portion of the first probe.

* * * * *

SEQUENCE LISTING

```
Sequence total quantity: 4
SEQ ID NO: 1            moltype = DNA  length = 57
FEATURE                 Location/Qualifiers
source                  1..57
                        mol_type = genomic DNA
                        organism = Homo sapiens
SEQUENCE: 1
gcgccgtgga tagagcagga ggggccggag tattgggacc aggagacacg gaatatg     57

SEQ ID NO: 2            moltype = DNA  length = 57
FEATURE                 Location/Qualifiers
source                  1..57
                        mol_type = genomic DNA
                        organism = Homo sapiens
SEQUENCE: 2
```

```
gcgccgtgga tagagcagga gggtccggag tattgggacg gggagacacg gaaagtg        57

SEQ ID NO: 3           moltype = DNA  length = 57
FEATURE                Location/Qualifiers
source                 1..57
                       mol_type = genomic DNA
                       organism = Homo sapiens
SEQUENCE: 3
gcgccgtgga tagagcagga ggggccggag tattgggacc aggagacacg gaatgtg        57

SEQ ID NO: 4           moltype = DNA  length = 57
FEATURE                Location/Qualifiers
source                 1..57
                       mol_type = genomic DNA
                       organism = Homo sapiens
SEQUENCE: 4
gcgccgtgga tagagcagga ggggccggag tattgggacg gggagacagg gaaagtg        57
```